(12) United States Patent
Hart et al.

(10) Patent No.: US 8,493,574 B2
(45) Date of Patent: Jul. 23, 2013

(54) IMAGING SHAPE CHANGES IN EAR CANALS

(71) Applicant: Massachusetts Institute of Technology, Cambridge, MA (US)

(72) Inventors: Douglas P. Hart, Charlestown, MA (US); Federico Frigerio, Chestnut Hill, MA (US); Douglas M. Johnston, Winchester, MA (US); Manas C. Menon, Boston, MA (US); Daniel Vlasic, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

(21) Appl. No.: 13/760,576

(22) Filed: Feb. 6, 2013

(65) Prior Publication Data
US 2013/0152670 A1 Jun. 20, 2013

Related U.S. Application Data

(63) Continuation of application No. 13/169,972, filed on Jun. 27, 2011, now Pat. No. 8,384,916, which is a continuation-in-part of application No. 12/508,804, filed on Jul. 24, 2009, now Pat. No. 8,107,086.

(60) Provisional application No. 61/083,394, filed on Jul. 24, 2008, provisional application No. 61/165,708, filed on Apr. 1, 2009.

(51) Int. Cl.
*G01B 11/14* (2006.01)
*G01B 11/24* (2006.01)
*G01B 11/00* (2006.01)

(52) U.S. Cl.
CPC ............... *G01B 11/14* (2013.01); *G01B 11/24* (2013.01); *G01B 11/00* (2013.01)

USPC ........................... 356/625; 356/626; 356/601

(58) Field of Classification Search
CPC .......... G01B 11/14; G01B 11/24; G01B 11/00
USPC ................... 356/600–613, 625–626, 432–436
See application file for complete search history.

(56) References Cited

U.S. PATENT DOCUMENTS

| 4,841,156 A | 6/1989 | May et al. |
| 5,487,012 A | 1/1996 | Topholm et al. |

(Continued)

FOREIGN PATENT DOCUMENTS

| EP | 2178012 | 4/2010 |
| JP | 2003075126 | 3/2003 |

(Continued)

OTHER PUBLICATIONS

Prasciolu, M et al., "Three-dimensional digital scanner based on micromachined micromirror for the metrological measurement of the human ear canal", J. Vac. Sci. Technol B. vol. 23, No. 6, Nov./Dec. 2005, pp. 2990-2994.

(Continued)

Primary Examiner — Michael P Stafira
(74) Attorney, Agent, or Firm — Strategic Patents, P.C.

(57) ABSTRACT

The attenuation and other optical properties of a medium are exploited to measure a thickness of the medium between a sensor and a target surface. Disclosed herein are various mediums, arrangements of hardware, and processing techniques that can be used to capture these thickness measurements and obtain dynamic three-dimensional images of the target surface in a variety of imaging contexts. This includes general techniques for imaging interior/concave surfaces as well as exterior/convex surfaces, as well as specific adaptations of these techniques to imaging ear canals, human dentition, and so forth.

14 Claims, 26 Drawing Sheets

U.S. PATENT DOCUMENTS

| | | | |
|---|---|---|---|
| 5,619,330 | A | 4/1997 | Ehemann, Jr. et al. |
| 5,717,217 | A | 2/1998 | Neckers et al. |
| 5,904,651 | A | 5/1999 | Swanson et al. |
| 6,339,648 | B1 | 1/2002 | Mcintosh et al. |
| 6,533,062 | B1 | 3/2003 | Widmer et al. |
| 6,540,045 | B1 | 4/2003 | Widmer et al. |
| 6,621,951 | B1 | 9/2003 | Zhao et al. |
| 6,751,494 | B2 | 6/2004 | Collier et al. |
| 6,827,178 | B2 | 12/2004 | Widmer et al. |
| 6,863,151 | B2 | 3/2005 | Widmer et al. |
| 7,014,010 | B2 | 3/2006 | Widmer |
| 7,286,242 | B2 | 10/2007 | Kim et al. |
| 7,555,356 | B2 | 6/2009 | Roth et al. |
| 7,606,381 | B2 | 10/2009 | Haussmann |
| 8,107,086 | B2 | 1/2012 | Hart et al. |
| 2004/0112978 | A1 | 6/2004 | Reichel et al. |
| 2004/0253824 | A1 | 12/2004 | Tegeder |
| 2005/0088435 | A1* | 4/2005 | Geng ................. 345/419 |
| 2005/0202363 | A1 | 9/2005 | Osterwalder |
| 2006/0173637 | A1 | 8/2006 | Martin |
| 2006/0287612 | A1 | 12/2006 | Duda et al. |
| 2007/0127756 | A1 | 6/2007 | Slabaugh et al. |
| 2008/0068619 | A1 | 3/2008 | Vial et al. |
| 2008/0169044 | A1 | 7/2008 | Osborne et al. |
| 2009/0296980 | A1* | 12/2009 | Yi ................. 382/100 |
| 2010/0019170 | A1 | 1/2010 | Hart et al. |
| 2010/0020070 | A1 | 1/2010 | Hart et al. |
| 2010/0022893 | A1 | 1/2010 | Hart |
| 2010/0027014 | A1 | 2/2010 | Hart et al. |
| 2010/0039534 | A1 | 2/2010 | Hart et al. |
| 2010/0042002 | A1 | 2/2010 | Hart et al. |
| 2010/0065793 | A1 | 3/2010 | Hart et al. |
| 2010/0067756 | A1 | 3/2010 | Hart et al. |
| 2011/0290005 | A1 | 12/2011 | Hart et al. |

FOREIGN PATENT DOCUMENTS

| | | |
|---|---|---|
| WO | WO-2010/011938 A1 | 1/2010 |
| WO | WO-2013002935(A1) | 1/2013 |

OTHER PUBLICATIONS

"U.S. Appl. No. 12/508,804, Notice of Allowance mailed Sep. 27, 2011", 14 pgs.

"U.S. Appl. No. 12/508,804, Non Final Office Action mailed Jul. 25, 2011", 15 pages.

"U.S. Appl. No. 12/508,866, Non-Final Office Action mailed Jul. 19, 2011", 13 pages.

"U.S. Appl. No. 12/508,866, Final Office Action mailed May 18, 2011", 21 pages.

Pirzanski, Chester, "Earmolds and Hearing Aid Shells: A Tutorial Part 2: Impression-Taking Techniques that Result in Fewer Remakes", May 2006 The Hearing review Mar. 11, 2011, pp. 1-7.

Hidrovo, C et al., ""Dual Emission Laser Induced Fluorescence Technique (DELIF) for Oil Film Thickness and Temperature Measurement"", AMSE / JSME Fluids Engineering Decision Summer Meeting Jul. 23-28, 2000 Boston, MA 2000, pp. 1-8.

"U.S. Appl. No. 12/508,866, Notice of Allowance mailed Dec. 21, 2011", 13 pgs.

"International Application Serial No. PCT/US09/51710, Search Report and Written Opinion mailed Nov. 19, 2009", 15 Pgs.

"U.S. Appl. No. 12/509,091, Notice of Allowance mailed Nov. 15, 2011", 16 pgs.

"U.S. Appl. No. 12/508,991, Notice of Allowance mailed Nov. 14, 2011", 6 Pgs.

"International Application Serial No. PCT/US12/39942, Search Report and Written Opinion mailed Oct. 18, 2012", 13 pages.

"U.S. Appl. No. 12/508,991, Non-Final Office Action mailed Oct. 13, 2011", 14 Pgs.

"U.S. Appl. No. 12/508,866, Non-Final Office Action mailed Jan. 31, 2011", 18 pages.

Hidrovo, C. et al., ""2-D Thickness and Temperature Mapping of Fluids by Means of a Two Dye Laser Induced Fluorescence Ratiometric Scheme"", Journal of Flow Visualization and Image Processing vol. 9, Issue 2 Jun. 2002, pp. 171-191.

Hidrovo, C. et al., ""Excitation Non-Linearities in Emission Reabsorption Laser Induced Fluorescence (ERLIF) Techniques"", Journal of Applied Optics vol. 43, No. 4 Feb. 2004, pp. 894-913.

Hidrovo, Carlos H. et al., "Emission reabsorption laser induced fluorescence (ERLIF) film thickness measurement", Department of Mechanical Engineering, Measurement and Science Technology, Massachusetts Institute of Technology, Cambridge, MA 02139-4307, USA, vol. 12 Jan. 15, 2001, pp. 467-477.

"U.S. Appl. No. 13/169,972, Notice of Allowance mailed Dec. 24, 2012",, 20.

* cited by examiner

IMAGING SHAPE CHANGES IN EAR CANALS

CROSS-REFERENCE TO RELATED APPLICATIONS

This application is a continuation of U.S. patent application Ser. No. 13/169,972 filed Jun. 27, 2011, which is a continuation-in-part of U.S. patent application Ser. No. 12/508,804 filed Jul. 24, 2009 now U.S. Pat. No. 8,107,086 issued on Jan. 31, 2012, which claims the benefit U.S. Provisional Patent Applications No. 61/083,394 filed on Jul. 24, 2008 and U.S. Provisional Patent Application No. 61/165,708 filed on Apr. 1, 2009, each of which is hereby incorporated by reference in its entirety.

BACKGROUND

Various techniques have been disclosed for capturing thickness measurements using Emission Reabsorption Laser Induced Fluorescence ("ERLIF") as described for example in the following literature, all incorporated by reference herein in its entirety: Hidrovo, C, Hart, D. P., "Excitation Non-Linearities in Emission Reabsorption Laser Induced Fluorescence (ERLIF) Techniques," *Journal of Applied Optics*, Vol. 43, No. 4, February 2004, pp. 894-913; Hidrovo, C., Hart, D. P., "2-D Thickness and Temperature Mapping of Fluids by Means of a Two Dye Laser Induced Fluorescence Ratiometric Scheme," *Journal of Flow Visualization and Image Processing*, Volume 9, Issue 2, June 2002; Hidrovo, C., Hart, D. P., "Emission Reabsorption Laser Induced Fluorescence for Film Thickness Measurement," *Measurement Science and Technology*, Vol. 12, No. 4, 2001, pp. 467-477; and Hidrovo, C., Hart, D. P., "Dual Emission Laser Induced Fluorescence Technique (DELIF) for Oil Film Thickness and Temperature Measurement," *ASME/JSME Fluids Engineering Division Summer Meeting*, Jul. 23-28, 2000, Boston, Mass.

While these existing techniques provide a useful approach for obtaining thickness measurements, they rely on various mixtures of two or more fluorescent dyes. There remains a need for other thickness measurement techniques that do not require the use of multiple dyes, as well as techniques for adapting thickness measurements to various physical contexts for three-dimensional imaging.

SUMMARY

The attenuation and other optical properties of a medium are exploited to measure a thickness of the medium between a sensor and a target surface. Disclosed herein are various mediums, arrangements of hardware, and processing techniques that can be used to capture these thickness measurements and obtain dynamic three-dimensional images of the target surface in a variety of imaging contexts. This includes general techniques for imaging interior/concave surfaces as well as exterior/convex surfaces, as well as specific adaptations of these techniques to imaging ear canals, human dentition, and so forth.

BRIEF DESCRIPTION OF THE FIGURES

The invention and the following detailed description of certain embodiments thereof may be understood by reference to the following figures.

DETAILED DESCRIPTION

Figure 1:
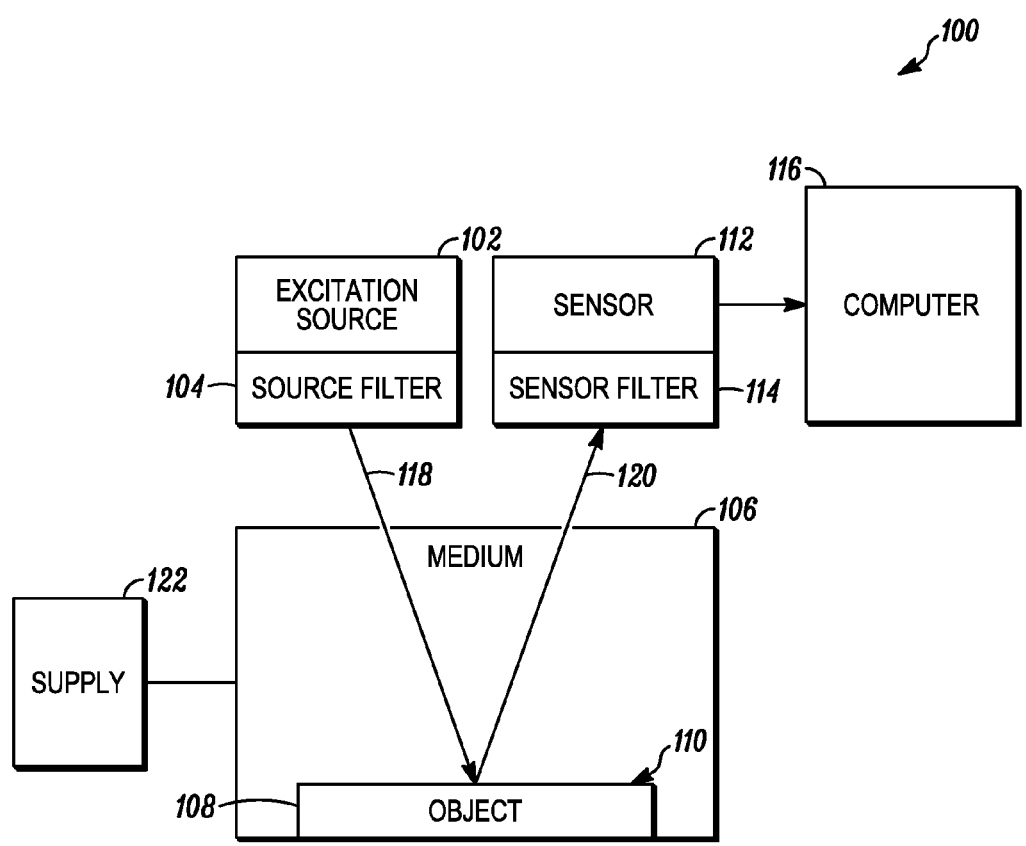
FIG. 1 shows a three-dimensional imaging system.

Disclosed herein are various techniques for obtaining thickness measurements from a film, liquid, gel, gas, or other medium based upon the relationship between an intensity of light measured at two or more different wavelengths. Also disclosed herein are various techniques for capturing such thickness measurements in interior volumes (such as ear canals), exterior volumes (such as teeth), and so forth for use in three-dimensional reconstruction. In general, the systems and methods described below exploit the Beer-Lambert Law for absorption of light in a medium, and more particularly, derivations based upon the Beer-Lambert Law where one wavelength is attenuated more than another as it passes through a medium. By controlling sources of light and the properties of the medium, this differential attenuation can be used to determine a distance that light travels through a medium to a sensor. More specific applications of this general principle are provided below, and serve to outline several variations of a new technique for distance measurement based upon differential attenuation of various wavelengths of light.

Throughout this disclosure, the term "absorption" is used to describe an attenuation of energy such as electromagnetic energy propagating through a medium. This attenuation may be caused by physical absorption in the medium, or by any other physical phenomenon (such as scattering) or combination of phenomena that result in a measurable decrease in intensity of a signal as it passes through the medium. For example, it will be understood that in some embodiments—such as those involving gold nanoparticles as described herein—"absorption" is the result of multiple inelastic scattering events. Thus as used herein absorption should be understood broadly to refer to any form or cause of attenuation (or lack thereof) unless a more specific meaning is explicitly provided or otherwise clear from the context.

In the following description, terms such as thickness, thickness calculation, and thickness measurement are used interchangeably to describe the thicknesses as determined using the techniques disclosed herein. In general, no particular meaning should be ascribed to the terms "measurement" and "calculation", and the use of one term or the other, or similar references to "determining", "calculating", or "obtaining" thickness measurement, is not intended to imply any distinction among the manners in which thickness might be determined. Rather, all such references to thickness should be understood to include all of the techniques described herein for determining thickness of a medium or the length of an optical path therethrough, except where a more specific meaning is explicitly provided.

Throughout this disclosure, various terms of quantitative and qualitative description are used. These terms are not intended to assert strict numerical boundaries on the features described, but rather should be interpreted to permit some variability. Thus for example where medium is described as being transparent at a particular wavelength, this should be understood to mean substantially transparent or sufficiently transparent to permit measurements yielding accurate thickness calculations, rather than absolutely transparent at the limits of measurement or human perception. Similarly, where a target surface is described as having uniform color or a dye is described as fluorescing at a particular wavelength, this should not be interpreted to exclude the variability typical of any conventional material or manufacturing process. Thus in the following description, all descriptive terms and numerical values should be interpreted as broadly as the nature of the invention permits, and will be understood by one of ordinary skill in the art to contemplate a range of variability consistent with proper operation of the inventive concepts disclosed herein, unless a different meaning is explicitly provided or otherwise clear from the context.

In the following description, the term wavelength is used to describe a characteristic of light or other electromagnetic energy. It will be understood that the term wavelength may refer to a specific wavelength, such as where the description refers to a center frequency or a limit or boundary for a range of frequencies. The term may also or instead refer generally to a band of wavelengths, such as where a wavelength is specified for a sensor, pixel, or the like. Thus in general the term wavelength as used herein should be understood to refer to either or both of a specific wavelength and a range of wavelengths unless a more specific meaning is provided or otherwise clear from the context.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

Although the following disclosure includes example embodiments, these examples are provided for illustration only and are not intended in a limiting sense. All variations, modifications, extensions, applications, combinations of components, and the like as would be apparent to one of ordinary skill in the art are intended to fall within the scope of this disclosure.

FIG. 1 shows a three-dimensional imaging system. In an embodiment, the system 100 may employ a fluorescent medium between an object and a camera, although it will be readily appreciated that a variety of mediums, sensors, and other components may be used. The system 100 may include an excitation source 102 with a source filter 104, a medium 106, an object 108 with a target surface 110, a sensor 112 with a sensor filter 114, and a computer 116. In general operation, the excitation source 102 illuminates the object 108 along an optical illumination path 118 through the medium 106, and the sensor 112 captures reflected light from the object 108 on an optical return path 120 through the medium 106. The resulting signal at the sensor 112 can be processed by the computer 116 to obtain thickness measurements of the medium 106, which can be further processed to obtain a three-dimensional image of the object 108. It will be understood that numerous variations, additions, omissions, and modifications are possible, all as described in the various detailed embodiments set out below.

The excitation source 102 may be any suitable light source. In various embodiments, this may include light emitting diodes, incandescent bulbs or lamps, laser light sources, or any other broadband light source, broadband visible light source, narrowband light source or any combination of the foregoing that emits photons at the desired wavelength(s). The excitation source 102 (as shaped by the source filter 104) may provide light at any suitable wavelength(s) including wavelengths that excite a fluorescent substance in the medium 106 or on the target surface 110, as well as wavelength(s) having known attenuation by the medium 106, all as more generally described below. The excitation source 102 may more generally include any source of illumination suitable for imaging as described herein. While visible light embraces one useful range of wavelengths, the excitation source 102 may also or instead usefully provide light near or beyond the visible light range such as near-infrared or infrared illumination, or more generally across any range of electromagnetic wavelengths for which attenuation by the medium 106 can be measured. Various other embodiments are discussed in greater detail below, and it will be appreciated that the term "excitation source" as used herein should be broadly understood as any source of energy capable of achieving illumination of the object 108. In one embodiment, the excitation source 102 may be a light source positioned to excite a single fluorescent substance around the object 108 (e.g., within the medium 106) to provide a fluorescent emission, or more generally to illuminate the medium 106 and/or target surface 110 as required to capture suitable intensity measurements at the sensor 112 for thickness calculations as described below.

One or more source filters 104 may optionally be employed to shape a spectral profile of the excitation source 102, such as to provide narrowband illumination from a broadband light source, or to otherwise attenuate energy outside wavelengths of interest. For example, where the sensor 112 captures a fluorescent or other radiant image from the object 108, the one or more source filters 104 may usefully remove or attenuate the fluorescence wavelength(s) from the excitation source 102 in order to avoid contamination of fluorescence images.

The medium 106 may include any substance, mixture, solution, composition or the like suitable for the imaging systems and methods described herein. In general, the medium 106 may have known and different coefficients of attenuation for two different wavelengths so that a ratio of intensity at these wavelengths can be captured and used in thickness calculations. The medium 106 may also include a single fluorescent, phosphorescent, or similarly radiant substance that contributes to the intensity of electromagnetic energy at one of the two different wavelengths. In embodiments, one of the attenuation coefficients is zero. In embodiments, one of the attenuation coefficients is greater than or less than the other, or to improve discrimination in a calculation including a ratio, significantly greater than or less than the other.

In one aspect, the medium 106 may be selected for its mechanical properties. Thus, the medium 106 may include one or more of a liquid, a gas, a solid, a gel, or other substance or combination of substances. For example, a liquid such as a silicon oil may be conveniently employed where the object 108 is small and can be fit into a bath or other container with the oil. As another example, a gas with a fluorescent dye may be usefully employed in an interior space as described in various embodiments below. In other embodiments, the medium 106 may be a casting medium such as a curable gel into which the object 108 may be pressed and removed leaving a negative impression of the object in the medium 106. In various embodiments, such a curable material may be cured while the object 108 is in the medium 106, after the object 108 has been removed from the medium 106, or some combination of these. The medium 106 may cure with the passage of time, or with the application of heat, light, pressure, or the like, or through some other activation medium.

In another aspect, the medium 106 may be selected for its optical properties such as luminescence (e.g., fluorescence) and/or attenuation. Thus the medium 106 may in general be transparent across some portion of the electromagnetic spectrum so that light passing through the medium 106 in some wavelengths is not attenuated. The medium 106 may also have a non-zero coefficient of attenuation at some wavelengths so that light at these wavelengths is attenuated as it passes through the medium 106. This may be achieved, for example, through the use of an additive such as gold nanoparticles (which can be very closely tuned to achieve attenuation at specific, narrow bands of wavelengths) or any other substance or combination of substances that achieves a desired attenuation spectral profile. The medium 106 may also contain fluorescent dyes, phosphorescent dyes, quantum dots, or some other substance or combination of substances that emits light in response to other wavelengths or other stimulus (such as an applied electrical field, a chemical reaction, and so forth). In such embodiments, the intensity of the emitted light may be used to assist calculations of a thickness of the medium 106, as described in greater detail below. The medium 106 may also or instead include any chemiluminescent material, electroluminescent material, or other material that emits light at one or more measurable wavelengths.

Thus, the medium 106 may in general include a variety of dyes, solutes, quantum dots, encapsulated silica nanoparticles, or other substances that can be combined—such as in a homogenous mixture—to provide the medium 106 with different emission properties and/or attenuation coefficients at different wavelengths. The medium 106, including additives, may be formed of biocompatible materials so that it is safe for use on, in, or in close proximity to a living organism. One useful biocompatible dye is fluorescein sodium, although it will be appreciated that a variety of biocompatible fluorescent dyes are known and may be usefully employed with the systems and methods described herein.

The object 108 may be any object having a target surface 110 from which a three-dimensional image is to be acquired. This may include, for example biological or physiological subject matter such as teeth (or a cast of teeth), bones, hands, fingerprints, or more generally any tissue, skeleton, organs, and the like including without limitation interior surfaces such as an ear canal, nasal passage, bladder, and so forth. This may also, or instead, include fabricated items such as precision-machined components, precision cast parts, fuel injectors, turbine blades, seals, or any other three-dimensional object where quality control may usefully include an evaluation of three-dimensional shape. This may also, or instead, include models that can be usefully digitized for subsequent computerized processes such as computer-automated design, computer animation, and so forth. More generally, the object 108 may be any object from which a three-dimensional image can be usefully captured.

The sensor 112 may include any sensor or group of sensors suitable for capturing, in digital or electronic form, an intensity of electromagnetic radiation at one or more wavelengths. This may include, for example, photodiodes, charge-coupled devices (CCDs), complementary metal oxide semiconductor (CMOS) devices, or any other optical sensor or combination of sensors suitable for use with the systems and methods described herein. In general, the sensor 112 may be positioned to measure an intensity of one or more wavelengths of light in a direction of a location within a region of interest on the target surface 110, such as indicated where the optical return path 120 leaves the object toward the sensor 112 and sensor filter 114.

The sensor 112 may include a two-dimensional pixel array that can capture a two-dimensional image in which a measurement at each pixel location corresponds to an intensity of one or more wavelengths of light in a direction within a field of view of the sensor 112. This may, for example, include conventional CCD arrays, such as a grayscale array, a red-green-blue (RGB) array, a cyan-magenta-yellow (CMY) array, or the like. Various techniques are known for discriminating different wavelengths including filter masks overlaying a detector to capture a particular range of wavelengths at each pixel location, a filter wheel with which time-separated (and wavelength-separated) images can be captured through each of a sequence of filters, or a prism that separates an optical path into three sub-paths each used to measure a different wavelength. In other embodiments, nested semiconductor wells or the like may be employed to measure different wavelengths at different depths within the semiconductor device. Although not separately illustrated, it will be appreciated that the sensor 112 may include a variety of camera optics such as focusing lenses, zoom lenses, prisms, mirrors, and so forth, as well as other camera hardware such as shutters, aperture controls, and so forth, any of which may be custom built for a particular imaging environment or integrated into a commercially-available camera or some combination of these.

In general, the techniques described herein use two measured wavelengths. However, it should be appreciated that additional wavelengths may be usefully employed to increase accuracy or to accommodate use with a range of different mediums 106. The measured wavelengths may be at or near specific wavelengths detected by conventional camera hardware, or at other wavelengths, and may in general include ranges or bands of varying size around certain center wavelengths according to the sensitivity of the sensors that are used and/or the properties of the excitation source 102 and the medium 106. In some embodiments the measured wavelengths are 510 nanometers and 540 nanometers, respectively.

The sensor filter 114 may be any filter or combination of filters useful for selectively passing one or more wavelengths of light to the sensor 112, including the filter masks described above for discriminating wavelengths at the sensor, or one or more filters separate from the sensor 112 for gross filtering of an incoming optical signal, such as to attenuate light outside one or more wavelengths of interest. In various embodiments the sensor filter 114 may include a switchable optical bandpass filter, an optical bandpass filter, a color filter, a stray-light filter that attenuates all light outside of the measured wavelengths, an excitation filter that attenuates over the excitation bands, and so on.

The computer 116 may include any suitable computing device or devices including without limitation a desktop computer, laptop computer, or dedicated processing device(s). The computer may include one or more general purpose or special purpose processors constructed and/or programmed to receive measurements of intensities, perform calculations to determine the thickness of an attenuation medium, and output results of the calculations as described herein. This may include the use of software, firmware, microcode, programmable gate arrays, application specific circuits, and so on. In general, the computer 116 may provide one or more high-level functions as described below.

In one aspect, the computer 116 may control operation of the excitation source 102 and sensor 112 to obtain sensor images of the object 108. This may include supplemental functions such as controlling a supply of the medium 106 or otherwise providing monitoring and control of hardware for the systems and methods described herein. In another aspect, the computer may obtain data from the sensor 112, such as a two-dimensional array of intensity values captured from a field of view that contains the object 108 and the medium 106. This may include intermediate processing such as controlling operation of the sensor 112 or a data feed from the sensor 112, as well as processing digital measurements from the sensor 112 to obtain intensity values at particular wavelengths of interest. Thus, for example, where an RGB camera is employed, the computer 116 may receive three discrete wavelength measurements for each pixel of the camera (e.g., a red wavelength, a green wavelength, and a blue wavelength) and process these RGB values at each pixel location to determine or estimate an intensity at one or more wavelengths between the discrete RGB values for use in subsequent calculations.

In another aspect, the computer 116 may calculate a thickness of the medium 106 in a direction of a location on the object 108 (e.g., along the optical return path 120 to a particular sensor/pixel location) based upon a function of the intensity at two or more specific wavelengths. In general, each sensor 112 (or pixel location within a sensor 112) provides a measurement of intensity at two different wavelengths in the direction of a location on the target surface 110, which may correspond to a general area of interest, or a particular location within a region of interest depending on the optical resolution of the sensor 112 and related hardware.

Where the medium 106 has a different attenuation coefficient at each of two measured wavelengths and the medium 106 fluoresces or otherwise radiates at one of these two wavelengths, the intensity at each of the two wavelengths can be related to a thickness of the medium 106 in the direction of the location. Suitable adaptations may be made where, for example, the medium 106 contains a fluorescent dye that is excited by the excitation source 102, or where the medium 106 contains two fluorescent dyes that are excited by the excitation source 102, or where the medium 106 has known attenuation coefficients and the target surface 110 has a known color pattern, or where the target surface 110 has a luminescent surface that luminesces at a wavelength that is attenuated by the medium 106. In some embodiments, a baseline image of the target surface 110 (e.g., taken without the medium 106 present) may be used to obtain the known color pattern. Preferably, the non-absorbing medium and the medium 106 have similar indices of refraction (i.e., they are index matched), so that the baseline image and any images taken with the medium 106 line up as exactly as possible. Translation, rotation, warping, and the like may also be employed to adapt a baseline image to various perspectives on an object, such as where a camera or other sensor obtains images from a variety of poses that are used to form a composite three-dimensional image. However adapted, this general notion may be employed to obtain a number of thickness measurements in the direction of a corresponding number of locations on the target surface 110

In another aspect, the computer 116 may process thickness measurements to obtain a three-dimensional reconstruction of the target surface 110. With a number of simple constraints such as information about the physical boundaries of the medium 106, the directionality associated with pixel or other sensor measurements, and a straightforward application of Euclidean geometry, thickness measurements can be transformed into a three-dimensional data set representing the target surface 110. This three-dimensional data can be stored, displayed, output to another computer process, and so forth. It will be understood that while the medium 106 is depicted in FIG. 1 as having a generally rectangular cross section, this is not strictly required and any shape of medium 106 may be employed provided that enough information about the surface of the medium is available to permit inferences about the target surface based on thickness measurements. For example, a lens of the sensor 112 may be immersed in the attenuation medium, such that thickness measurements are made directly from a surface of the lens to the object 108. In another aspect, the object 108 may be immersed in a bath of the medium 106 where a top surface of the bath has a known position such that thickness can be projected (based upon directionality) from this surface to the target surface.

This process may be supplemented in a number of ways. For example, a three-dimensional video may be created with a series of time-separated measurements. In another aspect, the sensor 112 or the object 108 may be moved (in a translation, a rotation, or some combination of these) in order to capture a larger area of interest or the entire object 108, or in order to obtain measurements of occluded surfaces of the object 108, or for any other reason. In such a motion-based imaging process, the relative positions of the sensor 112, the object 108, and/or the medium 106 may be physically tracked with motion sensors or the like, or the relative motion may be inferred using a three-dimensional registration process to spatially relate successive three-dimensional data sets to one another. Regardless of the particular methodology, it will be readily appreciated that individual spatial measurements, or groups of spatial measurements, may be combined to form a larger three-dimensional model, and all such techniques that would be apparent to one of ordinary skill in the art for creating a three-dimensional reconstruction are intended to fall within the scope of this disclosure.

In another aspect, the computer 116 may provide a user interface for control and operation of the system 100, as well as tools for displaying thickness measurements, displaying or manipulating reconstructed three-dimensional models, and so forth.

The computer 116 may also support calibration of the system 100 in order to correct for, e.g., variations in the sensor 112, the excitation source 102, and related optics, or variations in concentration of additives to the medium that absorb, scatter, attenuate, fluoresce, or otherwise impart various optical properties to the medium. For example and without limitation, it will be understood that one can characterize the sensor 112 using a calibration fixture or the like, prior to employing the sensor 112 in the system 100. Additionally, it will be understood that by taking controlled measurements of the absorption spectrum or the emission spectrum for the medium 106 it may be possible to improve the accuracy of the thickness measurements and related calculations. Calibration may, for example, include the use of an object 108 having a known shape and a known position within the medium 106, or the use of a container for the medium having a known shape. A variety of suitable calibration techniques will be readily appreciated based upon the use of known shapes, dimensions, surface patterns, and so forth, any of which may be adapted to use with the imaging systems described herein.

A supply 122 of the medium 106 may be provided and adapted to distribute the medium 106 between the sensor 112 and the target surface 110. It will be understood that, while the supply 122 is depicted as an external reservoir, the supply should more broadly be understood as any structures that deliver the medium 106 and/or retains the medium 106 about the object 108 in a manner that permits thickness measurements including any pumps, valves, containers, drains, tubing, and the like consistent with supplying the medium 106 for the uses described herein.

Figure 2:
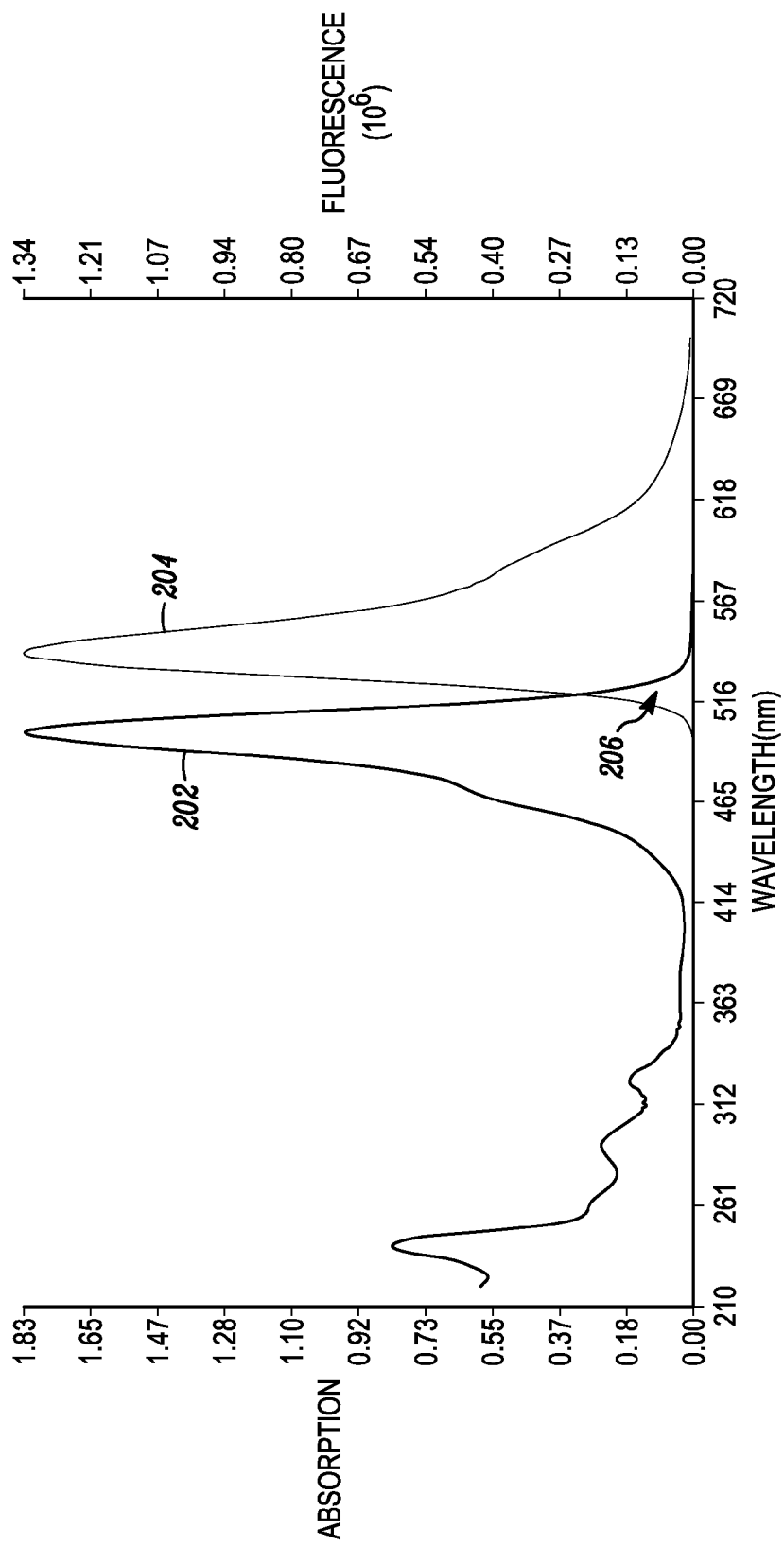
FIG. 2 shows the emission and absorption spectra for fluorescein sodium.

FIG. 2 shows the emission and absorption spectra for fluorescein sodium. In general, the imaging techniques described above may employ known ERLIF techniques using two different fluorescent dyes. However, in one aspect the imaging system may instead be implemented using a medium that contains a single fluorescent dye (or other substance) such as fluorescein sodium that has an absorption spectrum 202 that overlaps with an emission spectrum 204. By exciting this dye with a blue light and capturing fluorescent image pairs in ten nanometer bands within the overlapping spectrum 206 of non-zero absorption and attenuation, such as centered on about 510 nanometers and about 540 nanometers, intensity values can be obtained for thickness calculations in a manner similar to the ERLIF techniques noted above. Thus in one embodiment there is disclosed herein a thickness measurement and/or three-dimensional imaging system that uses a medium with a single fluorescent dye, wherein the dye has overlapping, non-zero emission and absorption spectra.

Figure 3:
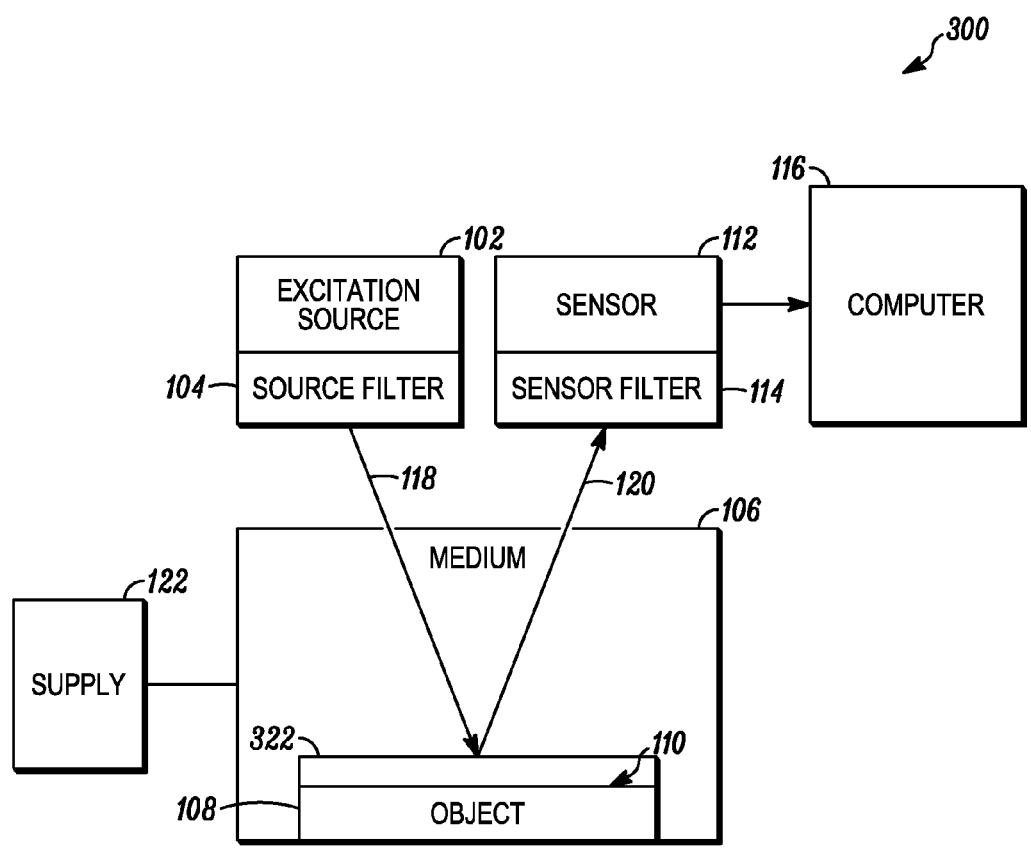
FIG. 3 shows a three-dimensional imaging system using a luminescent surface applied to an object.

FIG. 3 shows a three-dimensional imaging system using a luminescent surface applied to an object. In general, the system 300 may be as described above with reference to FIG. 1 with differences as noted below. A luminescent layer 322 may be applied to the target surface 110 of the object 108, and may emit light at a first wavelength and a second wavelength that can be measured by the sensor 112 in order to facilitate calculations of thickness of the medium 106. In general, the sensor 112 may be positioned to capture an intensity of the first wavelength and the second wavelength in a direction of a location on the target surface 110, and a processor such as the computer 116 may be programmed to calculate a thickness of the medium in the direction of the location based upon a function of the intensity of the first and second wavelengths.

In one aspect, a luminescent layer 322 is applied to the target surface 110 or embedded within the object 108 (such as using a waveguide or the like). Emissions from the luminescent layer 322 may travel along the optical return path 120 as described above. Although the following description refers explicitly to a layer of luminescent material, it will be readily understood that the object 108 may also or instead be fabricated from a luminescent material to achieve a similar effect, or may contain waveguides or the like that luminesce. Thus as used herein the term "luminescent layer" should not be interpreted as requiring a discrete layer of luminescent material on the target surface 110 of the object 108. Rather any technique for rendering the object 108 luminescent should be understood as creating the luminescent layer 322 as that term is used herein unless a different meaning is explicitly stated or otherwise clear from the context. In general, the luminescent layer 322 may be formed of any suitable combination of materials selected for appropriate mechanical properties, optical properties, and other properties.

Mechanical properties of the luminescent layer 322 may depend on the manner in which the luminescent layer 322 is to be applied. For example, an oil or other relatively viscous material may be appropriate for dip coating the object 108, while a less viscous fluid might be usefully employed for spraying or painting onto the target surface 110. In other embodiments, a thin film or other membrane may be impregnated with a luminescent material (or fabricated from a luminescent material, or coated with a luminescent material) and be used to form the luminescent layer 322 in an inflatable membrane as described below. The membrane may be elastic, deformable, flexible, pliable, or any combination of these, or have any other properties useful for forming a conforming, luminescent layer over the object 108.

In embodiments, the luminescent layer 322 may be a membrane that can be wrapped around some or all of the object 108. The object 108, enclosed in the luminescent layer 322 may then be introduced into the medium 106 and thickness measurements may be obtained from any number of poses from within or outside of the medium 106. Thus for example, where the object 108 is a human foot, a sock may be fashioned of a material with the luminescent layer 322 disposed on an outside of the sock. A foot may then be inserted into the sock, which may in turn be placed into the medium 106 to obtain a three-dimensional model of the foot. This approach may more generally be employed to obtain three-dimensional images using a membrane such as any of the elastic or inelastic membranes described herein as an exterior enclosure for a target surface. Thus in one embodiment there is disclosed herein a sock (or other enclosing membrane) with a luminescent exterior surface, which may be used for capturing three-dimensional images of an object inserted into the sock.

Optical properties of the luminescent layer 322 may be controlled by the introduction of suitable additives. The luminescent layer 322 may include a fluorescent dye or other radiant substance that responds to illumination from the excitation source 102. One suitable fluorescent substance may include coumarin-153, which is a powder that can dissolve and/or spread very well in certain plastics, has suitable fluorescent properties, and appears to be non-toxic. In another aspect, the luminescent layer 322 may contain a chemiluminescent or electroluminescent material that serves as a direct source of light. Suitable chemiluminescent materials may include a solution with hydrogen peroxide in the presence of a catalyst (e.g., iron or copper), cyalume in a solution with hydrogen peroxide in the presence of a catalyst (e.g., sodium salicylate), and so on. It will be appreciated that a variety of liquid-phase and gas-phase chemiluminescent compositions of matter may be employed. Suitable electroluminescent materials may, for example include powder zinc sulfide doped with copper or silver, thin film zinc sulfide doped with manganese, and so on. More generally, a variety of chemiluminescent and electroluminescent materials are known and may be adapted to use as a luminescent layer 322 as described herein. Thus, the luminescent layer 322 may include a chemiluminescent layer, an electroluminescent layer, a fluorescent layer, or some combination of these.

In alternate embodiments, the luminescent layer 322 may include an optical waveguide on the target surface 110 or within the object 108. It will be understood that a variety of geometries, mode structures, and materials for the optical waveguide are possible and may be adapted to use with the systems described herein.

The excitation source 102 may provide one or more wavelengths of light to excite a fluorescent dye or the like within the luminescent layer 322. In other embodiments, the excitation source 102 may be entirely omitted, or may be alternatively realized as a chemical, electrical, or other source of energy that produces illumination from the luminescent layer 322. In embodiments, the excitation source 102 may include an electrical power source that directly powers a waveguide in the object 108. In other embodiments, the excitation source 102 may include an electrical field, chemical precursor, or other means for illuminating the luminescent layer 322.

Thus it will be appreciated that the luminescent layer 322 may be formed of a variety of different carriers and additives. In embodiments, the luminescent layer 322 may contain any suitable luminescent pigment, such as a fluorescent dye in a liquid carrier that can be sprayed or painted onto the object 108, or a film or membrane that is coated or impregnated with a fluorescent material. For in vivo imaging, the luminescent layer 322 may be formed of biocompatible substances. In embodiments, the luminescent layer 322 may include biocompatible fluorescent metal oxide nanoparticles (and coatings containing same), thin film flexible electroluminescent sources, or nanoparticles with a surface coating of chemiluminescent molecules.

In embodiments with a luminescent layer 322, suitable intensity measurements may be obtained for thickness calculations based upon relative attenuation of different wavelengths without the need for a fluorescent or otherwise luminescent medium 106. In order to achieve desired attenuation properties, the medium 106 may include a carrier formed of a transparent fluid in which gold nanoparticles or nanorods are uniformly distributed. Gold nanoparticles or nanorods have an absorption profile that can be tuned based on the size and shape of the nanoparticles or nanorods themselves. In embodiments, the gold nanoparticles or nanorods can be tuned to absorb more optical energy within a predetermined band of visible light wavelengths than at other wavelengths. The gold nanoparticles or nanorods may have a concentration within the carrier such that the medium 106 is transparent (i.e., maintains substantially zero attenuation) outside of the predetermined band.

It will be appreciated that disclosed herein are various means for performing the functions associated with the use of the luminescent layer 322. An applying means for applying the luminescent layer 322 to the target surface 110 may include, for example, a paint brush, a sprayer, an atomizer, or a bath of material for the luminescent layer 322 into which the target surface 110 may be dipped. A distributing means may include a supply of the medium as well as any structures for retaining the medium in a desired area around the object such as a container with side wall for a liquid, or a gas-tight chamber for retaining the medium in a gaseous form. Sensor means may include any of the sensors described herein. A processing means may include any of the computing devices or other processing hardware described herein.

Figure 4:
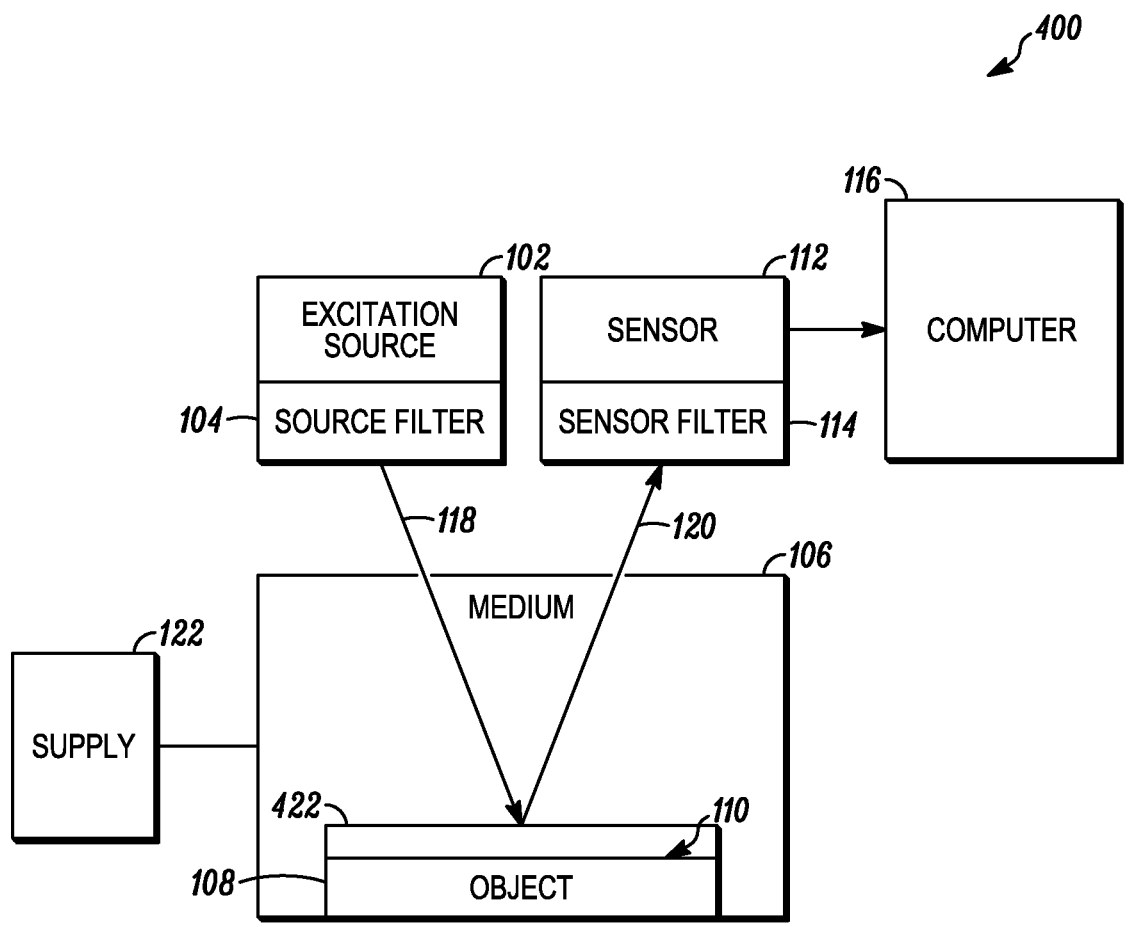
FIG. 4 shows a three-dimensional imaging system using a passive surface applied to an object.

FIG. 4 shows a three-dimensional imaging system using a passive optical layer applied to an object. In general, the system 400 is as previously described with differences as noted below. A passive layer 422 may be applied to the target surface 110 of the object 108 in order to impart the object 108 with known optical properties that can be used in combination with an attenuating medium 106 to determine thickness based upon measurements of intensity at various wavelengths.

The medium 106 may be any one or more of the attenuating media described above that provide different attenuation coefficients for at least two different wavelengths. The excitation source 102 may be a broadband light source that provides illumination of the object 108 over a range of wavelengths (or ranges of wavelengths) that includes the at least two different wavelengths used for thickness calculations.

In general, the passive layer 422 may be constructed using any of the techniques described above for a luminescent layer 322. This includes spraying, painting, or otherwise applying the passive layer 422 to the object 108, or fabricating the object 108 with an exterior surface having the desired properties. In general, the passive layer 422 imparts a known optical pattern onto the object 108 so that the object 108 has a predetermined color over a region of interest. The predetermined color may be a uniform color that is unknown, a uniform color that is a known (e.g., a specific color), or a known color distribution.

In operation, the object 108 may be illuminated by the excitation source 102, and an intensity at the at least two wavelengths may be measured by the sensor 112. By using a broadband light source and a known color distribution on the object 108, the ratio of reflected intensities can be assumed to be constant across the target surface 110. Thus any variation in the ratio of measured intensities can be correlated to a thickness of the attenuating medium 106 and a thickness can be calculated. Using a ratio may also reduce the effects on thickness calculations of any spatial non-uniformity in the illumination source or in the reflectivity of the passive layer.

In one aspect, the passive layer 422 may have a color that varies. This may be useful, for example, where the target surface 110 is expected to exhibit significant variability in height (with corresponding variability in thickness of the medium 106). In general, the sensitivity of measured intensities of light at the sensor 112 to the thickness of the medium 106 may depend on a number of factors including a color selected for the passive layer 422. Where a surface is expected to be nearly planar, high sensitivity may be preferred in order to achieve greater resolution in thickness measurements. However, where a surface is expected to be highly non-planar, lower sensitivity may be required in order to avoid saturation of the sensor 112, or more generally to provide an adequate depth of field to capture depth. Where some information is available a priori concerning the shape of the object 108 being measured, this information can be used to scale measurement resolution accordingly with a suitable, corresponding selection of color on the target surface 110.

The passive layer 422 may also or instead have other properties selected to assist in capturing accurate thickness measurements. For example, a matte finish may provide more consistent reflective properties for the target surface 110 across a range of illumination conditions. Similarly, a dark color finish may absorb certain wavelengths of incident light that would otherwise interfere with sensor measurements.

In one aspect, a system described herein for capturing thickness measurements from a target surface with a known color distribution may include a distributing means, which may be the supply 122 or any of the other means described above for distributing a medium between a target surface and a sensor or retaining the medium in this distribution. The system may include an illuminating means which may be any of the light sources or other excitation sources described above. The system may include a sensor means which may include any of the sensors described above suitable for capturing wavelength intensity data corresponding to the illumination provided by the illumination means. Finally, the system may include a processing means which may include any processor or computing device described herein programmed to calculate thickness based on wavelength intensity measurements and, where appropriate, to further reconstruct a three-dimensional image from the resulting thickness(es).

In one aspect, the systems described above advantageously permit three-dimensional imaging using a single camera such as a conventional color camera. By physically arranging a medium, illumination sources, and/or surface treatment of an object according to the various embodiments described above, thickness measurements can be obtained with a single camera and geometrically converted into a three-dimensional image of a target surface. Thus, in one aspect a three-dimensional imaging device disclosed herein includes a camera and a processor. The camera, which may be a conventional color camera, may include a lens and one or more sensors capable of capturing a two-dimensional color image of a field of view including an intensity at a first wavelength and a second wavelength, which may be any of the wavelengths or bands of wavelengths described above. The intensity at each pixel location in the two-dimensional image corresponds to a direction from the lens into the field of view so that suitable directionality for the measurement can be inferred and employed in a three-dimensional reconstruction. The processor, which may be the computer or any other processing devices described above, may then calculate a thickness of a medium in the direction corresponding to each one of the plurality of pixel locations as a function of the intensity of the first wavelength and the intensity of the second wavelength at that one of the plurality of pixel locations, thereby providing a plurality of thickness measurements. From this plurality of thickness measurements and related information such as the directionality associated with each pixel and any a priori information about the geometric boundaries of the medium, the processor may calculate a three-dimensional image of an object within the field of view.

It should be appreciated that the presently disclosed use of a single camera in obtaining a three-dimensional image can be applied in the context of conventional ERLIF technique as well.

For sensors 112, the camera may include a complementary metal oxide semiconductor (CMOS) chip camera with one or more CMOS sensors in a solid state device, or the camera may include an array of charge-coupled devices in a solid state device. The camera may include any number of filters to selectively capture the intensity of the first and second wavelengths at each one of the plurality of pixel locations. The filters may include a filter mask disposed on the imaging device (i.e., integrated into the camera chip or other solid state imaging device). For example, the camera may include a plurality of filters for selectively capturing an intensity of different wavelengths at different ones of the plurality of pixel locations, such as a conventional RGB or CMY filter mask, or a plurality of filters to selectively capture specific wavelengths used in thickness calculations. The filters may also or instead include external filter devices or systems, and may include active filters that permit adjustments to filter properties during operation or fixed filters such as dichroic mirrors or the like manually positioned in front of a camera lens.

The camera may capture RGB (red, green, blue) or CMY (cyan, magenta, yellow) color images as typically found in commercially-available hardware, or any other useful narrow or broad ranges of wavelengths. In one embodiment where the medium is a gas, the camera may be immersed in the gas along with the target surface and the thickness measurement may be an entire distance from the camera lens to a location on the surface of the object. A light source or other excitation source may also be included, all as generally described above, and the light source may include any filter or combination of filters suitable for a particular medium. Such filters may be useful, for example, to selectively pass one or more wavelengths to excite a fluorescent material, or to attenuate light in wavelengths where fluorescent light is emitted so as to avoid interference with fluorescent emissions from the target surface or the intervening medium.

In another aspect, useful mediums are disclosed for use with the imaging systems described above. In general, these mediums include any combination of carriers and other substances (for attenuation or for fluorescence) devised specifically for use with the systems above and not otherwise commercially available or described in the art.

For example, in one aspect, a composition of matter described herein includes a carrier formed of a transparent fluid medium and a plurality of gold nanoparticles uniformly distributed within the carrier. The gold nanoparticles may be advantageously tuned to absorb optical energy within a predetermined band of visible light wavelengths in order to facilitate thickness measurements and three-dimensional imaging as described herein.

The plurality of gold nanoparticles may be tuned using a shape of the plurality of gold nanoparticles and/or the plurality of gold nanoparticles may be tuned using a size of the plurality of gold nanoparticles. The plurality of gold nanoparticles may have a concentration within the carrier such that the composition has zero attenuation outside the predetermined band. The predetermined band may be between 450 nanometers and 550 nanometers. The carrier may be one or more of an oil, a gel, a gas, and a liquid, any of which might usefully be selected according to the subject matter being imaged and the imaging technique being employed. In one aspect, the carrier may include a silicon oil. In another aspect where the subject matter can be cast, or a gel might otherwise serve as a useful medium, the carrier may include a glycerol, or more generally any gelatin, glycerol, and various solutions or other formulations or preparations of same, or any other substance or combination of substances with similar properties. In other embodiments, the carrier may be curable. The carrier may include a polymer, blend of polymers, or any other curable substances that can be conformed to a target surface and then cured using, e.g., chemical curing, heat curing, light curing, time curing, and so forth. The carrier may also be biocompatible so that it can be safely used for in vivo imaging of subject matter such as human dentition or a human ear canal.

In another aspect, the medium may include a carrier formed of a transparent fluid medium and a dye that is uniformly distributed within the carrier. The dye may consist of a single fluorescent dye having an absorption spectrum over which the dye absorbs light and an emission spectrum at which the dye fluoresces, wherein the absorption spectrum and the emission spectrum have at least one overlapping non-zero region. This single-dye formulation improves upon carriers used in, e.g., conventional ERLIF by reducing to one the number of fluorescent dyes required in the medium. By adapting the imaging hardware and developing a suitable mathematical approach, the applicants have devised a technique for capturing images with a medium that contains a single fluorescent dye. Thus it should be appreciated that in this context any reference to a single dye, single fluorescent dye, single fluorescent substance, or the like is intended to refer to exactly one fluorescent substance, that is, one and only one fluorescent substance and no more than one fluorescent substance, which marks a significant departure from and improvement upon previous ERLIF imaging techniques.

The carrier may be one or more of an oil, a gel, a gas, and a liquid. For example, the carrier may include a silicon oil or a glycerol. The dye may be fluorescein sodium. The carrier may be curable, as generally discussed above, and the carrier may be biocompatible. In one embodiment, the dye may be encapsulated in silica nanoparticles. The composition may have an absorption spectrum including a peak within a visible light, which may be a local maximum or an absolute maximum. The composition may similarly have an emission spectrum including a peak within a visible light range.

Figure 5:
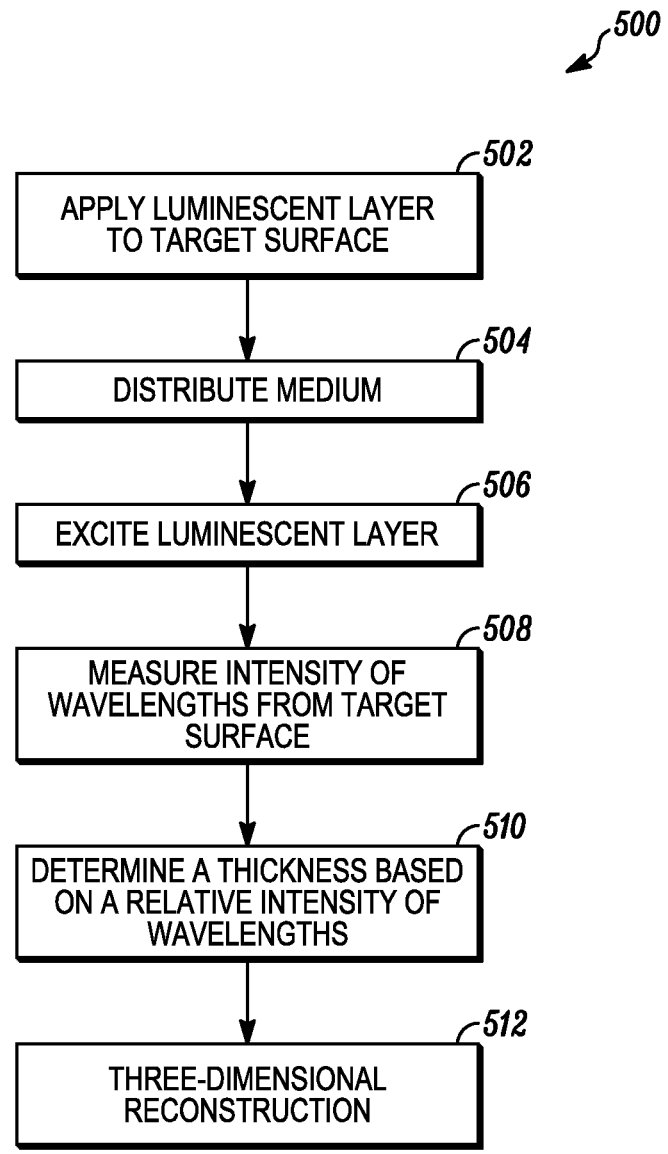
FIG. 5 is a flow chart of a method for three-dimensional imaging using a fluorescent layer applied to a target surface of an object.

FIG. 5 is a flow chart of a method for three-dimensional imaging using a luminescent layer applied to a target surface of an object.

The method 500 may begin with applying a luminescent layer to a target surface as shown in step 502. The luminescent layer, which may be a fluorescent layer, a chemiluminescent layer, an electroluminescent layer, and so forth, may be applied using any of the techniques described above including spraying, painting, dip-coating and so forth, or by fabricating the object from a fluorescent material. For example, this may include applying a fluorescent layer to the target surface as a fluorescent pigment in a liquid carrier. The luminescent layer may emit light at a first wavelength and a second wavelength, such as in response to any of the excitation sources or other stimuli described above. In other embodiments, the luminescent layer may emit light at a first wavelength, such as due to fluorescence, and reflect light at a second wavelength, where the first wavelength and the second wavelength are used to obtain thickness measurements of a surrounding medium.

As shown in step 504, the method 500 may include distributing a medium such as any of the media described above between the luminescent layer and a sensor. It will be appreciated that this may include a variety of techniques for interposing a medium between the object and the sensor, such as pouring the medium in liquid form into a container with the object, immersing the object in the medium, or supplying a gas into a chamber with the object. In another aspect, this may include inflating a balloon, bladder, or other inflatable membrane with a gas that contains a fluorescent dye, and then inserting the sensor into the inflatable membrane. In another aspect, this may include inserting an object into a sock or other enclosure before distributing the medium as described above.

In some embodiments a balloon or the like containing the medium may be pushed against, placed upon, or otherwise brought into contact with an object so that it conforms to a target surface. The interior of a balloon in this posture may be used to obtain a three-dimensional impression of the target surface against the balloon using any of the techniques described herein. Thus it will be appreciated that techniques described herein for measurement of interior cavities may also or instead be adapted to measurements of any surface. In one aspect, a device deploying the inflatable membrane may be specifically adapted to this purpose, such as by inflating a membrane within a cone (which may also form a sealed interior along with the membrane) or at the end of a supporting handle that facilitates placement of the inflatable membrane against an object.

As shown in step 506, the method 500 may include exciting the luminescent layer so that it provides some combination of reflected light and/or radiant light. As discussed above, this may include one or more wavelengths of light from an excitation source that are reflected off the target surface and/or one or more wavelengths of light radiating from the luminescent layer due to fluorescence, electroluminescence, chemiluminescence, or any other suitable mechanism so that the luminescent layer emits light as described in step 502. The luminescent layer may include a fluorescent layer that emits light at the first wavelength and the second wavelength in response to an excitation light source, so that exciting the luminescent layer as described herein includes exciting the fluorescent layer with the excitation light source to provide a fluorescent emission from the fluorescent layer. The luminescent layer may be excited with an excitation source such as a broadband light source or any other light source that provides light at one or more wavelengths other than the first wavelength and the second wavelength. The excitation light source may also or instead include one or more lasers, one or more light emitting diodes, an incandescent lamp, and so forth. In another aspect, a waveguide may be built into the object or target surface and serve directly as the luminescent layer.

As shown in step 508, the method 500 may include measuring an intensity of the first wavelength and an intensity of the second wavelength in a direction of a location on the target surface with the sensor, which may for example be any of the sensors described above.

As shown in step 510, the method 500 may include determining a thickness of the medium in the direction of the location based upon a function of the intensity of the first wavelength and the intensity of the second wavelength. It will be understood that the actual relationship between wavelength intensities and thickness may depend on a variety of factors such as the nature of the luminescent layer, the coefficient of attenuation of various wavelengths by the medium, an intensity of the excitation source, and so forth. Where the sensor provides measurements from a plurality of pixel locations (corresponding to a plurality of locations on the target surface), a two-dimensional array of such intensity measurements may be used to obtain a two-dimensional array of thickness calculations.

A more detailed analytical development of calculating or determining thickness using a fluorescent surface is now provided. The fluorescence characteristics of a target surface and the characteristics of the absorbing medium may be chosen so that a part of the fluorescence spectrum is absorbed more than other parts of the fluorescence spectrum. For example, where two intensity bands (also referred to herein simply as intensities) centered on wavelengths $\lambda_1$ and $\lambda_2$ are measured, the medium's absorptivity coefficients $\epsilon_{\lambda,1}$ and $\epsilon_{\lambda,2}$ should be different. Where a band centered around $\lambda_1$ is the preferentially absorbed band, then $\epsilon_{\lambda,1} > \epsilon_{\lambda,2}$. The normalized measured intensities of both wavelength bands traveling from the fluorescent surface to an image sensor located a distance d within the medium (or d through the medium for a sensor outside the medium) and away from the surface may be described by the following equations:

$$\overline{I_{\lambda 1}}(d) = \frac{I_{\lambda 1}(d)}{I_{\lambda 1, x=0}} = e^{-\varepsilon_{\lambda 1} Cd} \qquad [\text{Eq. 1}]$$

$$\overline{I_{\lambda 2}}(d) = \frac{I_{\lambda 2}(d)}{I_{\lambda 2, x=0}} = e^{-\varepsilon_{\lambda 2} Cd} \qquad [\text{Eq. 2}]$$

The intensity of the bands at the fluorescent surface, $I_{\lambda 1,x}=0$ and $I_{\lambda 2,x}=0$, is dependent purely on the fluorescence properties of the surface and the spectrum and intensity of the excitation illumination. Though variations in excitation intensity may change the intensity of the fluorescence at the surface, any change in the ratio of $I_{\lambda 1,x}=0$ and $I_{\lambda 2,x}=0$ will be negligible. Therefore, one can take the ratio of the normalized intensities from [Eq. 1] and [Eq. 2] above and obtain an expression that is solely dependent on depth and the concentration and absorption coefficients of the medium:

$$I_{Ratio}(d) = \frac{\overline{I_{\lambda 1}}(d)}{\overline{I_{\lambda 2}}(d)} = e^{[(\varepsilon_{\lambda 2} - \varepsilon_{\lambda 1}) Cd]} \qquad [\text{Eq. 3}]$$

Conspicuously, the intensity ratio decreases exponentially as the distance through the medium increases. This relationship permits a calculation of thickness through the medium. It will be appreciated that in practice, actual measurements may be obtained and fit to this relationship using any suitable techniques in order to provide calibrated thickness measurements from a working system.

As shown in step 512, the method 500 may include reconstructing a three-dimensional image of the target surface. This may include, for example constructing a three-dimensional image of the region of interest with a plurality of measurements from the sensor using any of a variety of geometric constraints along with thicknesses of the medium as calculated from intensity measurements. The geometric constraints may for example include any spatial information about boundaries of the medium, such as at least one known surface of the medium that can be combined with one or more thickness measurements (and a direction for same) to derive a surface point on the target surface. It will be appreciated that the at least one known surface may be any of a variety of surfaces in the various embodiments discussed herein where spatial information about the surface (or more specifically, the surface-medium boundary) is known. Thus for example, a known surface may be an exposed top surface of a tank that contains the medium in a liquid form, or an interior side surface or bottom surface of a transparent container of the medium. The known surface may also or instead include a camera lens or other optical element that separates sensors from a gaseous medium. More generally, any spatial boundary of the medium that is known or can be measured may serve as the at least one known surface used in three-dimensional reconstruction as described in the various methods and systems herein. In addition, any number of three-dimensional images may be combined through registration or the like to form a composite three-dimensional image of some or all of the target surface.

It will be understood that numerous variations to the above method 500 are possible, including variations adapted to particular imaging techniques. For example, where a gas is used as a medium, the method 500 may include providing a transparent barrier between the target surface and the sensor to retain the gas against the target surface. For example, the object may be placed in a transparent, gas-tight chamber and filled with a fluorescent gas. By using thickness measurements taken from outside of the chamber, along with information about the interior dimensions of the chamber, a three-dimensional reconstruction of a target surface on the object may be obtained as generally described above. In another aspect, the method 500 may include immersing the target surface in a liquid and positioning the sensor above a top surface of the liquid for capturing light intensity measurements. In such embodiments, the position of the top surface of the liquid may be readily determined and used as a basis for converting thickness measurements into a three-dimensional reconstruction.

More generally, it will be appreciated that the method 500 described above is set forth by way of example and not of limitation. Numerous variations, additions, omissions, and other modifications will be apparent to one of ordinary skill in the art, and all such modifications are intended to fall within the scope of this disclosure. In addition, the order or presentation of these steps in the description and drawings is not intended to require this order of performing the recited steps unless a particular order is expressly required or otherwise clear from the context.

Thus for example, a luminescent layer may be applied to a target before or after a medium is distributed between the target and a sensor, depending upon the manner in which this layer is applied. As another example, the medium may be distributed between a target and sensor, or the target may be immersed in a tank of the medium in liquid form, which achieves the same purpose of placing the medium against the surface for purposes of accurate thickness measurements. As another example, this may include inserting a camera into a container of liquid with the target, in which case a thickness measurement may begin at the camera lens. As another example, this may include providing other boundary information for the medium, such as a liquid surface location, a transparent barrier location through which the medium may be measured, and so forth. As another example, exciting the luminescent layer may include activating a luminescent layer on the surface through fluorescence, phosphorescence, electroluminescence, chemiluminescence, and so forth.

Figure 6:
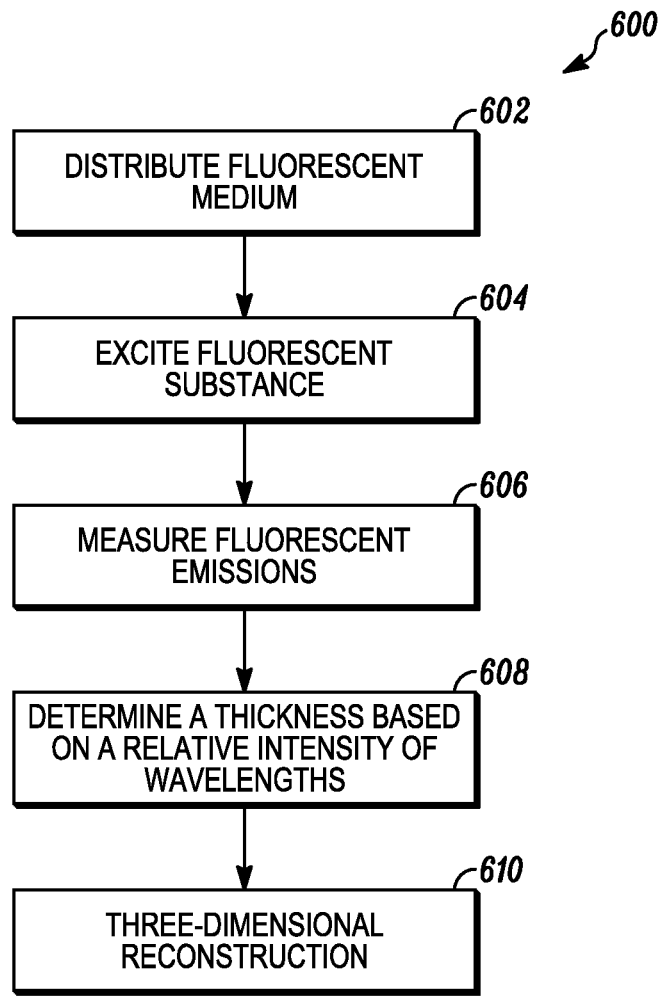
FIG. 6 is a flow chart of a method for three-dimensional imaging using a single fluorescent dye.

FIG. 6 is a flow chart of a method for three-dimensional imaging using a single fluorescent dye.

As shown in step 602, the method 600 may include distributing a medium between a target surface and a sensor, the medium including a single fluorescent substance having a fluorescence emission spectrum that overlaps in wavelength with a non-zero absorption spectrum of the medium. The medium may, for example, have zero absorption at the second wavelength. The single fluorescent substance may be fluorescein sodium, which has emission and absorption spectra as illustrated above. Using this or a similar fluorescent substance, the first wavelength may be about 510 nanometers and the second wavelength may be about 540 nanometers. In another embodiment, the single fluorescent substance may include quantum dots or other scintillants that radiate in response to incident electromagnetic radiation. In various embodiments, the medium may include a liquid, a gas, a solid, and/or a gel, with suitable adaptations to the associated hardware. For example, where the medium is a gas, the method 600 may include providing a transparent barrier or other enclosure as described above. Where the medium is a liquid, the method 600 may include immersing the target surface in the liquid and positioning the sensor above the liquid.

As shown in step 604, the method 600 may include exciting the single fluorescent substance to provide a fluorescent emission, such as by directing a broadband light source or a light emitting diode(s) toward the fluorescent dye and/or in the direction of the target surface.

As shown in step 606, the method 600 may include measuring the fluorescent emission with the sensor in a direction of a location on the target surface, including measuring an intensity at a first wavelength and an intensity at a second wavelength, wherein the medium has a different coefficient of attenuation for the first wavelength and the second wavelength. Where a conventional camera or other sensor device having a two-dimensional pixel array is employed, measuring the fluorescent emission may include measuring the intensity of the first wavelength and the intensity of the second wavelength from a plurality of locations on the target surface at a corresponding plurality of pixel locations within the sensor, thereby providing a two-dimensional array of thickness measurements.

As shown in step 608, the method 600 may include determining a thickness of the medium in the direction of the location based upon a function of the intensity of the first wavelength and the intensity of the second wavelength. This may include, for example, calculating a ratio of the intensity of the first wavelength to the intensity of the second wavelength.

For the case where three-dimensional imaging is performed using a medium containing a fluorescent substance whose absorption and emission spectra overlap, thickness can be measured by taking the intensity ratio of two fluorescent bands centered around wavelengths $\lambda_1$ and $\lambda_2$, so long as the medium self-reabsorbs one of the fluorescent bands preferentially over the other. Supposing that only the band centered around $\lambda_1$ undergoes self-reabsorption, then $\epsilon_{\lambda 1}$ is some finite positive value and $\epsilon_{\lambda 2} \approx 0$.

At any point a distance x from the sensor (or a distance x into the medium), the excitation illumination intensity $I_e(x)$ is given by:

$$I_e(x) = I_o e^{-\lambda_e C x} \quad [\text{Eq. 4}]$$

where $I_o = I_e(0)$ is the excitation intensity at the sensor location and $\epsilon_{\lambda e}$ is the absorption coefficient of the medium at the excitation wavelength $\lambda_e$.

The fluorescent emissions contributed by a differential element within the medium in the two bands centered around wavelengths $\lambda_1$ and $\lambda_2$ are given by:

$$dI_{f1} = I_e(x)\epsilon_{\lambda e} C \Phi \eta_1 dx \quad [\text{Eq. 5}]$$

$$dI_{f2} = I_e(x)\epsilon_{\lambda e} C \Phi \eta_2 dx \quad [\text{Eq. 6}]$$

where $\Phi$ is the medium's quantum efficiency, or ratio of the energy emitted to the energy absorbed, and $\eta_1$ and $\eta_2$ are the relative emissions of the medium at the two wavelengths $\lambda_1$ and $\lambda_2$. If $\epsilon_{\lambda 1} > 0$ and $\epsilon_{\lambda 2} \approx 0$, the first wavelength band will undergo absorption while the second band will not. Where the excitation illumination intensity is much greater than any fluorescent emission, any intensity increase in both the reabsorbed and the non-reabsorbed wavelength bands can be neglected. Consequently, the differential fluorescence intensity equations including the reabsorption of the $\lambda_1$ band can be written as:

$$dI_{f1} = I_o e^{-\epsilon_{\lambda e} C x} \epsilon_{\lambda e} C \Phi \eta_1 e^{-\lambda_1 C x} dx \quad [\text{Eq. 7}]$$

$$dI_{f2} = I_o e^{-\epsilon_{\lambda e} C x} \epsilon_{\lambda e} C \Phi \eta_2 dx \quad [\text{Eq. 8}]$$

To calculate the fluorescent intensities a distance d from the sensor (or through the medium in a particular direction from the sensor, these equations may be integrated from x=0 to x=d:

$$I_{f1}(d) = \frac{I_0 \epsilon_{\lambda e} \Phi \eta_1 [1 - e^{(-\epsilon_{\lambda e} - \epsilon_{\lambda 1})Cd}]}{\epsilon_{\lambda e} + \epsilon_{\lambda 1}} \quad [\text{Eq. 9}]$$

$$I_{f2}(d) = I_0 \Phi \eta_2 [1 - e^{-\epsilon_{\lambda e} Cd}] \quad [\text{Eq. 10}]$$

The ratio of the two fluorescence measurements may be taken to obtain a relationship between depth and the measured wavelengths:

$$I_{Ratio}(d) = \frac{I_{f1}(d)}{I_{f2}(d)} = \frac{\epsilon_{\lambda e} \eta_1 [1 - e^{(-\epsilon_{\lambda e} - \epsilon_{\lambda 1})Cd}]}{\eta_2 [1 - e^{-\epsilon_{\lambda e} Cd}](\epsilon_{\lambda e} + \epsilon_{\lambda 1})} \quad [\text{Eq. 11}]$$

This relationship permits a calculation of thickness through the medium. It will be appreciated that in practice, actual measurements may be obtained and fit to this relationship using any suitable techniques in order to provide calibrated thickness measurements from a working system.

As shown in step 610, the method 600 may include constructing a three-dimensional image of a region of interest with a plurality of measurements from the sensor using any of a variety of geometric constraints such as known boundaries of the medium or a container therefore along with thicknesses of the medium as calculated from intensity measurements. In addition, a number of such three-dimensional images may be combined through registration or the like to form a three-dimensional image of some or all of the target surface.

It will be appreciated that the method 600 described above is set forth by way of example and not of limitation. Numerous variations, additions, omissions, and other modifications will be apparent to one of ordinary skill in the art. In addition, the order or presentation of these steps in the description and drawings is not intended to require this order of performing the recited steps unless a particular order is expressly required or otherwise clear from the context. Thus, for example, a fluorescent or other luminescent surface may be excited before a medium is distributed between a target and a sensor, or a phosphorescent substance may be readily substituted for the fluorescent substance. All such modifications are intended to fall within the scope of this disclosure, which should be interpreted in a non-limiting sense.

Figure 7:
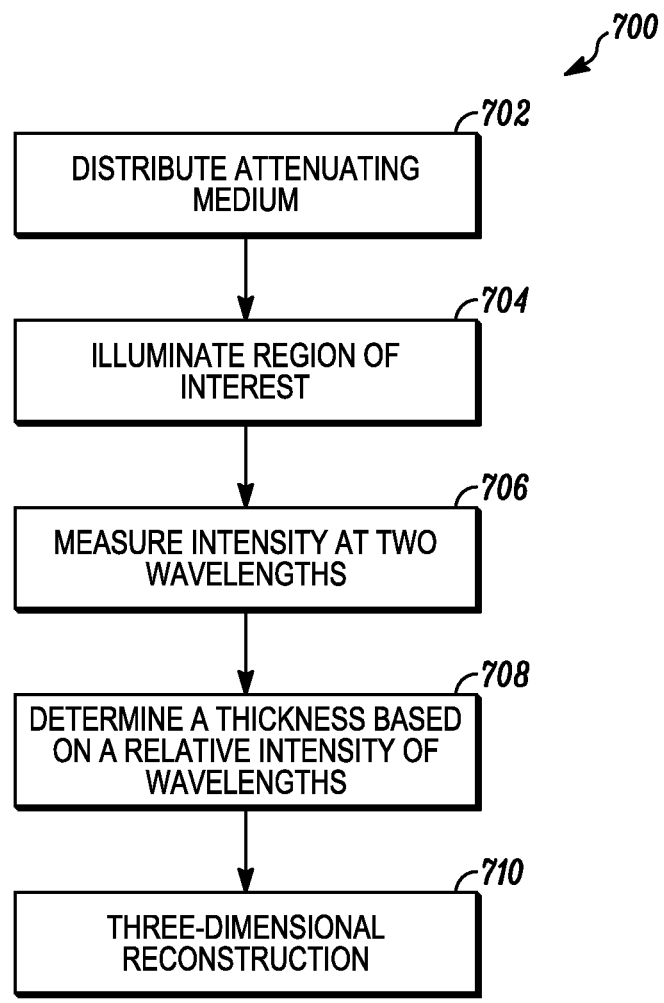
FIG. 7 is a flow chart of a method for three-dimensional imaging based upon absorption.

FIG. 7 is a flow chart of a method for three-dimensional imaging based upon absorption. In this method 700, a predetermined color on the target surface is used in combination with a broadband light source to obtain a reflection at two different wavelengths, one of which is attenuated more by an intervening medium than the other. A variety of predetermined colors may be used. For example, the color may be a specific color (e.g., blue), or the color may be unknown provided it is uniform over the target surface. In other embodiments, a known color distribution may be used, such as to provide different measurement scaling or gain.

As shown in step 702, the method 700 may begin with distributing a medium between a target surface and a sensor, the target surface having a predetermined color over a region of interest, which may be any area within a target surface of an object. The medium may be characterized by a first attenuation coefficient at a first wavelength and a second attenuation coefficient different from the first attenuation coefficient at a second wavelength. The first attenuation coefficient may be zero, or more generally any value less than the second attenuation coefficient.

The sensor may be any of the sensors described above suitable for capturing an intensity at the first wavelength and the second wavelength. In one aspect, the sensor may be a CCD array or the like that measures the intensity of the first wavelength and the intensity of the second wavelength from a plurality of locations within the region of interest at a corresponding plurality of pixel locations within the sensor, thereby providing a two-dimensional array of thickness measurements.

In one aspect, the medium may be any of the media described above, such as a solid, a liquid, a gel, or a gas. The medium may include any substance or combination of substances that results in different coefficients of attenuation at the first and second wavelengths. Where the medium is a gas, the method 700 may include providing a transparent barrier between the target surface and the sensor to retain the gas against the target surface. Where the medium is a liquid, the method 700 may include immersing the target surface in the liquid and positioning the sensor above a top surface of the liquid.

As shown in step 704, the method 700 may include illuminating a location in the region of interest, such as with a broadband light source, a laser, one or more light emitting diodes, or more generally, any excitation source capable of illuminating the location in a manner that permits a capture of reflected wavelengths at the sensor. In another aspect, illuminating the location may include illuminating with one or more of a chemiluminescent substance, an electroluminescent substance, and an optical waveguide in the target surface. Where the source of illumination is disposed on the target source or within the object, it will be appreciated that this source may itself impart the predetermined color upon which thickness calculations are based.

As shown in step 706, the method 700 may include measuring an intensity of the first wavelength and an intensity of the second wavelength in a direction of the location with the sensor. The method 700 may include filtering one or more wavelengths of light between the medium and the sensor, such as by using any of the sensor filters described above. The method 700 may also or instead include attenuating light at one or more other wavelengths for any of a variety of purposes such as filtering or shaping a broadband light source, or attenuating within the medium in order to permit additional measurements at other wavelengths that may be used to improve overall accuracy by providing additional thickness measurements at a pixel location.

As shown in step 708, the method 700 may include determining a thickness of the medium in the direction of the location based upon a function of the intensity of the first wavelength and the intensity of the second wavelength, such as by calculating a ratio of the intensity of the first wavelength to the intensity of the second wavelength and using this relationship to determine thickness. A more detailed analytical development is now provided for thickness calculations in this context.

In an absorption-based method as described herein, two intensity bands centered on wavelengths $\lambda_1$ and $\lambda_2$ may be selected where a medium's absorptivity coefficients $\epsilon_{\lambda,1}$ and $\epsilon_{\lambda,2}$ are different so that one band is preferentially absorbed over the other (or alternatively stated, a medium may be selected with differential absorptivity at desired wavelengths). The illumination source may contain the wavelengths $\lambda_1$ and $\lambda_2$, and the properties of the surface may be such that these two bands are easily reflected back towards the sensor. Provided the surface has a known, uniform color, or an otherwise known color pattern, the ratio of intensities will vary predictably with thickness of the medium.

The geometry of the sensor and the illumination source need to be considered when calculating three-dimensional geometry in this context because the wavelengths are absorbed as soon as the illumination source rays begin traveling through an absorbing medium. The simplest case involves a coaxial imaging optical train and illumination source. Here, the absorption distance traveled is simply equal to twice the distance of the sensor to the surface (or the medium boundary to the target surface), so that [Eq. 3] above becomes:

$$I_{Ratio}(d) = \frac{\overline{I_{\lambda 1}}(d)}{\overline{I_{\lambda 2}}(d)} = \frac{R_1}{R_2} e^{[(\epsilon_{\lambda 2} - \epsilon_{\lambda 1}) C \cdot 2d]} \quad [\text{Eq. 12}]$$

Here, $R_1$ and $R_2$ are the reflectivities of the surface at wavelengths $\lambda_1$ and $\lambda_2$, respectively. Because the intensity ratio decreases exponentially as the distance through a medium increases, this relationship permits a calculation of thickness through the medium. It will be appreciated that in practice, actual measurements may be obtained and fit to this relationship using any suitable techniques in order to provide calibrated thickness measurements from a working system.

As shown in step 710, the method 700 may include reconstructing a three-dimensional image of the target surface. This may include, for example, constructing a three-dimensional image of the region of interest with a two-dimensional array of thickness measurements (such as from a two-dimensional array of sensor measurements). This may further include constructing a three-dimensional image of the target surface from a plurality of three-dimensional images of a plurality of regions of interest, such as by registering or otherwise combining multiple three-dimensional images.

It will be appreciated that the method 700 described above is set forth by way of example and not of limitation. Numerous variations, additions, omissions, and other modifications will be apparent to one of ordinary skill in the art. In addition, the order or presentation of these steps in the description and drawings is not intended to require this order of performing the recited steps unless a particular order is expressly required or otherwise clear from the context. Thus, for example, a system may measure intensity through a medium at three or more different wavelengths in order to improve accuracy. As another example, the three-dimensional reconstruction may include locating one or more boundary surfaces of the medium using any number of fiducials within an imaging chamber that holds the medium. As another example, the color or color pattern of the target surface may be predetermined by capturing a color image of the target surface without an intervening medium that selectively absorbs particular wavelengths. This baseline image may provide the predetermined color pattern needed for subsequent thickness calculations once a selectively-absorbing medium is introduced between the target surface and a sensor. The color image may, for example, be captured from the same sensor(s) used to capture intensity data for thickness calculations, or from a separate color camera or the like. All such modifications are intended to fall within the scope of this disclosure, which should be interpreted in a non-limiting sense.

Figure 8:
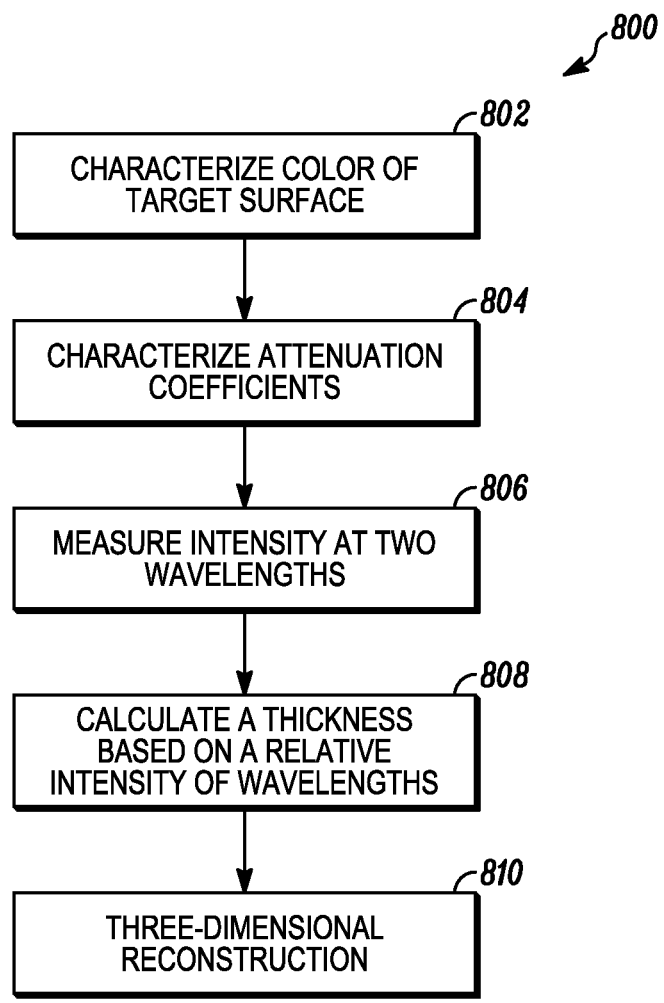
FIG. 8 illustrates a computer-implemented method for three-dimensional imaging using the technique described above.

FIG. 8 illustrates a computer-implemented method for three-dimensional imaging using the technique described above. The method 800 may be implemented, for example, as a computer program product embodied in a computer-readable medium that when executing on one or more computing devices performs the recited steps.

As shown in step 802, the method 800 may begin by characterizing a color over a region of interest on a target surface to provide a predetermined color for the region of interest. In order to perform thickness calculations as described in this embodiment, calculations exploit a known color of the target surface (or more specifically, a known reflectance at two or more specific wavelengths, although these two somewhat different notions are treated as the same for the purposes of this description). Where the target surface has a known, uniform color, the predetermined color may be characterized in computer memory as one or more scalar values that describe the color for the entire target surface (e.g., with a specific wavelength or RGB components of a measured color), or that describe a reflectance o the surface at two or more wavelengths where measurements are taken. Where a variable pattern or the like is used, the predetermined color may be stored as an array that characterizes the spatial distribution of the color pattern on the target surface.

As shown in step 804, the method 800 may further include characterizing a first attenuation coefficient at a first wavelength and a second attenuation coefficient at a second wavelength of a medium distributed between the target surface and a sensor. These values are used to evaluate the (expected) attenuation of light reflected from the target surface toward the sensor so that thickness can be calculated. In general, the attenuation coefficients may be assumed based upon the medium and any substances mixed in or otherwise distributed throughout the medium, or the attenuation coefficients may be measured using any suitable techniques, such as in a calibration process or the like.

As shown in step 806, measurements may be received from the sensor, which may be any of the photosensors, pixel arrays, or other sensors described above that capture intensity in a direction of a location in the region of interest. The measurements of an intensity at the first wavelength and an intensity at the second wavelength may be provided as signals to a processor (or memory associated with a processor) for use in subsequent calculations.

As shown in step 808, the method 800 may include calculating a thickness of the medium in the direction of the location based upon a function of the intensity of the first wavelength and the intensity of the second wavelength. Suitable calculations are described above.

As shown in step 810, and as described more generally above, a three-dimensional reconstruction of the target surface may be obtained. In this reconstruction process, thickness measurements may be converted into a three-dimensional image of the target surface using, e.g., a combination of thickness measurements and associated directionality along with information about the geometry of the medium through which thickness measurements are captured. Individual three-dimensional images may also be aggregated into a composite three-dimensional image using any suitable registration techniques.

It will be appreciated that the method 800 described above is set forth by way of example and not of limitation. Numerous variations, additions, omissions, and other modifications will be apparent to one of ordinary skill in the art. In addition, the order or presentation of these steps in the description and drawings is not intended to require this order of performing the recited steps unless a particular order is expressly required or otherwise clear from the context. Thus, for example, characterizing a color of a target surface may include imaging the target surface with spectroscopic hardware that provides sufficient information on surface characteristics (without an intervening attenuating medium) to permit attenuation-based thickness measurements. In addition, the characterization of color, as well as attenuation coefficients, may be performed before, during, or after the capture of wavelength-specific intensity information. All such modifications are intended to fall within the scope of this disclosure, which should be interpreted in a non-limiting sense.

Figure 9:
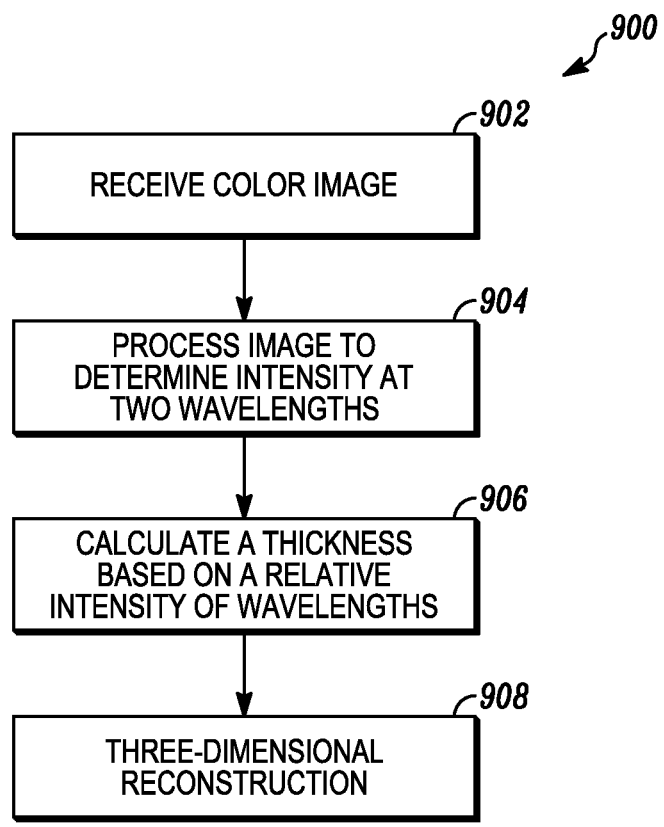
FIG. 9 shows a method for using a single camera to measure thickness.

FIG. 9 shows a method for using a single camera to measure thickness. It will be appreciated that the method 900 described with reference to FIG. 9 may be embodied in a camera and processor coupled together and operating as described, or the method 900 may be embodied in a computer program product including computer-executable code that when executing on one or more computing devices performs the recited steps.

As shown in step 902, the method 900 may begin with receiving a color image from a camera. The camera may, for example be any commercially-available color camera that provides a two-dimensional image containing intensity measurements at, e.g., a red wavelength, a green wavelength, and a blue wavelength. The camera may instead be a commercially-available color camera that provides a two-dimensional image containing intensity measurements at a cyan wavelength, a magenta wavelength, and a yellow wavelength. It will be understood that each such intensity measurement may, as a practical matter, represent an intensity across a range of wavelengths detected by the corresponding sensors, which may be relatively broad or narrow band measurements about the respective red, green, and blue center frequencies according to the filters, sensor sensitivity, and other hardware and processing characteristics of the camera. The two-dimensional image may take any number of forms, such as three arrays of pixel values for each of the red, green, and blue images.

As shown in step 904, the method 900 may include processing the color image to determine, for each one of a plurality of pixels of the camera, an intensity at a first wavelength and an intensity at a second wavelength. Where the camera provides direct measurement at the wavelengths of interest, such as through a corresponding use of filters, these values may be used directly in subsequent thickness calculations. Where the camera instead provides RGB or CMY data, the wavelengths of interest may be inferred from the discrete color values contained in the image.

As shown in step 906, the method 900 may include calculating a thickness of a medium in a direction from the camera corresponding to each one of the plurality of pixels based upon the intensity at the first wavelength and the intensity at the second wavelength, along with a known coefficient of attenuation of the medium for each of the first wavelength and the second wavelength. More generally, any of the techniques described above may be employed with a conventional color camera and suitable corresponding processing to capture thickness measurements as described herein.

As shown in step 908, the method 900 may include providing a three-dimensional reconstruction of a target surface, such as using any of the techniques described above. Step 908 may be performed by the same processor that provides thickness calculations, or the thickness data may be transferred to another process, processor, or machine that takes thickness data along with other geometric information (such as boundary information for a medium) and reconstructs a three-dimensional image of a target surface. In one embodiment, thickness calculations may be usefully integrated into a single device that contains the camera and the processor, and that provides as an output an array of thickness calculations for use, e.g., in a desktop computer that performs subsequent three-dimensional reconstruction.

It will be appreciated that the method 900 described above is set forth by way of example and not of limitation. Numerous variations, additions, omissions, and other modifications will be apparent to one of ordinary skill in the art. In addition, the order or presentation of these steps in the description and drawings is not intended to require this order of performing the recited steps unless a particular order is expressly required or otherwise clear from the context. All such modifications are intended to fall within the scope of this disclosure, which should be interpreted in a non-limiting sense.

In another aspect, a system described herein may include an imaging means such as a camera or any similar sensor or collection of sensors as described above for capturing a color image, along with a processing means including any of the processors or the like described herein that has been programmed to perform the data processing steps above.

Figure 10:
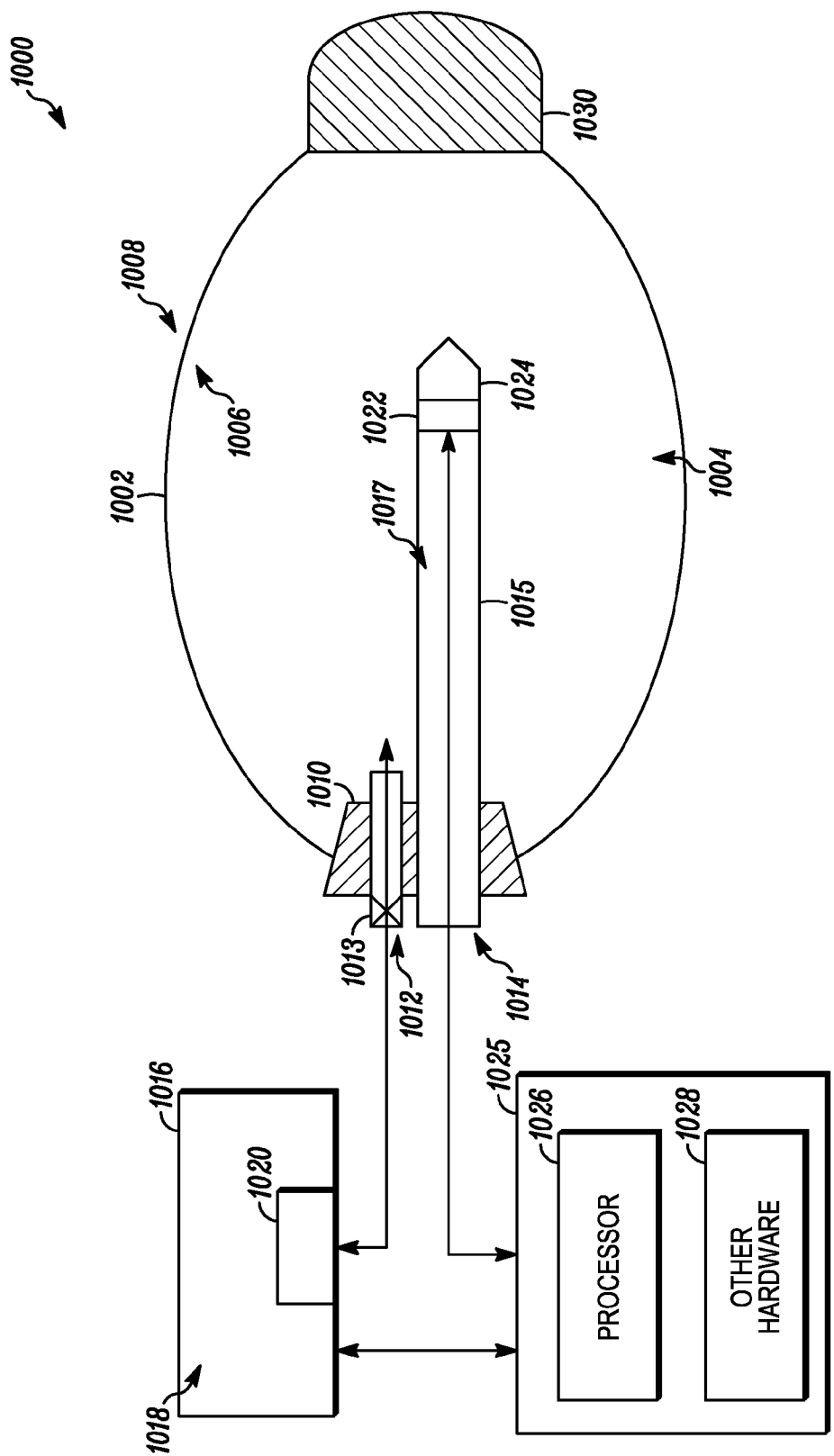
FIG. 10 illustrates an adaptation of the techniques described herein to imaging of an interior space such as a human ear canal.

FIG. 10 illustrates an adaptation of the techniques described herein to imaging of an interior space such as a human ear canal. As shown in FIG. 10, a system 1000 may include an inflatable membrane 1002 formed about an interior space 1004 with an interior surface 1006 and an exterior surface 1008, a seal 1010 having a first port 1012 and a second port 1014, a supply 1016 of a medium 1018, a pump 1020, a light source 1022, a sensor 1024, and a computer 1025 with a processor 1026 and other hardware 1028. It will be understood that, while the system 1000 may be used with any of the inventive imaging techniques described herein, the system 1000 may also or instead be adapted for use in known film thickness measurement techniques such as ERLIF or any other similar technology.

In general operation, the supply 1016 delivers the medium 1018 into the interior space 1004 of the inflatable membrane 1002 under pressure so that the inflatable membrane 1002 expands to fill an interior measurement volume (not shown). When the inflatable membrane 1002 is inflated so that it is in contact with and takes the shape of some portion of the interior measurement volume, the light source 1022 may illuminate the interior surface 1006 of the inflatable membrane 1002, and the sensor 1024 may capture intensity measurements at two or more wavelengths using any of the techniques generally described above. The resulting measurements may be received by the processor 1026 which may determine a thickness of the medium 1018 within the interior space 1004 at one or more locations on the interior surface 1006 of the inflatable membrane 1002, and these thickness measurements may be further processed to obtain a three-dimensional image of a portion of the interior surface 1006.

The inflatable membrane 1002 may be a balloon or the like formed about an interior space 1004. In general, the inflatable membrane 1002 may be an elastic membrane formed of any rubber, elastic, or other material that can be stretch to expand when filled with a pressurized gas or other material. In embodiments, the inflatable membrane 1002 may also, or instead, be any expandable membrane, elastic or inelastic, that can be pressurized or filled with material to increase an interior (and/or exterior) volume. Thus for example the inflatable membrane 1002 may be any of the membranes described above, or an inelastic membrane such as an expandable membrane formed from a number of non-porous, inelastic panels such as MYLAR films or the like. This approach permits the inflated shape of the inflatable membrane 1002 to be matched to an anticipated cavity shape or size. In another aspect, the inflatable membrane 1002 may have a substantially spherical or ovoid shape and be fabricated of a material that permits the inflatable membrane 1002 to stretch and expand to fill a cavity. It will be readily appreciated that different sized balloons and other inflatable membranes may be employed in different cavities.

The inflatable membrane 1002 may be non-porous or otherwise capable of retaining a pressurized gas or other material in an interior thereof so that it can be inflated within an interior volume and, under pressure, take the form of the interior volume. In one aspect, the inflatable membrane 1002 may be sufficiently flexible and elastic to closely follow any contours of the interior volume as it inflates therein, and sufficiently thin that a measurement of the interior surface 1006 can be used to accurately infer a shape of the exterior surface 1008 when the inflatable membrane 1002 is inflated to contact the wall of such an interior volume. More generally, any membrane capable of retaining a material within its interior space and capable of expanding to fill an interior volume in a manner that closely follows the surface contours thereof may be employed as the inflatable membrane 1002.

It will be appreciated that many variations are possible, and that any surface of the inflatable membrane 1002 may be used for imaging. For example, the inflatable membrane 1002 may be fabricated from a transparent material, and the exterior surface 1008 may be coated with a fluorescent or luminescent layer. In such embodiments, a three-dimensional reconstruction may account for the thickness of the inflatable membrane 1002 when reconstructing a target surface. In another aspect, a surface such as the interior surface 1006 may have a predetermined color such as a known, uniform color or a predetermined color distribution to permit the use of certain imaging techniques described above. In another embodiment, the cavity that is to be imaged may itself have a known color, or have a fluorescent or luminescent coating applied thereto. Such a cavity may be imaged with an inflatable membrane 1002 that is transparent and contains one of the imaging media described above, with suitable adjustments to account for the thickness of the inflatable membrane 1002 between the medium and the surface of the cavity.

A seal 1010 may be used to isolate the interior space 1004 from an ambient environment such as air at atmospheric pressure. The seal 1010 may include any number of ports such as a first port 1012 and a second port 1014 for accessing the interior space 1004. In embodiments, the seal 1010 may include an o-ring or the like, allowing for omission of the sleeve 1015. In such embodiments, a tight fit between the o-ring and the optics, electronics and so forth that are inserted through it can retain the pressurized gas (or liquid medium, or the like) within the interior space 1004.

The first port 1012 may, for example, be a fluid port having an open end within the interior space 1004 and may serve as a supply port to deliver a medium such as a gas or any of the other media described above into the interior space 1004 under pressure so that the inflatable membrane 1002 can be inflated with a medium that is used to facilitate thickness measurements. The first port 1012 may include a valve 1013 or the like to control delivery of the medium 1018 into the interior space 1004.

The second port 1014 may serve as an access port for optics, light sources, and the like that might be inserted into the interior space 1004 to capture data for thickness measurements. The second port 1014 may be coupled to a sleeve 1015 that physically contains such hardware as it is inserted into and removed from the interior space 1004. In one aspect, the sleeve 1015 may be an elastic or extendable sleeve that is coupled to the light source 1022 and/or sensor 1024 and permits the light source 1022 and/or sensor 1024 to move about within the interior space 1004 of the inflatable membrane 1002 when inflated. In another aspect, the sleeve 1015 may be a transparent, rigid shell or the like defining an access space 1017 within the inflatable membrane 1002 and physically isolated from the remainder of the interior space 1004 that is pressurized and medium-filled. In this manner an optical supply such as a fiber optic bundle or the like, lenses, filters, or other optics, sensors, light sources, electronics (e.g., for operation of the sensors and/or light sources), wires or other electrical coupling for a power supply, and so forth can be freely inserted into and removed from the interior space 1004 (or more precisely, the access space 1017 within the interior space 1004) while preserving the seal 1010 on the inflatable membrane 1002 and retaining, e.g., a pressurized gas or the like. In another aspect, the sleeve 1015 (or a window, viewport, or the like within the sleeve 1015) may be index-matched to the medium so that it has substantially the same index of refraction as the medium. This may provide a substantially undistorted optical path into the medium-filled interior space 1004.

The supply 1016 may be any reservoir, tank, or other container that holds a supply of a medium 1018, which may be any of the media described above such as a gas, liquid, gel, or the like. In general, the supply 1016 may be any supply capable of pressurized delivery of the medium 1018. In embodiments, the supply 1016 may include a pump 1020 or other device to deliver the medium 1018 through the first port 1012 and into the interior space 1004 under pressure, or similarly to withdraw the medium 1018 from the interior space 1004. The pump 1020 may be any electro-mechanical device capable of pressurized delivery of the medium 1018 including a rotary-type pump, a peristaltic pump, a reciprocating-type pump, a centrifugal pump, an eductor-jet pump, a hydraulic ram pump, and so forth. The supply 1016 may include a user control, which may be remotely activated by the computer 1025 or provided as a switch, knob, dial, or the like on the supply 1016 that electrically controls the pump 1020. In embodiments, the supply 1016 may include a plunger, lever, knob or similar device for manual application of pressure to the medium 1018, or for other mechanical delivery (also under pressure) of the medium 1018, any of which may serve as the pump 1020 as that term is used herein. More generally, the supply 1016 may be coupled to the interior space 1004 in any manner that permits selective delivery of the medium 1018 into the interior space 1004. The pump 1020 may, for example, deliver the medium 1018 with a controlled pressure, or may deliver a controlled volume of the medium 1018, or may operate according to any other suitable criteria. In another aspect, the supply 1016 may be a pressurized elastic container that contracts to deliver the medium 1018.

The light source 1022 may include any of the light sources described above. In one aspect where the inflatable membrane 1002 is rendered luminescent, the light source 1022 in the access space 1017 may be omitted. In one aspect, the light source 1022 may be shaped and sized for insertion into the access space 1017 (through the second port 1014) or otherwise positioned within the interior space 1004. In another aspect, the light source 1022 may be, e.g., a luminescent layer distributed on the interior surface 1006 or directly on a target surface of an interior cavity, or the light source 1022 may be positioned on the seal 1010 or in any other location to achieve illumination of a location on a target surface of the inflatable membrane 1002 suitable for the measurement techniques described herein.

The sensor 1024 may include any of the sensors described above. The sensor 1024 may be shaped and sized for insertion into the access space 1017 through the second port 1014, or otherwise inserted into the interior space 1004 of the inflatable membrane 1002. In one aspect, a fiberscope or boroscope may be used (either within the access space 1017 or with the sleeve 1015 attached thereto), optionally with any suitable lens such as a prism or mirrored surface with a conical, parabolic, angled, or other tip (which may also be index-matched to the medium 1018). It will be understood that in such embodiments, the sensor 1024 may have a field of view that captures measurements from a cylindrical cross-section of the interior space. This may present a significantly different geometry and different directionality for intensity measurements as compared to a conventional camera and lens, and suitable adjustments to groups of spatial measurements and any subsequent three-dimensional reconstruction may be appropriate.

In some embodiments, a transparent index-matched tip of known dimensions can be added to a fiberscope in order to improve the optical path through the medium 1018. This may allow the use of higher-absorptivity media, thus increasing the depth resolution of the system at larger distances from the tip. In other words, such a tip can shift the exponential curve that relates ratio to depth so that the relationship permits greater depth measurements.

The computer 1025 may include a processor 1026 such as any of the processors or other computing devices described above. The computer 1025 may also include other hardware 1028 such as input/output interfaces, memory, and so forth. The other hardware 1028 may in general include any hardware that operatively couples to the sensor 1024, the light source 1022, and the supply 1016. In one aspect, the other hardware 1028 may include an electronic imaging device such as optical transducers or a pixel array with inputs coupled by fiber optics to the sensor 1024. In another aspect, the other hardware 1028 may include an illumination source coupled by fiber optics to the light source 1022. In another aspect, the sensor 1024 and/or light source 1022 may be electronic devices electronically coupled to the computer 1025 with wires or the like. In another aspect, the light source 1022 and sensor 1024 may be self-powered and wirelessly coupled to the computer 1025 for control and operation of same. The computer 1025 may also be coupled to the supply 1016, and may control operation of the pump 1020 to deliver the medium 1018 to (and/or remove the medium 1018 from) the interior space 1004 of the inflatable membrane 1002.

The inflatable membrane 1002 may include a cap 1030, which may be a soft, pliable cap formed of a soft foam or similar substance. The cap 1030 may protect an insertion site such as a human ear canal during insertion of the inflatable membrane 1002, such as where the sleeve 1015 is formed of a hard material that might otherwise cause discomfort or physical damage.

It will be understood that the system 1000 may also include any of a variety of other status sensors, spatial sensors, and so forth which may cooperate with the computer 1025 to control operation of the system 1000 and monitor status thereof.

In general, the system 1000 may be adapted to use with any of the imaging techniques described above. For example, where the imaging technique uses a fluorescent layer applied to a target surface, the inflatable membrane 1002 may be adapted so that the interior surface 1006, the exterior surface 1008, or the inflatable membrane 1002 includes a fluorescent material (such as and without limitation coumarin-153) or the like. Thus in one aspect there is disclosed herein an inflatable membrane that includes a fluorescent interior surface, which membrane may be employed to capture three-dimensional images of an interior volume in which the membrane is inflated. Similarly, a predetermined or known color may be employed on the interior surface as generally described above (although additional refinements to the processing might be required where, for example, the color of the balloon changes as it expands), or the predetermined color may be on or applied to a target surface in a cavity.

The system 1000 for interior measurement may be more specifically adapted to a particular imaging context. For example, the inflatable membrane 1002 may be shaped and sized for insertion into (and inflation within) a human ear canal, or more specifically, may have a compressed (e.g., non-inflated) shape that is shaped and sized for insertion into a human ear so that the inflatable membrane 1002 may be inserted into the ear canal, inflated, and then used to capture a three-dimensional image of the ear canal. More generally, the system 1000 may be usefully employed to image biological cavities such as a bladder, stomach, ear canal, and so forth, or to image machine parts such as piston chambers, tanks, and other containers.

In one aspect there is disclosed herein a system including an inflating means, an illuminating means, a sensor means, and a processor means. The inflating means may be the supply 1016 or any other means for inflating the inflatable membrane with a medium that absorbs a first wavelength of light more than a second wavelength of light. The illuminating means may include the light source 1022 described above or any other means described herein for illuminating or otherwise exciting a surface of the inflatable membrane. The sensor means may include the sensor 1024 or any other means described herein for measuring an intensity of the first wavelength and an intensity of the second wavelength at a location on the surface when illuminated by the illuminating means. The processor means may include the processor or any other means described herein that is programmed to calculate a thickness of the medium in a direction of the location based upon a function of the intensity of the first wavelength and the intensity of the second wavelength.

In embodiments, the system 1000 may be adapted for the measurement of more general targets, not just for interior measurements or ear canals. In such embodiments, the inflatable membrane 1002 may be moved into contact with a remote object so as to conform to a surface of that object. Here, the inflatable membrane 1002 may contain or be inflated to contain the medium. For example, the inflatable membrane 1002 may include a floppy or otherwise highly-deformable bag containing the medium. Such an inflatable membrane 1002 may conform to an object so that a three-dimensional image can be obtained. This may for example be usefully employed for quality control or parts inspection, such as with turbine blades or other dimensional-sensitive parts. This approach permits three-dimensional measurements without modifications of the target object, and without exposing the target object to the medium. A variety of other uses will be readily appreciated, and are intended to fall within the scope of the present disclosure.

In some embodiments, the system 1000 may be adapted so that the inflatable membrane 1002 includes more than one chamber. Each of these chambers may be operatively coupled to its own supply 1016, each of which contains a medium having properties that are adapted based upon the expected dimensions of the part of a canal into which the inflatable membrane 1002 will ultimately be disposed. For example and without limitation, one may expect an external portion of an ear canal to be wider than an internal portion of the same ear canal. Therefore, in applications involving an ear canal, a first chamber corresponding to an external part of the ear canal might be filled with less absorptive optical media than a second chamber corresponding to an internal part of the ear canal. Such an adaptation allows the same source illumination to travel greater distances through the first chamber (where the distances are expected to be longer) than through the second chamber (where the distances are expected to be shorter). In embodiments, optical characteristics of the media may be tuned with dye composition and/or dye concentration, as well as with different fluorescent coatings for each chamber. The sleeve 1015 may pass into or through each of the chambers and preferably is index-matched to each of the media, or a separate sleeve may be provided for each chamber.

Figure 11:
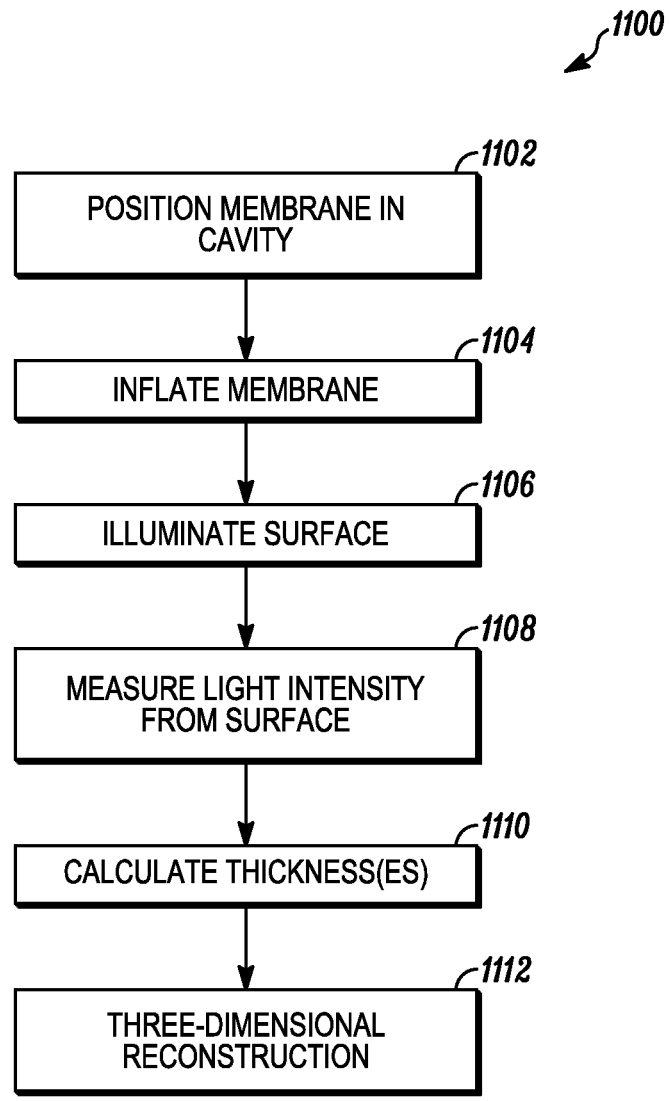
FIG. 11 is a flow chart of a method for obtaining a three-dimensional image of an interior space.

FIG. 11 is a flow chart of a method for obtaining a three-dimensional image of an interior space. In general, the method 1100 may include positioning an inflatable membrane such as any of the inflatable membranes described above within a cavity and inflating the membrane with a medium such as any of the media described above. With suitable illumination sources and image capture hardware, thickness measurements may then be taken for use in a three-dimensional reconstruction of interior walls of the cavity. The method 1100 may be implemented, for example, using the system described above.

As shown in step 1102, the method may begin with positioning an inflatable membrane in a cavity. It will be appreciated that this step may be adapted to an array of interior cavities. For example, where a biological cavity such as a stomach or bladder is being imaged, the membrane may be compressed into a shape and size that can be inserted through a natural opening (such as the throat) or through the bore of a surgical tool such as an endoscope or the like. Thus, the cavity may be a human ear canal, a stomach, a bladder, or any other biological cavity, or more generally, any of the cavities described above. It will be readily appreciated that the inflated and compressed sizes of the bladder and the desired resolution of a particular image may be considered in selecting a suitable material for the membrane, which may range from elastic materials to very thin, flexible, inelastic films such as foils and various composites. For use in imaging a human ear canal, for example, the diameter of the insertion site is relatively large compared to the cavity being imaged, and a variety of elastic materials may be suitably employed.

It will also be understood that in various techniques that use a membrane, the material selected for the membrane may depend in part upon the types of surfaces expected and the surface accuracy desired for imaging. This in some applications, detail may be important and very thin, very elastic materials may be preferably employed in order to improve surface detail. In other applications, high inflation pressure may be desired and suitably strong materials may be preferred regardless of the fidelity with which detailed surface contours are captured. In general, a wide variety of suitable membranes are known and may be adapted to different imaging applications. All such variations are intended to fall within the scope of this disclosure.

As shown in step 1104, the method 1100 may include inflating the inflatable membrane with a medium that absorbs a first wavelength of light more than a second wavelength of light. This may be, for example, any of the media described above. Inflation may be, for example with a pump or other manual or automated delivery mechanism as generally discussed above. As the inflatable membrane inflates, it may take the form of the cavity in which it is expanding, and the medium within the membrane may facilitate thickness measurements that can be used to reconstruct a three-dimensional image of the interior of the cavity.

As shown in step 1106, the method 1100 may include illuminating a surface of the inflatable membrane. This may include, for example, activating a light source such as any of the light sources described above, or chemically or electrically activating a luminescent substance within the inflatable membrane (or disposed on a surface thereof). It will be appreciated that in various embodiments described above, the illumination may be directed at another surface, such as the wall of a cavity that is being imaged (e.g., with a transparent membrane and a fluorescent cavity wall). In such embodiments, the surface of the inflatable membrane would also be illuminated regardless of the position of the illumination source, and all such variations are intended to fall within the scope of "illuminating" as that step is described here.

As shown in step 1108, the method 1100 may include measuring an intensity of the first wavelength and an intensity of the second wavelength in a direction of a location on the surface when the surface is illuminated. This may include measuring wavelength intensities using any of the sensors described above including, for example, using a conical-tipped fiberscope or the like to transmit optical signals over optical fibers to an electronic imaging device outside the membrane. In one aspect, this may include capturing measurements in a cylindrical field of view of a fiberscope.

As shown in step 1110, the method 1100 may include calculating a thickness of the medium in the direction of the location based upon a function of the intensity of the first wavelength and the intensity of the second wavelength using, e.g., any of the techniques described above according to the nature of the surface, the medium, and the like. Step 1110 may be performed by any suitable processor or other computing device or combination of computing devices.

As shown in step 1112, the method 1100 may include reconstructing a three-dimensional image of the surface based upon the thickness measurements and available boundary information for the medium. So for example where a clear plastic tube or other transparent, rigid sleeve is used for sensors and the like, the thickness measurements may be projected from the physical interface of the sleeve with the medium. Step 1112 may be performed by any suitable processor or other computing device or combination of devices.

In some embodiments, the method 1100 includes an iteration in which the inflatable membrane inflates to a first pressure and a calculation determines a first thickness of the medium, as described above. Then the inflatable membrane inflates again, this time to a second pressure, and a calculation determines a second thickness of the medium, again as described above. When the first measurement and the second measurement correspond to the same point of interest on an object, and when a plurality of such measurements are made for a plurality of points of interest on the object, the method 1100 can include a step of generating a compliance map that shows relative firmnesses of the object at the points of interest, or the manner in which a cavity yields to pressure. For example, a point of interest that shows greater change in thickness (e.g., yields to greater pressure) between the first measurement and the second measurement has more "give" than a point of interest that shows less change in thickness between the measurements. Thus, step 1112 can include or consist of calculating the compliance map and the logical flow of the method 1100 can include a loop from step 1110 back to step 1104 for any number of measurements under different pressurization.

Figure 12:
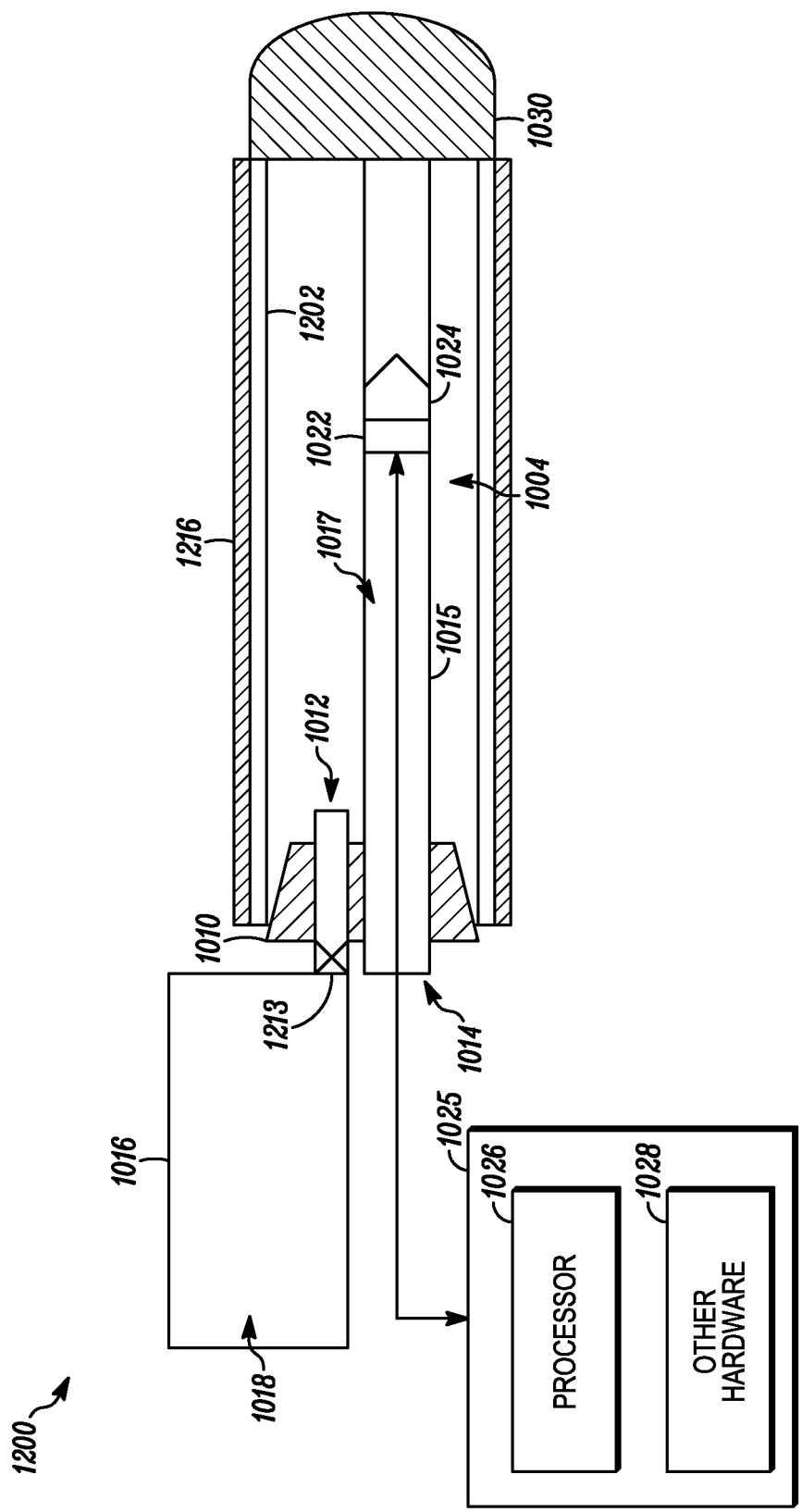
FIG. 12 shows a self-inflating bladder for use in interior measurements.

FIG. 12 shows a self-inflating bladder for use in interior measurements. In general, the self-inflating bladder 1200 may include a membrane 1202 such as a collapsible membrane including many elements of the system 1000 described above, with differences as noted below.

The membrane 1202 may be formed around an interior space 1004, and constructed of a material that returns to an original shape in an absence of external forces. For example, the membrane 1202 may be formed of a shape-memory alloy, a visco-elastic solid or foam, a photo-induced shape-memory polymer, a shape-memory rubber, or any other film, frame, lattice, composite exterior and/or interior structure or combination of structures that return to an original shape. The membrane 1202 may be shaped and sized (in its expanded form) to be larger than a cavity that is to be imaged in one or more dimensions so that the membrane 1202, when compressed into a compressed membrane, can be inserted into the cavity and then expand to contact the interior wall of the cavity. More generally in operation, the membrane 1202 may be compressed with an application of force, and then released to expand to its original shape, such as to fill a cavity for imaging. In one aspect, the membrane 1202 may be fabricated of a material that returns to an original shape under user-controlled conditions such as an application of heat, moisture, an electrical field and so forth. It will be understood that in such embodiments, the membrane 1202 will tend to return to an original shape in the absence of physical external forces along with an application of the appropriate form of activation. All such variations are intended to fall within the scope of a membrane returning to an original shape in the absence of external forces as that phrase is used herein.

It should also be understood that the compressed membrane need not have a reduced volume in order to be "compressed" as that term is used herein. For example, where a generally elastic membrane is filled with a viscous substance, the membrane may be elongated with an application of force so that it has greater length and less thickness. In this compressed state, the membrane may be inserted into a narrow passage (such as an ear canal) and the membrane may then expand to abut the walls of the passage as it returns to its original, thicker shape. Thus while a variety of embodiments discussed herein involve displacement of a medium into and out of a membrane, in other embodiments a collapsible membrane may be compressed by displacing the medium within the membrane without any overall change in volume of the membrane. In such embodiments, the membrane may be advantageously fabricated in a sealed form without any fluid port or the like for manipulating the medium within the membrane.

The interior space 1004 may be coupled to a supply 1016 of a medium 1018 (which may be any of the supplies and media described above) through the first port 1012, which in this case may be a fluid port, that couples the supply 1016 to the interior space 1004 and includes a flow restrictor 1213 or the like that controls a rate at which the medium 1018 passes between the supply 1016 and the interior space 1004. This may include, for example, a porous membrane, nozzle, narrowed fluid passage, adjustable valve (for variable control of flow rate) or any other substance or structure (or combination of these) to slow the passage of the medium 1018 into the interior space 1004 when the membrane 1202 is expanding. In general, by restricting a flow of the medium 1018, the flow restrictor 1213 limits that rate at which the membrane 1202 expands in the absence of external forces. This usefully permits the membrane 1202 to be compressed with an application of force and then released, at which point the membrane 1202 will expand slowly enough that it can be inserted into a cavity before it fully expands.

A sleeve 1015, which may be a shell such as any of the rigid shells described above, may be positioned within the interior space 1004 to define an access space 1017 for insertion of a light source 1022, sensor 1024 and the like to facilitate light intensity measurements. The sleeve 1015 may be fabricated of a transparent material, or otherwise include at least one transparent region for such measurements. The sleeve 1015 may extend from a seal 1010 to the cap 1030, which may be a soft, pliable cap such as any of the caps described above. In one aspect, the sleeve 1015 may physically connect to the cap 1030 and the seal 1010, either directly or through additional structures, to form a solid or generally rigid structure that, along with the supply 1016 and the first port 1012, can be used as an insertable imaging device. Where the self-inflating bladder 1200 is shaped and sized for use in, e.g., a human ear canal, the cap 1030 may be soft and/or pliable to protect the ear canal during insertion of the device.

The cap 1030 may include a transparent window. During insertion of the self-inflating bladder 1200 (or any other device described herein for interior imaging) into, e.g., an ear canal or other opening, a fiberscope can be inserted into the access space 1017 so that it has an optical view through the window and the sensor 1024 can capture an image down the length of the ear canal. With this view, a user may guide the self-inflating bladder 1200 (or other device) into the canal, also allowing the user to stop insertion before hitting, e.g., an eardrum or other obstruction or sensitive area. The self-inflating bladder 1220 (or other device) may include a supplemental illumination device to illuminate the canal during insertion, or the light source 1022 may be adapted to this purpose.

In one aspect a retainer 1216 may be provided that mechanically retains the collapsible membrane in a compressed shape. Thus in use, the membrane 1202 may be compressed to a size smaller than an interior diameter of the retainer 1216, which may be for example a cylindrical sleeve or the like, and the retainer 1216 may be fitted over the compressed shape to retain the membrane 1202. When a three-dimensional image is to be captured, the retainer 1216 may be removed and the self-inflating bladder 1200 may be inserted into a target cavity and permitted to slowly expand into the shape of the target cavity, with the rate of expansion determined by, e.g., the viscosity of the medium 1018, the flow restrictor 1213 positioned in the flow path, and the mechanical force applied by the membrane 1202 as it expands toward its fully expanded shape. It will be understood that the retainer 1216 may usefully be formed of a rigid material (or combination of materials) or any other material suitable for retaining the membrane 1202 in a compressed state. The retainer 1216 may be a single structure shaped and sized to slide over the cap 1030 and off the membrane 1202, or the retainer 1216 may be formed of a multi-part assembly that can be, e.g., snapped together and apart around the membrane 1202, or that hingeably encloses the membrane 1202, or otherwise removably retains the membrane 1202 in a compressed shape. The compressed shape may be shaped and/or sized for insertion into a human ear or any other cavity from which three-dimensional images are desired.

It will be understood that while FIG. 12 shows a simple, cylindrical shape for the membrane 1202 in its compressed state, any shape suitable for a particular imaging application may similarly be used, and may accommodate either the shape and size of the insertion site or the shape and size of the cavity to be imaged, or some combination of these. For example, the inner and outer portions of a human ear canal have substantially different interior diameters. Thus in one aspect, the self-inflating bladder 1200, and the membrane 1202 and retainer 1216 for same, may have a tapered shape or a two-stage shape with a relatively large diameter on an outer section for imaging the outer ear canal and a relatively smaller diameter on an inner section for imaging more deeply in the inner ear canal. Any number of similar adaptations may be made for different imaging applications, all of which will be readily appreciated by one of ordinary skill in the art.

Figure 13:
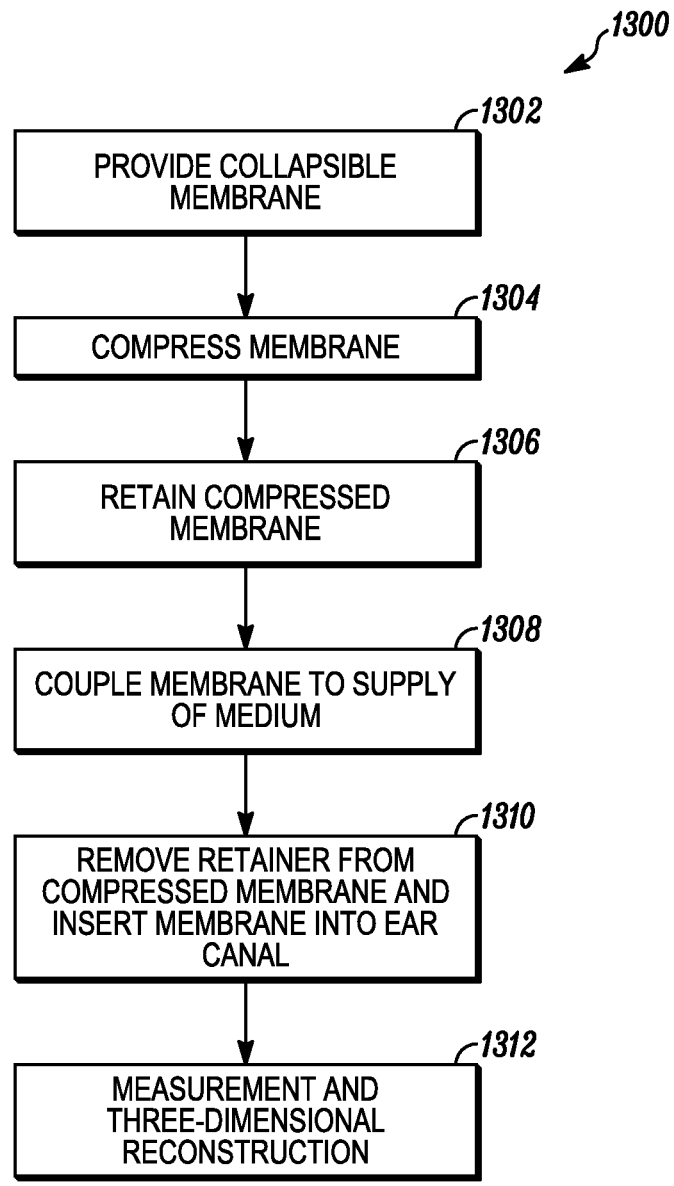
FIG. 13 is a flow chart of a method for using a self-inflating bladder to capture three-dimensional images of an interior space.

FIG. 13 is a flow chart of a method for using a self-inflating bladder such as the self-inflating bladder 1200 described above to capture three-dimensional images of an interior space, and more particular to capture three-dimensional images of a human ear canal.

As shown in step 1302, the method 1300 may begin with providing a collapsible membrane that returns to an original shape absent external forces, the collapsible membrane having an interior space. This may be, for example, any of the membranes described above. As noted above, a membrane that returns to an original shape absent external forces is intended to include any structure or combination of structures that tend to return to a shape, whether when constraining physical forces are released (e.g., a retainer as described above) or when some form of activation (light, heat, electricity, and so forth) is applied, or some combination of these.

As shown in step 1304, the method 1300 may include compressing the collapsible membrane into a shape and size for fitting into a human ear canal. This may, for example, include compressing the membrane into a generally cylindrical shape sufficiently narrow to fit into the ear canal. In one aspect, a margin of time may be provided so that, when a retainer is removed and the membrane begins to expand (as described above), the membrane does not expand beyond the expected size of the ear canal for a period of time in order to permit handling and insertion into the ear canal. This may be, for example, ten seconds, or any other duration according to user preferences or handling constraints and the like.

As shown in step 1306, the method 1300 may include retaining the collapsible membrane in the shape and size with a retainer such as any of the retainers described above. In one aspect, the collapsible membrane may be a disposable membrane with a disposable retainer. In another aspect, the collapsible membrane may be a reusable membrane, and the retainer may be removable and replaceable to permit multiple redeployments of the collapsible membrane.

As shown in step 1308, the method 1300 may include coupling the interior space to a supply of a medium in a fluid form that absorbs a first wavelength of light more than a second wavelength of light, wherein the interior space is coupled to the medium through a port that restricts a flow of the medium into the interior space, such as the fluid port and flow restrictor described above. It will be understood that in various embodiments this coupling may occur before or after the collapsible membrane is compressed and before or after the retainer is fitted to the compressed membrane.

As shown in step 1310, the method 1300 may include removing the retainer from the collapsible membrane and inserting the collapsible membrane into a human ear canal. At this point, the membrane may begin to expand and draw the medium into the interior space. As noted above, the rate at which this expansion occurs may depend on any of a number of factors such as the viscosity of the medium, the amount of flow restriction, the pressure created by the expanding membrane, and the pressurization (if any) of the supply. These factors may generally be controlled during design of the collapsible membrane, and the design may also permit manual adjustment at the time of deployment such as by providing an adjustable valve for flow restriction.

As shown in step 1312, the method 1300 may include measurement and three-dimensional reconstruction using any of the techniques described above.

It will be appreciated that the method 1300 described above is set forth by way of example and not of limitation. Numerous variations, additions, omissions, and other modifications will be apparent to one of ordinary skill in the art. In addition, the order or presentation of these steps in the description and drawings is not intended to require this order of performing the recited steps unless a particular order is expressly required or otherwise clear from the context. Thus, for example a medium may be coupled to the membrane before or after compression of the membrane. Where the medium is coupled before compression of the membrane, the supply may be used to compress the membrane using reverse pressure (e.g., suction) to extract material from the interior space. Similarly, while an ear canal is specifically mentioned, the approach may be adapted to any number of biological or other cavities. All such modifications are intended to fall within the scope of this disclosure, which should be interpreted in a non-limiting sense.

Figure 14:
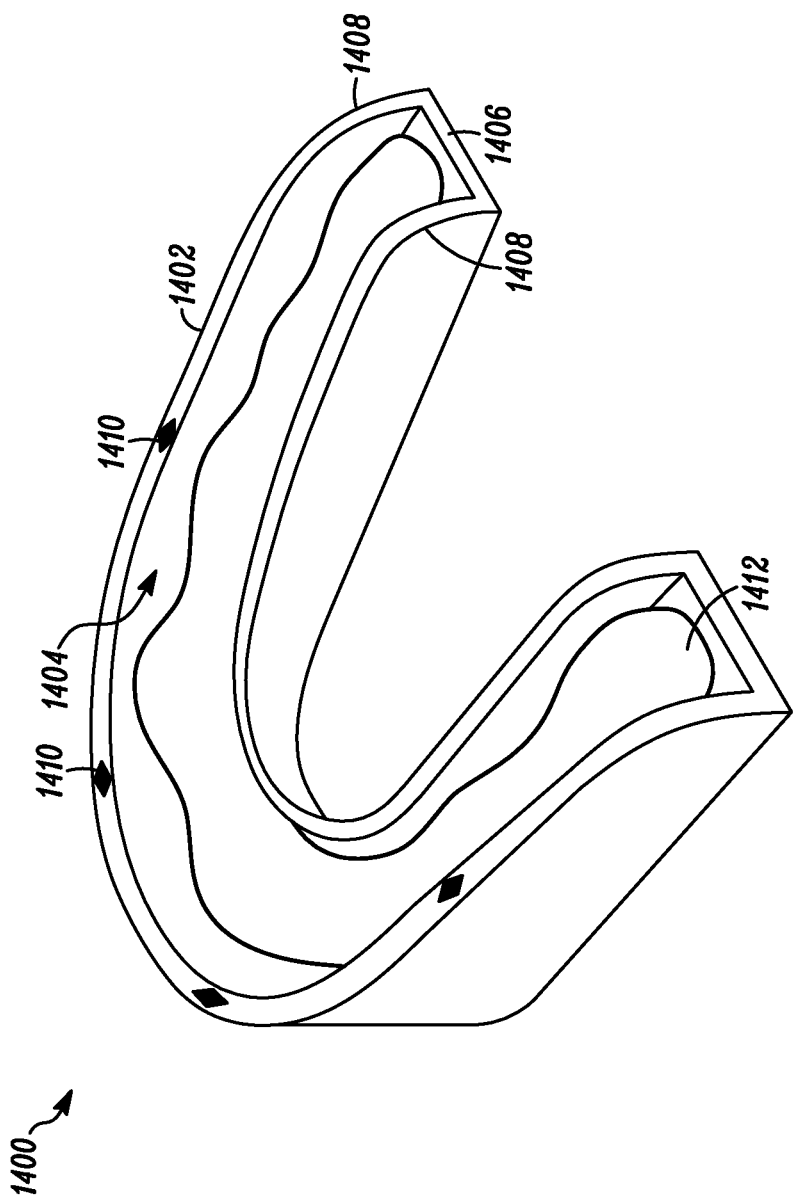
FIG. 14 illustrates an adaptation of the techniques described herein to capture a three-dimensional image of an object such as human dentition.

FIG. 14 illustrates an adaptation of the techniques described herein to capture a three-dimensional image of an object such as human dentition. In an embodiment, a device 1400 for use in imaging dentition may include an imaging tray 1402 with an interior surface 1404 formed from a bottom 1406 and one or more sidewalls 1408, and any number of fiducials 1410, along with a medium 1412 such as any of the media described above. Although not depicted, it will be understood that the device 1400 may be used with any suitable combination of the sensors, light sources, processors, and so forth described above. It will further be understood that, while the device 1400 may be used with any of the inventive imaging techniques described herein, the device 1400 may also or instead be adapted for use in known film thickness measurement techniques such as ERLIF or any other similar technology.

The imaging tray 1402 may be any container suitable for receiving an impression of an object. For dental applications, the imaging tray 1402 may be shaped and sized for use as a dental bite tray. A variety of such containers are known in the dental art including numerous disposable and/or reusable bite trays, impression trays, fluoride trays and the like, any of which may be adapted for use with the techniques described herein. In addition, while a full-arch dental tray is shown, it will be understood that the tray may instead cover any subportion of an arch such as a quadrant or a row of teeth. In other embodiments, the bite tray may capture an upper and lower arch concurrently, which may advantageously capture bite registration information relating to the alignment of an upper and lower arch. It will be appreciated that while a dental bite tray is depicted, the imaging tray 1402 may more generally have any shape and size suitable for an object that is to be imaged. In addition, the imaging tray 1402 may be adapted to any of the various imaging techniques described above. This may include, for example, fabricating the imaging tray 1402 from a transparent material so that thickness measurements can be taken through the imaging tray 1402, or fabricating the imaging tray 1402 from a fluorescent or other luminescent material so that the imaging tray 1402 can serve as a light source as described above. This may include fabricating the imaging tray 1402 from a material with a known color or a known color distribution that can be used in attenuation measurements as described above. This may also, or instead, include applying a layer to the interior surface 1404, such as a fluorescent, luminescent, or known color layer.

The interior surface 1404 may have known dimensions that can be used in combination with thickness measurements to geometrically reconstruct a three-dimensional image of an object impressed into the medium 1412. In one embodiment, the known dimensions may accommodate a dental impression in the medium 1412. More generally, geometric or spatial information about the interior surface 1404 provides boundary information for the medium 1412 within the imaging tray 1402 so that thickness measurements of the medium 1412 can be converted into spatial measurements of an impression in a common coordinate system, thus permitting a three-dimensional reconstruction. It will thus be appreciated that, while the imaging tray 1402 is depicted as having an interior surface 1404 formed of two sidewalls 1408 and a bottom 1406, the interior surface 1404 may more generally include any rectilinear, curvilinear or other surface(s) suitable for a particular object being imaged, provided that the shape of the interior surface 1404 is known in areas where boundary positions are needed for a three-dimensional reconstruction.

The bottom 1406 and sidewalls 1408 retain the medium 1412 within the imaging tray 1402 and provide known physical boundaries for one or more surfaces of the medium 1412 so that thickness measurements can be converted into a three-dimensional image. It will be appreciated that the sidewalls 1408 may be open as depicted, provided the medium 1412 is sufficiently viscous that it will remain wholly or partially within the imaging tray 1402 during handling and/or impressioning. Where for example the medium 1412 is a non-viscous liquid, the sidewalls 1408 may usefully be joined together to form a complete perimeter sidewall that retains the liquid within the imaging tray 1402. In another aspect, one or more of the bottom 1406 and sidewalls 1408 may be transparent, depending for example on the direction from which thickness measurements are expected to be taken.

Any number of fiducials 1410 may optionally be included on or within the imaging tray 1402. The fiducials may be at known locations and/or have a known shape. Each fiducial 1410 may have one or more uniquely identifying characteristics so that it can be identified in an image or other data obtained from measurements of the imaging tray 1402. Fiducials may in general serve as useful landmarks in a three-dimensional reconstruction by facilitating global registration of a number of independent three-dimensional measurements and/or images. The fiducials 1410 may, for example, provide visual landmarks to an imaging system that can be correlated to three-dimensional locations on the imaging tray 1402 or otherwise encode spatial information. More generally, the types and uses of fiducials in three-dimensional registration will be readily appreciated by those of ordinary skill in the art, and all such fiducials that might be adapted to use with the three-dimensional imaging techniques described herein are intended to fall within the scope of this disclosure. Similarly, random or regular patterns or other surface treatments can be employed to assist in registration, and may be adapted for use with the imaging tray 1402 and other devices and measurement techniques described herein.

The medium 1412 may be disposed within the interior surface 1404 and may generally include any of the media described above. In an embodiment, the medium 1040 may be capable of yielding to form an impression of an object inserted into the imaging tray and may, for example, absorb a first wavelength of light more than a second wavelength of light. The medium 1412 may include a single fluorescent dye or a plurality of fluorescent dyes. The medium 1412 may use any number of carriers.

For example, the medium 1412 may include a gel, liquid, or other substance capable of accurately retaining, or being cured to accurately retain, an impression therein. Any type of curable material (with suitable optical properties) may be used as the carrier, including materials that are heat-cured, pressure-cured, time-cured, light-cured, chemically cured, or the like, as well as any combination of these. The medium 1412 may be cured while an object is impressed therein, such as while a patient is biting into a dental bite tray, or the medium 1412 may be cured after the object is withdrawn. In the latter case, the medium 1412 is preferably sufficiently viscous to retain a useful impression of the object until the medium 1412 can be cured. In other embodiments, the medium 1412 may not be curable, but may be sufficiently viscous or plastic to retain an accurate impression after an object is removed, either permanently, semi-permanently, or at least long enough to obtain light intensity measurements for thickness calculations. In other embodiments, the medium 1412 and imaging tray 1402 may be imaged while the object is embedded in the medium. Where the object fits entirely into the imaging tray 1402, the imaging tray 1402 may be a simple desktop tray filled with liquid or the like. Where the object is physically coupled to a larger object (such as human dentition), the imaging tray 1402 may be transparent so that measurements for thickness calculations can be obtained through the bottom 1406 or sidewall(s) 1408.

Figure 15:
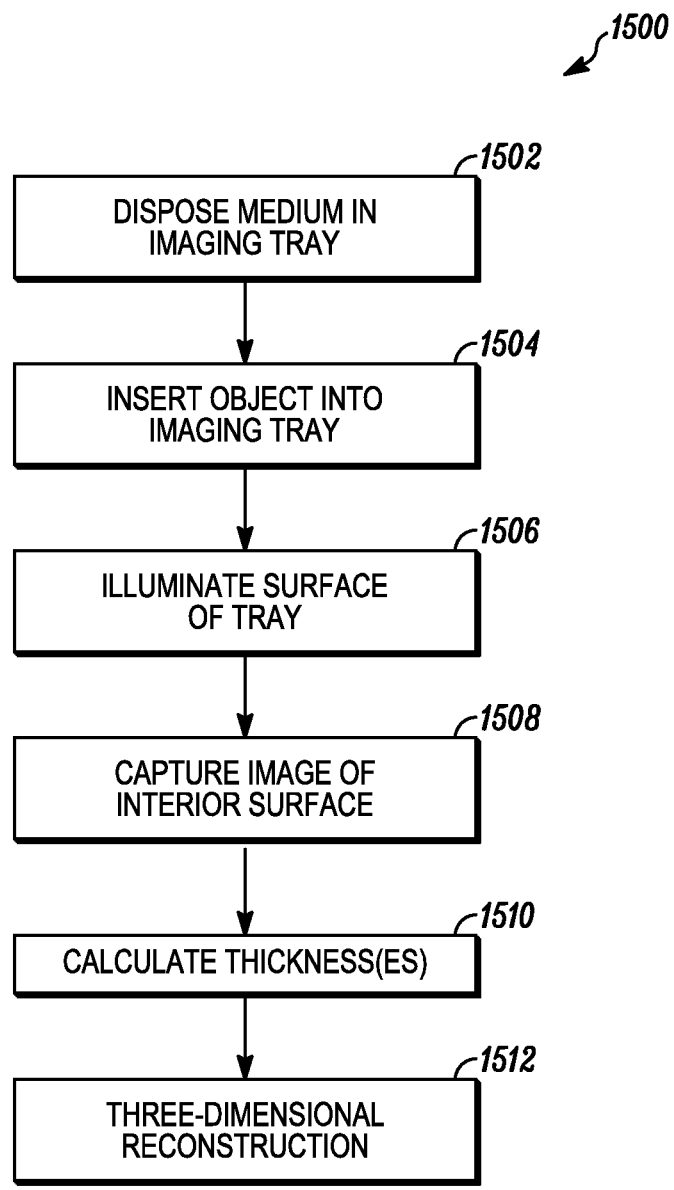
FIG. 15 is a flow chart of a method for capturing a three-dimensional image of an object such as human dentition using the techniques described herein.

FIG. 15 is a flow chart of a method for capturing a three-dimensional image of an object such as human dentition using the techniques described herein. The method 1500 may be used, for example, with the imaging tray 1402 and medium 1412 described above.

As shown in step 1502, the method 1500 may begin with disposing a medium within an imaging tray having an interior surface of known dimensions, the medium capable of yielding to form an impression of an object inserted into the imaging tray, and the medium absorbing a first wavelength of light more than a second wavelength of light. In general, this may include any of the imaging trays and mediums described above. In order to dispose the medium within the imaging tray, the medium may be poured, injected, spread, or otherwise distributed into the interior space using any suitable tools and/or techniques for the viscosity and other physical properties of the medium. In a prepackaged embodiment, the medium may be disposed within the imaging tray during fabrication, and packaged for shipment in a ready to use form. In another embodiment, the medium may be manually disposed within the imaging tray prior to use, such as from a tube or other container of the medium. In either case, the imaging tray may be reusable or disposable.

As shown in step 1504, the method 1500 may include inserting an object into the imaging tray. This may include placing an object into the imaging tray (such as where the medium is a liquid), or applying a force to insert the object into the medium within the imaging tray. For example, where the imaging tray is a dental bite tray, this may include inserting human dentition into the dental bite tray, such as by having a user apply force by biting into the medium with the teeth and other dentition that are the object of the impression. However inserted, the object may in general displace the medium and form an impression of the object within the medium.

As shown in step 1506, the method 1500 may include illuminating the interior surface of the imaging tray. This may include any of the illumination techniques described above.

As shown in step 1508, the method 1500 may include capturing an image of the interior surface at the first wavelength and the second wavelength. This may in general include any of the imaging techniques described above. It will be understood that capturing an image in this context is intended to refer to the direction of the surface rather than the surface itself. Thus for example where a transparent imaging tray is used, the image captured may be an intensity of light from a medium behind the interior surface rather than the interior surface itself. Thus in many embodiments the image may relate to the direction in which light intensity is measured rather than an actual location from which light is reflected.

Capturing an image of the interior surface may also, or instead, include capturing a reference image of a plurality of fiducials provided within the imaging tray. These fiducials may be used to determine a three-dimensional position and orientation of an imaging tray using any of a variety of known techniques. This may include processing of the same image used to calculate thicknesses (e.g., an image of the interior surface at the first wavelength and the second wavelength), such as by locating and interpreting the fiducials in such images, or this may include capturing a supplemental image with the same camera or sensor(s) for processing of the fiducials. In another aspect, a supplemental camera or other imaging device may be provided in order to capture a reference image of the fiducials. In such embodiments, the supplemental camera should have a known spatial relationship to the camera or sensors used for thickness measurements.

As shown in step 1510, the method 1500 may include processing the image to determine a thickness of the medium in a direction of the interior surface. This may include any of the processing techniques described above based upon a ratio of intensities of two different wavelengths of light, or any other similar technique or approach. This may include capturing a plurality of thickness measurements for a plurality of directions toward the interior surface, such as from a two-dimensional array of intensity measurements captured by a camera or the like.

As shown in step 1512, the method 1500 may include obtaining a three-dimensional reconstruction of the object from the thickness measurement(s). This may include, for example, applying a number of thickness measurements, in view of the known dimensions of the interior surface, to determine a three-dimensional shape of the object, or the boundaries of an impression of the object in the medium. It will be understood that for a variety of reasons there may be subtle or substantial deviations between the actual object shape and the actual impression of the object. Either or both of these (conceptually) mirror-imaged surfaces are intended to fall within the scope of the three-dimensional shape of the object as that phrase is used herein.

It will be appreciated that the method 1500 described above is set forth by way of example and not of limitation. Numerous variations, additions, omissions, and other modifications will be apparent to one of ordinary skill in the art. In addition, the order or presentation of these steps in the description and drawings is not intended to require this order of performing the recited steps unless a particular order is expressly required or otherwise clear from the context. Thus, for example the object may be inserted into an imaging tray before the medium is disposed therein. Or various types of fiducials may be used to relate thickness measurements to positions within the imaging tray. Similarly, while human dentition is specifically mentioned, the approach may be adapted to a wide variety of biological or other subject matter, and all such variations are intended to fall within the scope of the present disclosure.

The systems and methods described herein can be usefully employed to obtain high-accuracy three-dimensional images of interior spaces such as an ear canal or other human or machine cavity by inflating a membrane with a suitable medium or, where the cavity is sufficiently liquid-tight, simply filling the cavity with a suitable and compatible (e.g., biocompatible) medium, all as described above. In general, these techniques can be applied to obtain a complete three-dimensional model from a single frame of wavelength data. More specifically a three-dimensional reconstruction of a surface can be calculated by relating particular directions through a medium (according to the image capture geometry) to particular distances through the medium (according to a ratio of two wavelengths in that direction), thereby providing a three-dimensional surface of points. As a further advantage, this permits dynamic imaging or three-dimensional video that, as the shape varies from frame to frame, captures time-based variations in the surface. Thus in one aspect, there is disclosed herein a technique for capturing dynamic three-dimensional data from an interior cavity. This dynamic data has a wide array of potential diagnostic, design, and modeling applications as will be discussed in greater detail below.

As used herein, the term "dynamic data" is intended to refer generally to data such as ear canal shape data that changes over time. Two types of dynamic data are generally contemplated by this disclosure. "Compliance" data refers to shape or surface data that is linked to pressurization, such as for compliance of an ear canal shape to changes in pressurization. Where an inflatable membrane has a known pressurization, this compliance can be quantitatively measured using the devices described above to provide compliance data that is useful for design and customization of earpieces and other applications described herein. On the other hand, "shape change" data refers to shape or surface data that is linked to musculoskeletal movement of a subject. So for example, if a subject tilts or swivels the head, opens or closes the jaw, yawns, nods, talks, chews, or otherwise engages in movement of the head and associated muscles, bones, or other tissue, this may yield a shape change in the ear canal that can be measured quantitatively as shape change data. Shape change data may be used instead of or in addition to compliance data for the design and customization of earpieces, along with other applications as described herein. It should be understood that the term "musculoskeletal movement", even when limited to the head, is intended to be broadly construed. Thus for example such movement may include movements of cartilage, soft tissue, or any other tissue. Similarly, other musculoskeletal movement such as shrugging the shoulders may induce corresponding movements of head tissue and resulting changes to the shape of the ear canal. All such movements that might result in shape change within the ear canal are intended to fall within the scope of "musculoskeletal movement" and/or "musculoskeletal movement of the head" unless a different meaning is explicitly provided or otherwise clear from the context.

Figure 16:
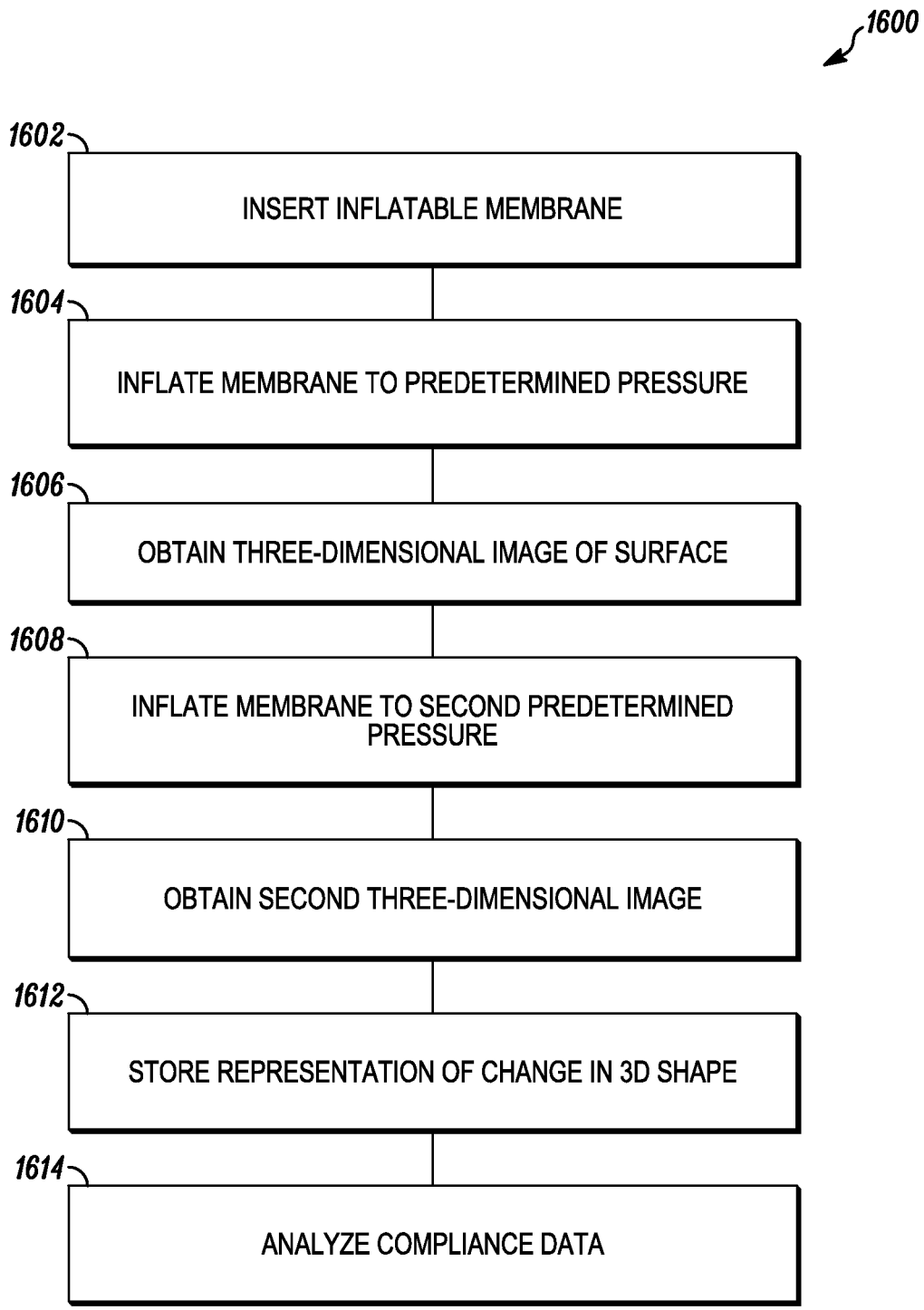
FIG. 16 is a flow chart of a method for measuring compliance.

FIG. 16 is a flow chart of a method for measuring compliance. The method may be employed, for example, using any of the devices described above to measure compliance in, e.g., a human ear canal.

As shown in step 1602, the method 1600 may begin with inserting an inflatable membrane, such as any of the inflatable membranes described above, into a cavity such as an ear canal.

As shown in step 1604, the method may include pressurizing the inflatable membrane within the cavity with a fluid to a predetermined pressure, thereby providing an inflated membrane. The predetermined pressure may be a fixed target pressure, or the pressure may be determined during use based upon, e.g., feedback from a patient concerning comfort of fit. Thus in one aspect, the pressurization of the inflatable membrane may be used to achieve a more comfortable fit for a hearing aid or other ear device by providing information on oversizing the ear device. Similarly, the predetermined pressure may be a pressure that is measured after a technician or other user observes and adequate shape, size, or fit of the inflatable membrane within a cavity.

It will further be understood that the pressure may be a time-varying pressure or changing pressure that varies in a predetermined manner over a predetermined interval. For example, a fixed pressure may yield unreliable results in a typical environment where the inflatable membrane is operated as a handheld probe and the probe may be susceptible to independent pressure variations due to hand tremors, head tremors, and the like. In such an imaging environment, the predetermined pressure may be a continuously varying pressure such as a mechanically driven pulsatile wave, sinusoidal pressure wave, triangle wave, ramp, square or rectangle wave, and so forth. Corresponding compliance measurements may be averaged or otherwise characterized over one or more cycles of the pressure wave. Similarly, the frequency response of the cavity shape to different frequencies and magnitudes of pressure variation may provide useful information concerning the nature of the cavity walls, e.g., whether the underlying tissue is bone, cartilage, soft tissue, or the like. In this context, different frequency variations may be appropriate in different imaging environments, and may be adjusted to maximize detected motion. Thus for example, when measuring lung compliance to identify areas of damaged or scarred tissue, certain frequencies of pressure variation may provide greater sensitivity to underlying tissue variations and improve diagnostic or other value of the obtained compliance data.

The fluid may include any liquid, gas, gel, foam, or other fluid than can be used to inflate the membrane. Various optical properties of this fluid are discussed above, and may be selected according to a three-dimensional imaging technique that is being used.

As shown in step 1606, the method 1600 may include obtaining a three-dimensional image of a surface of the inflated membrane at the predetermined pressure. This may, for example, include capturing in image with an image sensor or the like at two different wavelengths, determining a thickness of the medium used to inflate the inflatable membrane in each direction that data is captured from the image sensor, and transforming this directional and distance data into a representation of the surface of the inflatable membrane at a plurality of points, all as generally contemplated above.

In one aspect, the three-dimensional image may be an image of an outer ear canal of a patient or user with an earpiece positioned in the ear canal. Thus the three-dimensional image of the surface may be used to evaluate a fit of the earpiece, such as by confirming a desired position or orientation. In such embodiments, the method 1600 may omit any further capture of images, and stop after sufficient image data is obtained to evaluate the fit of the earpiece.

As shown in step 1608, the method may include changing the pressure within the inflated membrane to a second predetermined pressure different from the predetermined pressure.

As shown in step 1610, the method may include obtaining a second three-dimensional image of the surface of the inflated membrane at the second predetermined pressure.

As shown in step 1612, the method may include storing a representation of a change from the three-dimensional image to the second three-dimensional image as compliance data for the cavity. It will be appreciated that while a generally two-state comparison is described, numerous variations are possible. Thus any number of static (e.g., fixed pressure) or dynamic (e.g., varying pressure) images may be captured and compared without departing from the scope of the invention. By imaging with three-dimensional data captured through the medium that is used to pressurize the inflatable membrane, any type and amount of compliance data may be usefully captured and analyzed using the systems described above. Thus more generally a plurality of different pressures and pressure change frequencies and magnitudes may be used based upon the generalized method described above.

The representation of the change in the three-dimensional image may be stored, for example, in the memory of a computer or in a database or any other suitable volatile or non-volatile storage medium that can store a non-transitory representation of the corresponding data. The representation of change may itself take a variety of forms. This may, for example include storing the predetermined pressure and the second predetermined pressure, or where these pressures are time-varying, representative data such as a center frequency, magnitude, and duration of the applied or measured pressure. The representation may also include a number of corresponding surfaces under various pressurizations, or a volumetric displacement resulting from the pressure changes, or some combination of these such as an initial shape under one pressurization scheme and displacement data for differing pressurization schemes. Similarly, other change data may be stored such as a linear displacement normal to the surface at one or more locations on the surface, a deformation or other three-dimensional displacement from one image to the next, or the like. In one aspect, the representation may be stored as a three-dimensional video that can be retrieved and displayed for human review. This may be particularly useful, for example, where generally increasing or decreasing pressurization is applied to the ear canal and an ear piece designer wishes to directly observe how the ear canal yields to increased pressurization.

As shown in step 1614, the compliance data may be analyzed. This may, for example, include analyzing the compliance data to quantitatively characterize changes in response to pressurization as discussed above. Any other analysis, such as drawing inferences concerning tissue type, elasticity, and so forth, may also be performed.

It will be readily appreciated that a device such as any of the devices described above may be adapted to perform the method of FIG. 16 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 1600.

Figure 17:
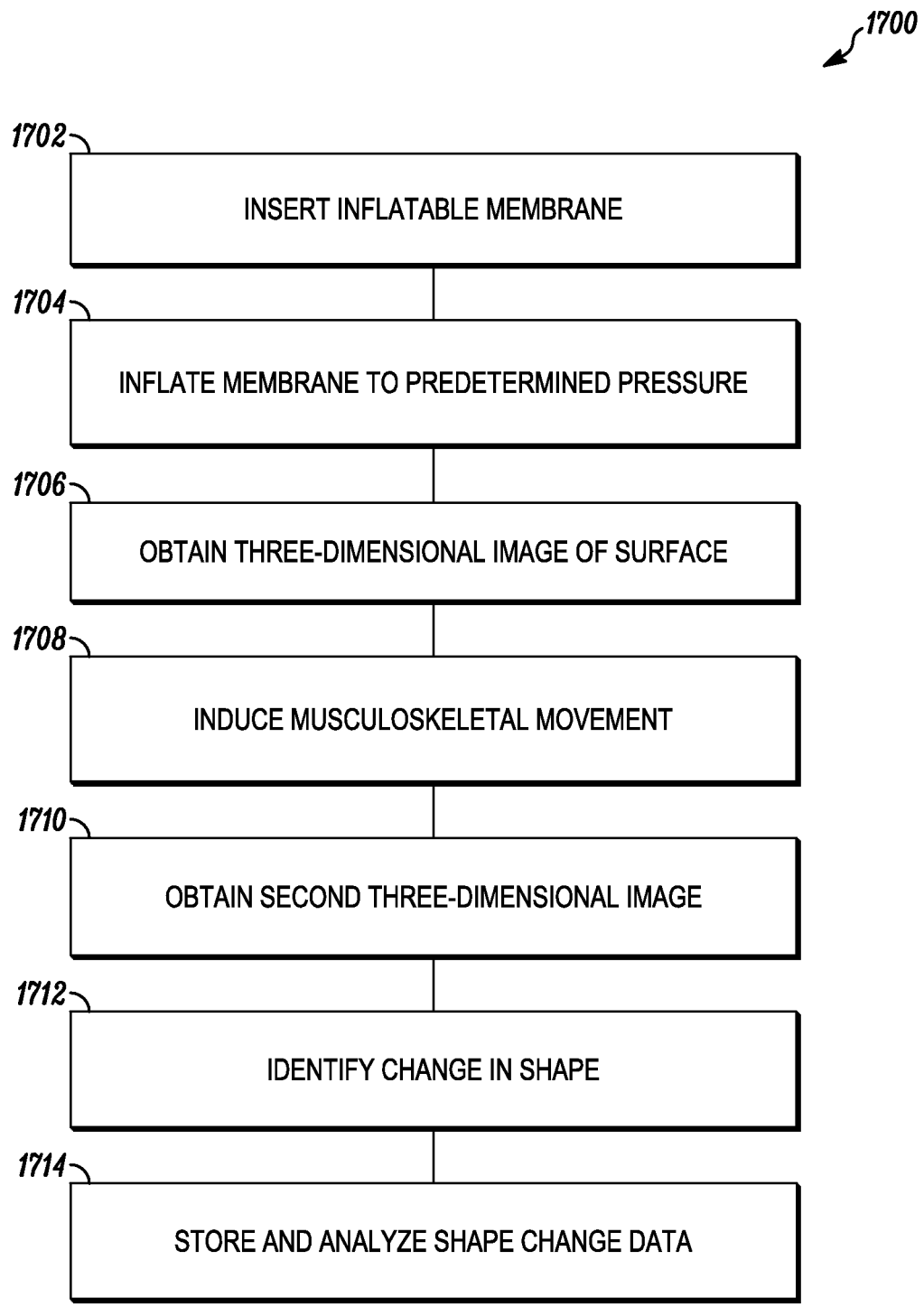
FIG. 17 is a flow chart of a method for measuring shape change in a cavity in response to musculoskeletal movements.

FIG. 17 is a flow chart of a method for measuring shape change in a cavity in response to musculoskeletal movements. While the following description generally contemplates two different discrete musculoskeletal positions, this is the most basic formulation of measuring shape change, and it will be appreciated that detecting continuous shape change over a range of motion may be more useful in a variety of contexts. As such, any number of different measurements may usefully be taken in various applications.

As shown in step 1702, the method 1700 may begin with inserting an inflatable membrane into an ear canal or other cavity of a subject, as generally described above for example with reference to FIG. 16.

As shown in step 1704, the method 1700 may include pressurizing the inflatable membrane within the ear canal with a fluid to a predetermined pressure, thereby providing an inflated membrane, all as generally described above for example with reference to FIG. 16. In one aspect, this may include inflating the inflatable membrane to a target pressure that is maintained, e.g., with a proportional-integral-derivative ("PID") controller or the like. In another aspect, this may include inflating the inflatable membrane to a comfortable pressure level for a subject, which may be measured and may usefully serve as a basis for shaping and sizing an earpiece.

As shown in step 1706, the method 1700 may include obtaining a first three-dimensional image of a surface of the inflated membrane at the predetermined pressure, all as generally described above for example with reference to FIG. 16.

As shown in step 1708, the method 1700 may include causing a musculoskeletal movement of a head of the subject, which may be broadly understood as any of the musculoskeletal movements described above. This may, for example, include talking, making specific vowel or consonant sounds, yawning, opening or closing the mouth, moving the lower jaw from side to side, moving the shoulders, tiling the head, or any other motion or combination of motions. This may include measuring the musculoskeletal movement of the head using any suitable manual or computerized technique, including by way of example any of the two-dimensional or three-dimensional image capture techniques described below. Thus in one aspect, this may include obtaining two or more three-dimensional images of the head of the subject to quantitatively characterize the musculoskeletal movement.

As shown in step 1710, the method 1700 may include obtaining a second three-dimensional image of the surface after the musculoskeletal movement. In general, the three-dimensional images may be captured at various times during the musculoskeletal movement. Thus in one aspect, the two or more three-dimensional images may include at least one three-dimensional image captured before causing the movement, at least one three-dimensional image after causing the movement, and at least one three-dimensional image during the movement. In this manner, ear canal shape data for a starting position, and ending position, and any desired number of intermediate positions may be captured for analysis.

As shown in step 1712, the method 1700 may include identifying a change in shape of the surface between the first three-dimensional image and the second three-dimensional image. As noted above, a number of additional images may be obtained to help characterize a range of shape change in the ear canal corresponding to a range of other musculoskeletal movements. For example, extreme or minimum/maximum positions may be misleading where the ear canal actually expands and then contracts over a specific range of musculoskeletal movement. In addition, a full motion video may be useful to an earpiece designer, and may be captured and stored for later reference. In addition, two-dimensional or three-dimensional video of the musculoskeletal movement (as distinguished from the ear canal shape) may be captured and timewise synchronized to the ear canal three-dimensional images in order to more fully characterize the movements that induced the ear canal shape change. This may be obtained using any conventional two-dimensional or three-dimensional imaging system, the details of which are not recited here. In such a context, a head motion video, jaw motion video, or the like may be captured and stored with the ear canal three-dimensional video.

As shown in step 1714, the method 1700 may include storing and analyzing the change in shape. This may include storing the change in shape as ear canal shape change data for the subject. Storing the change in shape may include storing the first three-dimensional image and the second three-dimensional image. Storing the change in shape may also or instead include storing a movement between the first three-dimensional image and the second three-dimensional image. Storing the shape change data may also or instead include storing a displaced volume between the first three-dimensional image and the second three-dimensional image. In general, the actual change in shape may be represented in a variety of forms that will readily be appreciated by one of skill in the art including volumetric displacements, linear displacements, and so forth.

The analysis may include a variety of analyses based upon the shape change and the corresponding musculoskeletal movements. This may, for example, include relating the musculoskeletal movement to the change in shape. This may also or instead include analyzing the ear canal shape change data to quantitatively characterize how the ear canal changes shape in response to the musculoskeletal movement. This may also include characterizing the musculoskeletal movement of the head as a type of movement and storing the type of movement. Thus, for example, the musculoskeletal movement may be characterized as a "yawn," a "clench," or any other suitable movement, and the data may be explicitly labeled to reflect this movement type.

It will be readily appreciated that a device such as any of the devices described above may be adapted to perform the method of FIG. 17 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 1700.

Figure 18:
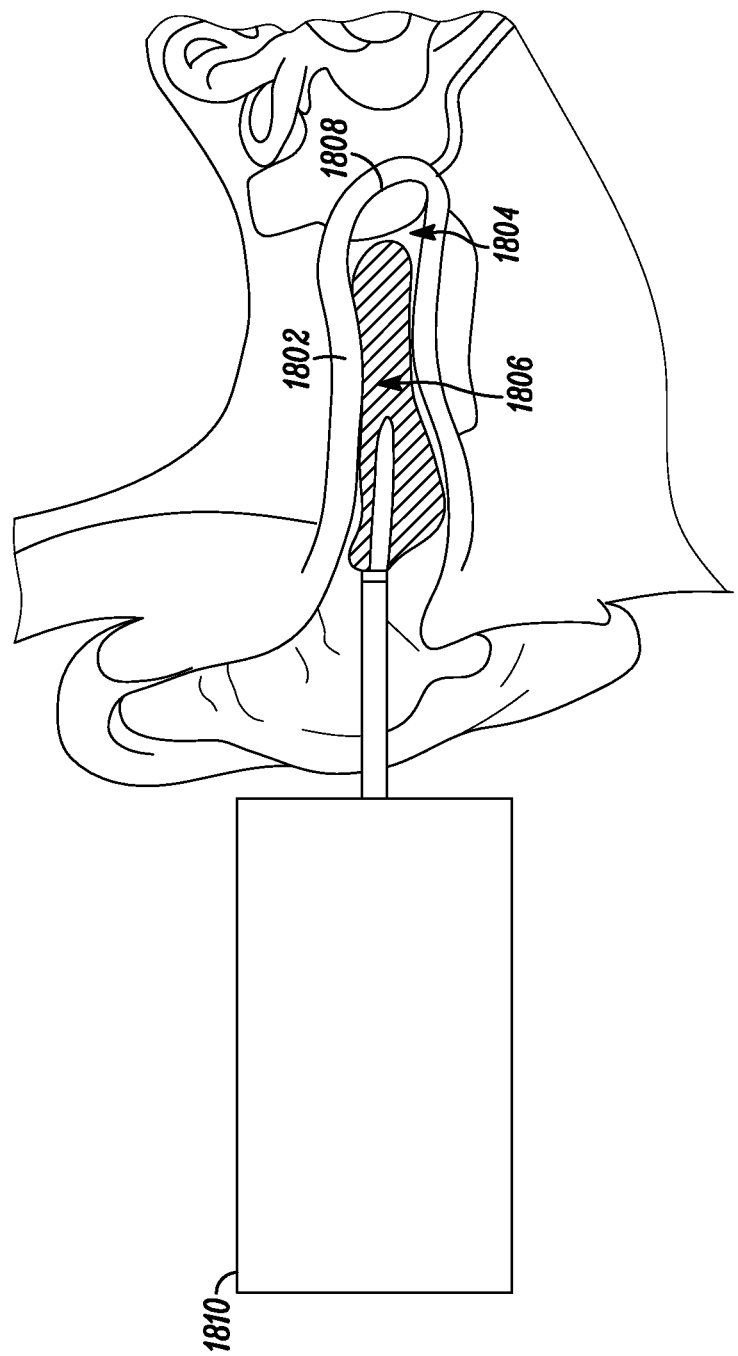
FIG. 18 shows an inflatable membrane within an ear canal

FIG. 18 shows an inflatable membrane within an ear canal. In general, an inflatable membrane 1802 is positioned for use within an ear canal 1804 and pressurized with an imaging medium 1806 as generally described above. The inflatable membrane 1802 may contact a tympanic membrane 1808, or a location of the tympanic membrane 1808 may be inferred from the more general geometry of the ear canal 1804. The inflatable membrane 1802 may be coupled to a handheld probe 1810 or other housing, which may house imaging hardware, processing circuitry, memory, a medium delivery and control system, and other hardware, all as described above in greater detail. Within the inflatable membrane 1802, sensors, a light source and other hardware may also be included, also as described above in greater detail. Having shown the manner in which the inflatable membrane 1802 is place for use within the ear canal 1804, additional techniques for using acquired data will now be described.

Figure 19:
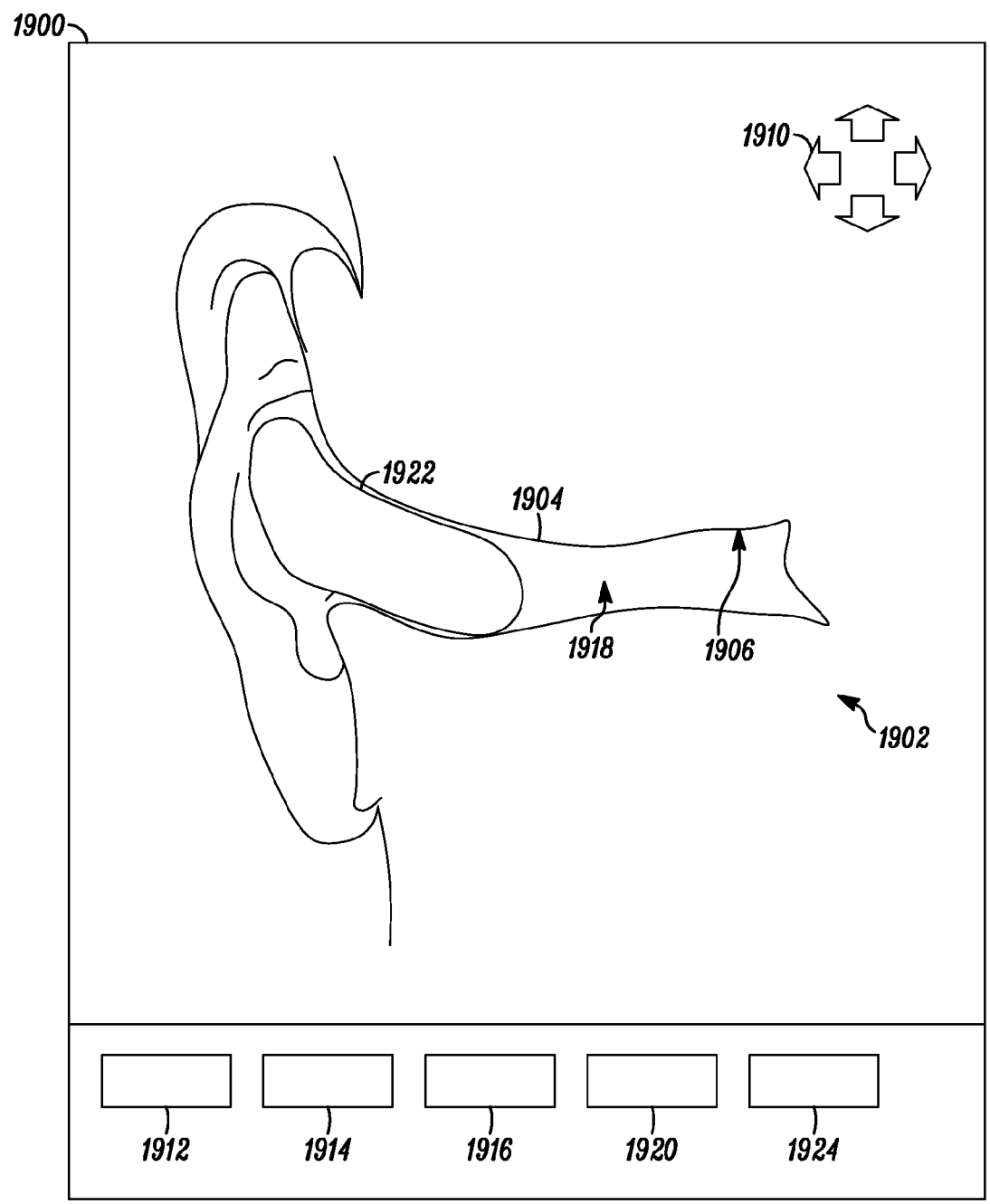
FIG. 19 depicts a user interface for earpiece design/selection using dynamic data as contemplated herein.

FIG. 19 depicts a user interface for earpiece design/selection using dynamic data as contemplated herein. In general, the user interface 1900 may include a depiction of an ear canal 1904 based upon three-dimensional data captured as described above. The interface may generally show an image 1902 including a shape of the ear canal 1904 in cross-section or other two-dimensional or three-dimensional view based upon capture shape data. The image 1902 may be color-coded or annotated with quantitative values reflecting elasticity, hardness, or the like around an inner wall 1906 of the ear canal, or inferred tissue structure such as bone, cartilage, or the like may be displayed.

In general, the user interface 1900 may include navigation controls 1908 for panning, zooming, rotating, or otherwise manipulating the perspective of the view of the ear canal 1904 and surrounding spatial data. Further, any number of controls such as buttons, sliders, text fields, and the like may be included to assist a user in an earpiece design or selection process. This may, for example, include a first control 1912 to auto-select an earpiece. A second control 1914 may permit manual selection or sizing of an earpiece. A third control 1916 may permit acoustic testing based upon, e.g., a simulation of an acoustic chamber 1918 formed within the ear canal 1904. A fourth control 1920 may permit sizing or movement of a selected earpiece 1922 within the ear canal 1904. A fifth control 1924 may permit selection of a musculoskeletal movement and/or animated display of corresponding shape changes to the ear canal 1904. More generally any useful control or group of controls may be included within the user interface 1900 to assist a user in an automated, semi-automated, or manually design process using dynamic data such as compliance data or shape change data as generally contemplated herein.

It will be understood that the imaging system described herein may only obtain detailed three-dimensional data from portions of the ear canal. Thus the user interface may augment the captured data with a stylized or abstract ear, tympanic membrane, and so forth to provide a user with appropriate context. Alternatively, this ancillary data may be omitted from the user interface, or actual three-dimensional data may be captured form a user's outer ear, head, and the like to provide a more accurate contextual depiction within the user interface.

Figure 20:
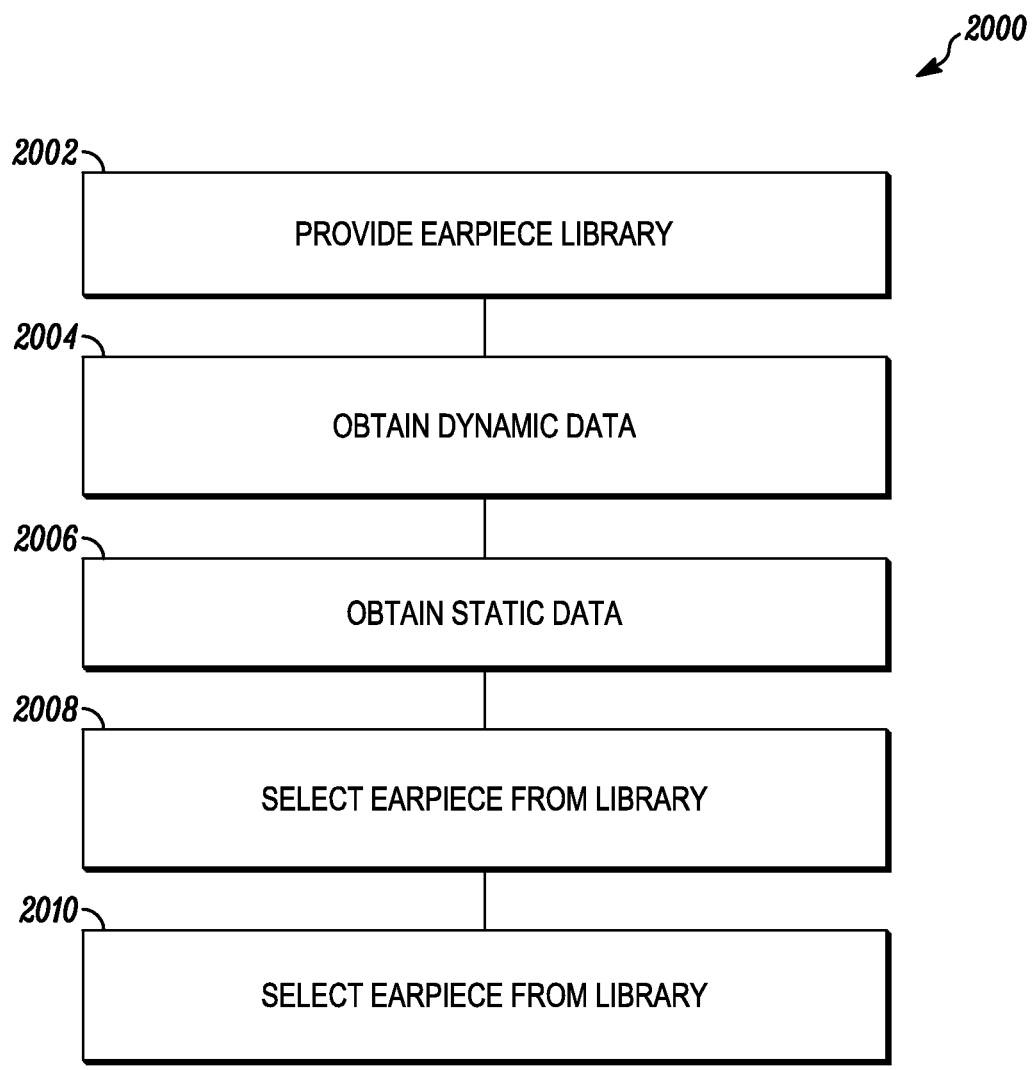
FIG. 20 is a flowchart of a method 2000 for earpiece selection using dynamic data.

FIG. 20 is a flowchart of a method 2000 for earpiece selection using dynamic data. In general, dynamic data may be used to identify soft tissue, bone, cartilage, and the like that forms an inner wall of an ear canal or other cavity, and shape data may more generally characterize ear canal shape, an acoustic chamber formed by placement of an earpiece, and other features of the ear canal such as location of the tympanic membrane, all as described above. This data may be usefully employed to determine the size and shape of an earpiece such as a hearing aid, or to select one of a number of pre-fabricated hearing aids, or shells for hearing aids, that best fit the ear, taking into account aspects of the ear canal such as size and shape. In addition, the earpiece may be designed or selected so that the earpiece is suitably oversized for a secure fit where there is soft tissue within the ear canal, or undersized to avoid discomfort around bone or other hard tissue.

As shown in step 2002, the method 1900 may include providing a library of earpieces that includes three-dimensional shape data for a plurality of preexisting earpiece types. A variety of earpiece types are known, include behind-the-ear (BTE), mini behind-the-ear (mini-BTE), in-the-ear (ITE), in-the-canal (ITC), and completely-in-canal (CIC). Each type may have one or more shapes or sizes, which may be adapted for insertion or provided as a shell over which a customized mold for a patient may be designed and added. The library may include other information concerning acoustics, microphone placement, feature or hardware specifications, and so forth. While the earpieces may include hearing aids such as those described above, it will further be appreciated that the earpieces may be other earpiece types or subassemblies. For example, the earpieces may include earbuds for audio players, or the earpieces may include earpiece bodies for use with personalized molds that are customized for individual users.

As shown in step 2004, the method 2000 may include obtaining dynamic data from an ear canal of a subject as generally described above. The dynamic data may more specifically include data from the ear canal characterizing changes in a shape of the ear canal related to at least one of a compliance of the ear canal to changes in pressurization or a shape change of the ear canal in response to a musculoskeletal movement of a head of the subject.

As shown in step 2006, the method may include obtaining static data from the ear canal of the subject, the static data including a three-dimensional representation of a surface of the ear canal. The static data may be used, for example, to size an earpiece, and to provide a three-dimensional shape of the ear canal for display in a user interface.

As shown in step 2008, the method 2000 may include selecting one of the plurality of preexisting earpiece types from the library that provides a best fit to the ear canal based on the dynamic data, thereby providing a selected type. A variety of techniques for making this selection are available. This may include automated selection based on geometric comparison, filtering based on the ability of the ear canal to yield to an inserted device based on, e.g., the dynamic data, and so forth. The parameters for fitting an earpiece to an ear canal are well known in the art, and are not described here in detail except by way of illustrative example. A user interface as illustrated above may be provided in a computerized system to permit a user to manually compare fits of various devices. In general, the selection may account for volumetric constraints (actual fit of device components (battery, speaker, processor, microphone, vent tubes, etc.)), positioning constraints (suitable location relative to tympanic membrane), and so forth. For example, Invisible-In-The-Canal (IIC) hearing aids impose specific size requirements on the ear canal near the tympanic membrane, which geometric features may be directly viewed by a user within the user interface, or automatically analyzed for appropriateness of an IIC based upon three-dimensional shape data.

Selecting an earpiece may additionally include making an initial selection of one of the plurality of preexisting earpiece types from the library based upon the static data, and evaluating a fit of the one of the plurality of preexisting earpiece types based on the dynamic data. This evaluation may include a spatial test fit of the earpiece to the ear canal, as well as simulation of acoustics within the acoustic chamber and any other useful evaluations relating to comfort of the earpiece for the user, performance of the earpiece, and so forth.

As shown in step 2010, the method 2000 may include creating a digital design for a personalized mold that is shaped and sized for the ear canal of the subject. For certain earpieces, a standard body is customized for an individual with a personalized shell or covering. When such an earpiece is selected, the design process may include generating a three-dimensional design for the shell based upon the geometry of the standard body and the geometry of the ear canal, as obtained using the inflatable membrane described above. In such circumstances the standard body and customized shell may be displayed within a user interface and simulated or otherwise tested for fit over a range of motion. In addition, data such as compression of the shell (which may be oversized to the ear canal) may be estimated and adjusted by a user for improved seal, comfort, or the like.

It will be readily appreciated that a device such as any of the devices described above may be adapted to perform the method of FIG. 20 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 2000.

Figure 21:
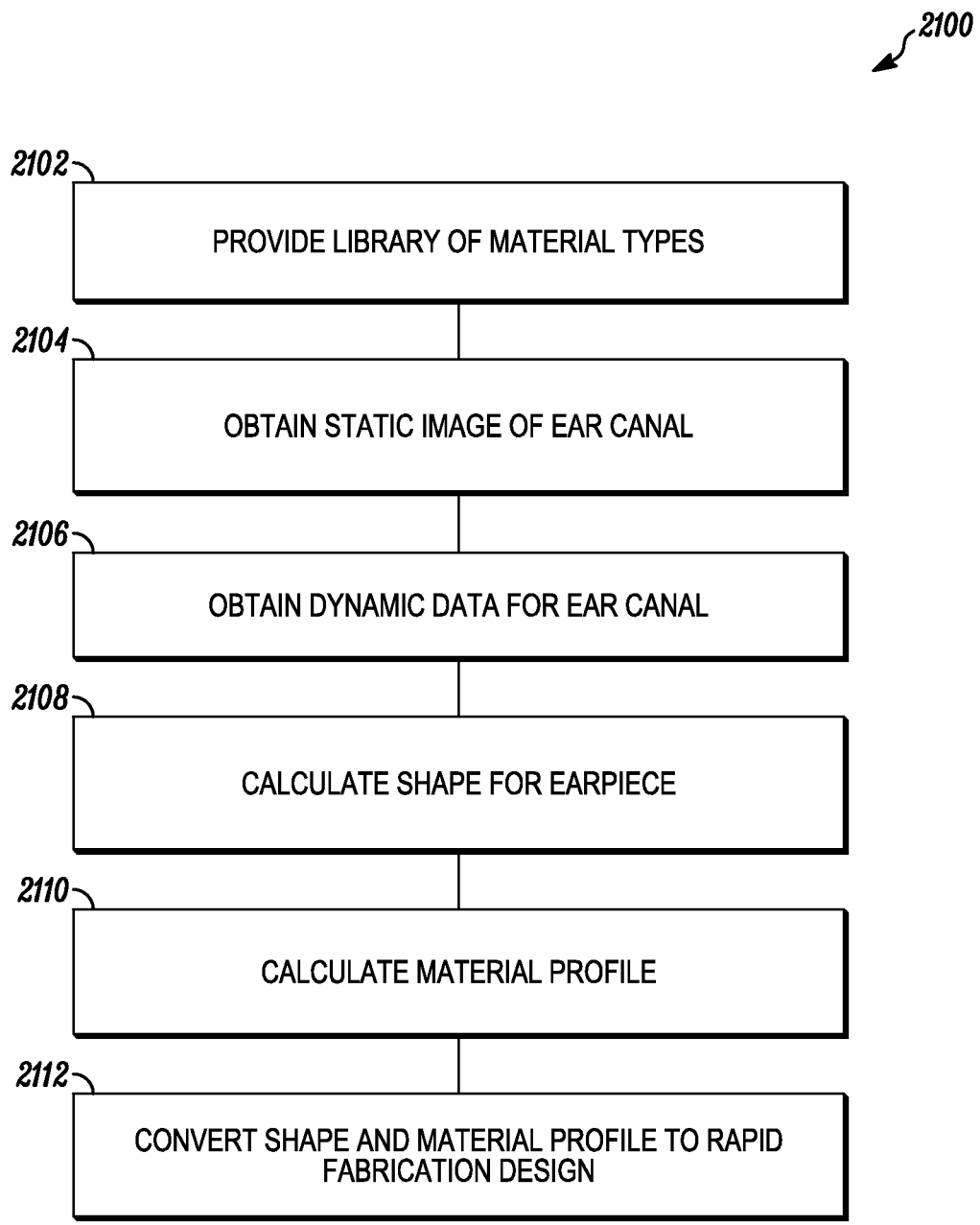
FIG. 21 is a flowchart of a method 2100 for creating a material profile to fabricate an earpiece.

FIG. 21 is a flowchart of a method 2100 for creating a material profile to fabricate an earpiece. In general, the shape of an ear canal and the relative elasticity of tissue surrounding the ear canal may suggest materials having different stiffness or elasticity. In addition, different modes of deformation for an earpiece may be suggested by, for example, the insertion/removal path for the earpiece, the position of an acoustic seal, and so forth. The material profiles described below may accommodate any one or more of these physical constraints on earpiece design and use, and may be applied to select from preexisting earpieces or to specify materials for a custom-fabricated earpiece.

As shown in step 2102, the method 2100 may begin with providing a library of a plurality material types available for use in a fabrication process, each of the plurality of material types characterized by elasticity. Each material may be further characterized by any of a number of additional parameters such as strength, durability, comfort, cost, acoustic properties, and the like, including without limitation any parameter that might be used to evaluate the material's suitability for a particular object to be fabricated. For example, each material may characterized by at least one of a bulk modulus, a modulus of elasticity, and a compressibility. These properties may be used to simulate a static fit, and to evaluate whether and how the fit is maintained as the ear canal changes shape over time (e.g., in response to musculoskeletal movements). Similarly, each material may be characterized by two or more elastic moduli, e.g., along orthogonal axes, or any other mechanical properties such as viscoelastic properties. The library may be stored in a database or any other suitable non-transitory medium.

As shown in step 2104, the method 2100 may include obtaining static data from an ear canal of a subject, the static data including a three-dimensional image of a surface of the ear canal at a predetermined pressure. This may include image capture using any of the systems and methods described above.

As shown in step 2106, the method 2100 may include obtaining dynamic data from the ear canal of the subject, the dynamic data including data from the ear canal characterizing changes in a shape of the ear canal related to at least one of a compliance of the ear canal to changes in pressurization or a shape change of the ear canal in response to a musculoskeletal movement of a head of the subject. This may more generally include any dynamic data captured using the systems and methods described above.

As shown in step 2108, the method 2100 may include calculating a shape for an earpiece based upon the static data. In general, this includes matching an earpiece to the geometry of the ear canal, taking into account insertion and removal, an acoustic seal and the formation of an acoustic chamber adjacent to a tympanic membrane, oversize for secure fit, undersizing for comfort, placement of earpiece hardware and vents, and so forth. For example, the ear canal may narrow in response to certain musculoskeletal movements such as when the mouth opens. In addition to selecting a softer material for these regions, the earpiece may be undersized, or alternatively, undersized relative to a standard oversizing margin, to more readily accommodate these anticipated shape changes during use. In one aspect, calculating earpiece shape may involve fitting to geometry of the ear canal, the outer ear, and so forth.

This may include oversizing the earpiece relative to the ear canal by a predetermined amount (e.g. 10% by volume or by linear dimension) throughout the earpiece. The predetermined amount may be varied according to the dynamic data, e.g., by oversizing more in areas of greater elasticity (of the ear canal wall) and oversizing less in areas where the ear canal wall is harder, such as near bone or other hard tissue. More generally, oversizing may include varying the amount of oversizing in different regions of the earpiece. In another aspect, this may include adapting the shape and size using known principles of earpiece design to achieve an earpiece that securely fits within the ear canal, is comfortable for a user, and provides good acoustic performance. The predetermined amount of oversizing may also be determined in part by the hearing loss profile of an intended user. For example, people with large hearing loss typically require large gain in amplification, which increases the chance of feedback squeal if an air gap opens up between the speaker and microphone. In such a context, there may be more oversizing to prevent adverse acoustic consequences, even if this comes at the expense of patient comfort.

As shown in step 2110, the method 2100 may include calculating a material profile for the earpiece based upon the dynamic data using one or more of the plurality of material types of the library. That is, given the shape determined in step 2108, along with information about fit and use of the earpiece derived from the dynamic data, suitable materials may be selected for fabrication of an earpiece having the desired shape and desired physical and mechanical properties. It will be appreciated that determination of a material profile may be performed concurrently with the shape determination of step 2108, or after the earpiece shape is determined, or iteratively such as where shape and material profile are alternately adjusted to converge on a final shape and material profile.

As shown in step 2112, the method 2100 may include converting the shape and the material profile into an earpiece design for use by a rapid fabrication system. In such a design, each of the plurality of material types may be selected from materials available in a rapid fabrication process, or multiple rapid fabrication processes, so that the resulting shape and material profile can be readily converted into suitable tool instructions.

It will be readily appreciated that a device such as any of the devices described above may be adapted to perform the method of FIG. 21 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 2100.

Figure 22:
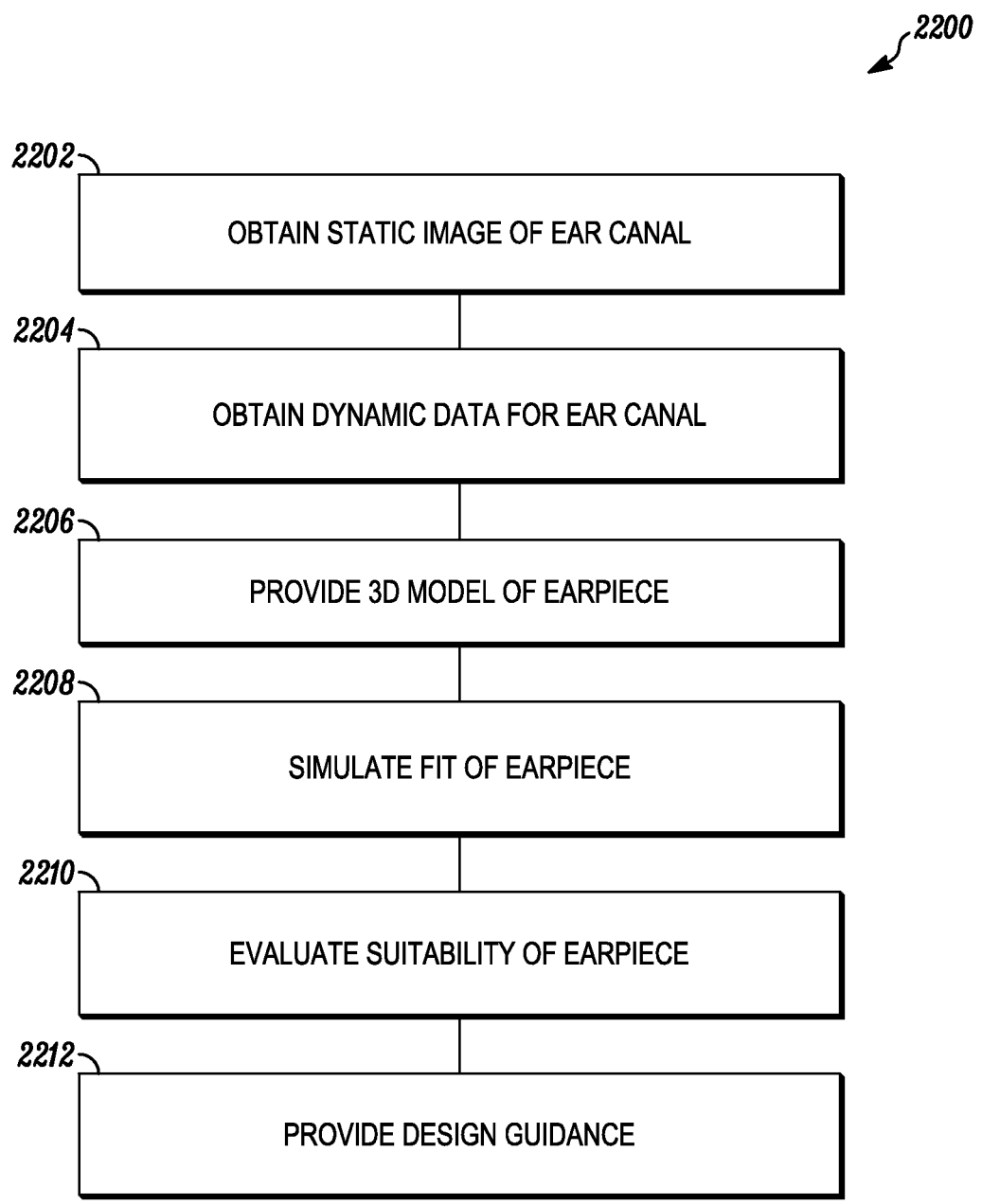
FIG. 22 is a flowchart of a method for simulation of dynamic fit and acoustics for an earpiece.

FIG. 22 is a flowchart of a method for simulation of dynamic fit and acoustics for an earpiece. In generally, the dynamic data and static data for an ear canal, as captured using the systems and methods disclosed above, may be used to simulate an earpiece placed for use in an end user's ear canal, and to thereby improve design prior to fabrication of the earpiece.

As shown in step 2202, the method 2200 may begin with obtaining static data from an ear canal of a subject, the static data including a three-dimensional image of a surface of the ear canal at a predetermined pressure. This may include a scan of ear canal shape using an inflatable membrane as described above. It will be appreciated that the 'static' image may be obtained under pulsating or otherwise varying pressure as generally discussed above. As such, the term static as used to describe image data does not necessarily imply static imaging conditions, but rather is intended to describe the capture of a fixed three-dimensional shape, in contrast to dynamic data which captures shape variations under time-changing conditions.

As shown in step 2204, the method 2200 may include obtaining dynamic data from the ear canal of the subject, the dynamic data including data from the ear canal characterizing changes in a shape of the ear canal related to a compliance of the ear canal to changes in pressurization and a shape change of the ear canal in response to a musculoskeletal movement of a head of the subject. The compliance data may be used, for example, to model acoustic behavior of the ear canal walls, or to how the ear canal wall will yield (or conversely how an earpiece will yield) when an earpiece is placed for use therein.

As shown in step 2206, the method may include providing a three-dimensional model of an earpiece. It will be understood that this may be a complete physical model including a complete characterization of exterior surfaces of the earpiece, or this may include other information such as overall sizing limits or the shape and/or size of individual components (circuitry, battery, speaker, microphone, etc.) that must be included in the earpiece, from which a specific or generalized shape and size may be determined.

As shown in step 2208, the method may include simulating a fit of the three-dimensional model of the earpiece to the ear canal based on the static data and the dynamic data, thereby providing a simulation result. It will be understood that given a static and dynamic model of an ear canal, as captured using the methods and systems disclosed herein, along with a physical model of an earpiece, a variety of simulations may be performed. This may generally include physical simulation of earpiece fit, as well as various acoustic properties based upon, e.g., the shape of the acoustic chamber formed within the ear canal and the properties of the ear canal walls as determined by the dynamic data.

In another aspect, step 2208 may include simulating an acoustic response of a chamber formed when the earpiece is placed in the ear canal based on the static data and the dynamic data. The acoustic response may depend on placement of various acoustic components. As such, the simulation may include selecting a location for a placement of a speaker in the earpiece based upon the acoustic response. Where speaker location has been satisfactorily simulated, the subsequent design/evaluation steps may include positioning the speaker in a desired location within an earpiece model for fabrication or creating a digital model for fabrication of an earpiece that includes the speaker placed at the location. Other simulations may also or instead be performed. For example, the method 2200 may include evaluating an integrity of an acoustic seal for the chamber formed by the earpiece based upon the shape change of the ear canal in response to the musculoskeletal movement of the head, acoustically simulating a microphone for the earpiece, or optimizing vent placement for the earpiece.

As shown in step 2210, the method may include evaluating a suitability of the earpiece for the ear canal based upon the simulation result. Suitability may be based on one or more of a variety of criteria. For example, suitability may be evaluated based on the characteristics of an acoustic chamber formed within the ear canal by the earpiece, or the quality of an acoustic seal formed by the earpiece when placed for use in the ear canal. This determination may rely for example on the acoustic properties of the ear canal wall as determined from the dynamic data. As another example, suitability may be evaluated based on the nature of the physical fit between an earpiece and the ear canal. Thus for example, if air gaps form between the earpiece and the ear canal wall during various musculoskeletal movements, the earpiece model or design may be rejected as unsuitable. Similarly, if excessive pressure is exerted against the ear canal when the earpiece is inserted, this may result in user discomfort that would render the earpiece unsuitable. Thus in one aspect evaluating suitability may include estimating a comfort of the earpiece for a subject, more specifically the subject from which the static and dynamic ear canal data was obtained.

As shown in step 2212, the method 2200 may include providing design guidance based upon the simulation and evaluation. This may, for example, include modifying the three-dimensional model of the earpiece based upon the simulation result (or suggesting modifications for manual entry by a user). This may also or instead include selecting one of a plurality of pre-fabricated earpieces corresponding to the three-dimensional model for use by the subject based upon the simulation result, thereby providing a selection, or suggesting one such earpiece for manual selection by a user. Where the selection is automated, the selection may be displayed in a user interface or the like for review by a user. This may also or instead include fabricating an earpiece based upon the three-dimensional model, or otherwise providing fabrication instructions based upon the model.

It will be readily appreciated that a device such as any of the devices described above may be adapted to perform the method of FIG. 22 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 2200.

Figure 23:
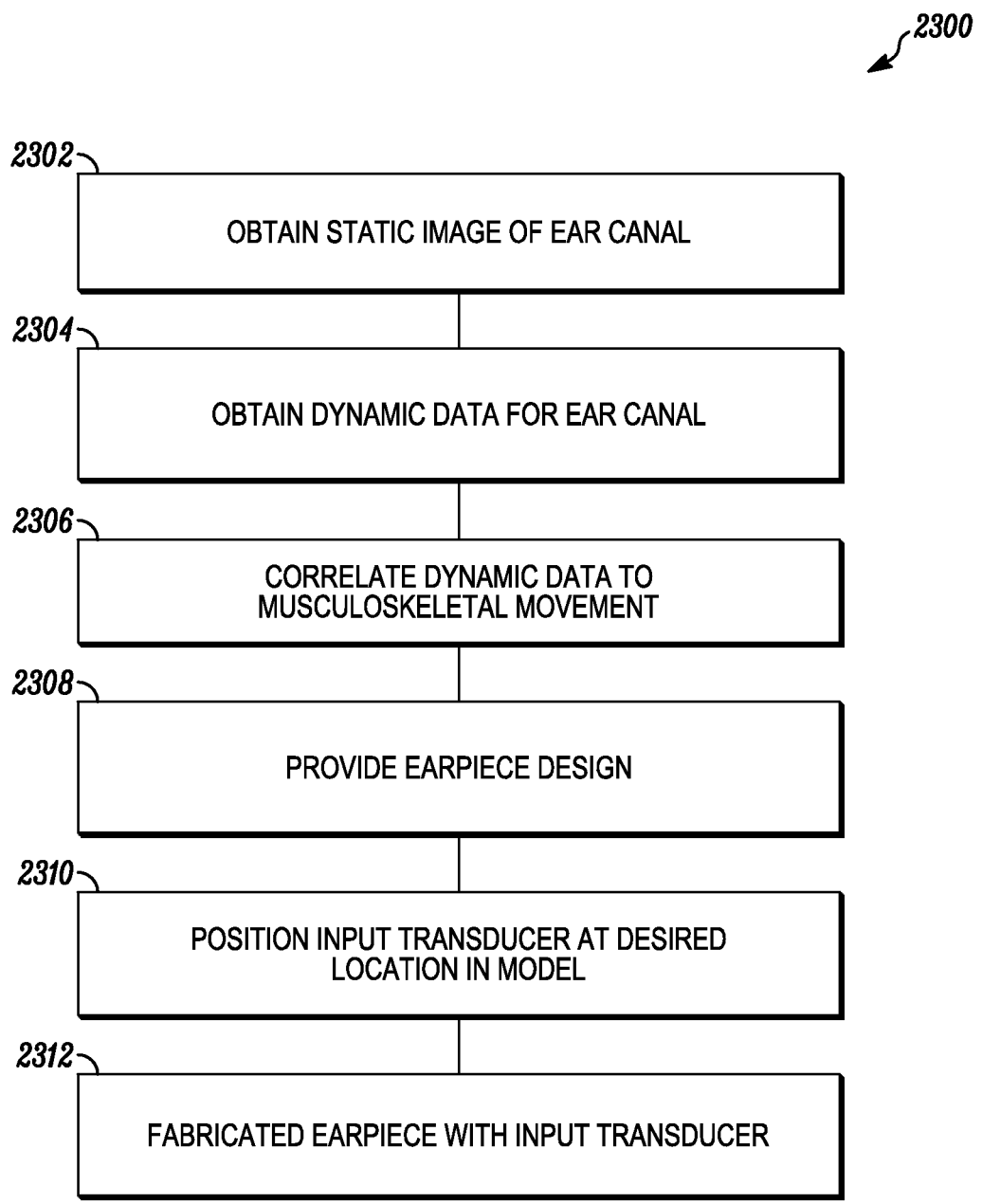
FIG. 23 is a flowchart of a method for positioning control inputs in an earpiece.

FIG. 23 is a flowchart of a method for positioning control inputs in an earpiece. As noted above, the three-dimensional imaging techniques described above permit measurement of ear canal shape change that can be correlated to musculoskeletal movements of a subject. Using this data, areas of maximum deflection of an ear canal can be identified and inputs can be positioned at complementary locations on an earpiece to detect, e.g., a yawn, a sidewise jaw movement, or any other motion or combination of motions that result in shape change within the ear canal. The earpiece may then be programmed to respond to such movements, thus permitting hands-free control of the earpiece with properly orchestrated musculoskeletal movements. By way of non-limiting example, a user may raise both eyebrows to mute a speaker in an earpiece or turn the head from side to side to increase the volume. More generally, any detectable input may be used to control any controllable feature of the earpiece based upon the techniques described below.

As shown in step 2302, the method 2300 may begin with obtaining static data from an ear canal of a subject, the static data including a three-dimensional image of a surface of the ear canal at a predetermined pressure.

As shown in step 2304, the method 2300 may include obtaining dynamic data from the ear canal of the subject, the dynamic data including data from the ear canal characterizing a shape change of the ear canal in response to a musculoskeletal movement of a head of the subject.

As shown in step 2306, the method 2300 may include correlating the shape change to the musculoskeletal movement to identify a surface region of the ear canal where the shape change due to the musculoskeletal movement meets or exceeds a predetermined threshold. It will be understood that the predetermined threshold may be any of a variety of relative or absolute thresholds. For example, a relative threshold may be a percentage change in position relative to an overall dimension or relative to other surface points on an ear canal. The threshold may also or instead include an absolute threshold such as a minimum or maximum surface displacement or an average surface displacement measured, e.g., over the duration of a musculoskeletal movement. In another aspect, the predetermined threshold may be a time-varying displacement. Thus for example, when a particular word is spoken (or the corresponding jaw, lip, and tongue movements made), the ear canal may exhibit a time-varying shape change with various minima and maxima at various locations. A particular displacement pattern at a particular location may serve as a threshold for detection of a corresponding musculoskeletal movement regardless of overall regions of maximum displacement.

As shown in step 2308, the method 2300 may include providing an earpiece design including a three-dimensional model of an earpiece fitted to the ear canal based upon the static data.

As shown in step 2310, the method 2300 may include positioning an input transducer in the earpiece design in a location corresponding to the surface region of the ear canal where the shape change due to the musculoskeletal movement meets or exceeds a predetermined threshold when the earpiece is placed for use in the ear canal. It will be understood that a variety of input transducers may be employed including without limitation optical switches, hall effect switches, motion detection switches, inertial switches, pressure-sensitive switches, and so forth. The step of position the input transducer may be aided by displaying within a user interface areas of the ear canal that exhibit a substantial shape change in response to the musculoskeletal movement and permitting a user to manually position the input transducer, which may be color-coded or otherwise annotated to indicate magnitude of displacement. This may, for example, include displaying an amount of shape change at one or more surface regions of the ear canal in response to the musculoskeletal movement, such as with textual, numeric, or color-coded annotations. It should further be appreciated that the musculoskeletal movement may be a time-varying movement over a period of time. For example, the movement may include saying a word such as 'mute', which may create a correspondingly time-varying predetermined threshold rather than a static measurement of when a positional limit has been exceeded.

As shown in step 2312, the method 2300 may include fabricating an earpiece with an input transducer positioned according to the design of step 2310. It will be appreciated that fabricating an earpiece may include any number of additional fabrication steps known to one of skill in the art, such as coupling the input transducer to control circuitry for the earpiece, such as a volume control, mute control, power control, and so forth. Where the earpiece is an earbud for an audio player, the input transducer may also or instead usefully control track selection playback start and stop, and so forth.

It will be readily appreciated that a device such as any of the devices described above may be adapted to perform the method of FIG. 23 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 2300.

Figure 24:
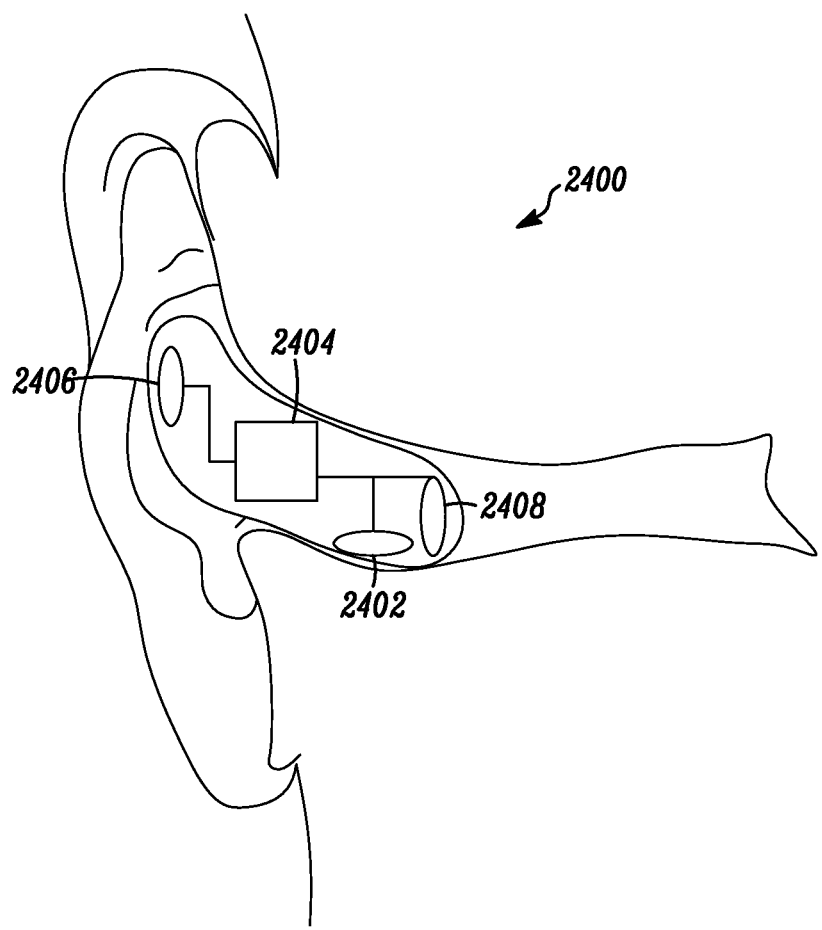
FIG. 24 shows an earpiece designed according to the method of FIG. 23.

FIG. 24 shows an earpiece designed according to the method of FIG. 23. In general, the earpiece 2400 may include a transducer 2402, a processor 2404, a microphone 2406, and a speaker 2408. The earpiece 2400 may be shaped and sized for an ear canal of a subject. The transducer 2402 may be any transducer sensitive to pressure, either directly (as in a pressure sensitive switch) or indirectly (as in a motion or distance detection sensor).

In general, the transducer 2402 may be positioned within the earpiece at a position that, when the earpiece 2400 is placed for use in the ear canal, corresponds to a location on a surface of the ear canal that exhibits a substantial shape change correlated to a musculoskeletal movement of the subject. The position depicted in FIG. 24 is provided by way of example only, and it will be understood that any position exhibiting substantial displacement may be used to position the transducer 2402 for use as contemplated herein. In one aspect, the transducer 2402 may be positioned at a position that, when the earpiece is placed for use in the ear canal, corresponds to a location on a surface of the ear canal that exhibits a maximum surface displacement from a neutral position in response to the musculoskeletal movement of the subject. In another aspect, the transducer 2402 may be positioned at a position that, when the earpiece is placed for use in the ear canal, corresponds to a location on a surface of the ear canal that exceeds an average surface displacement from a neutral position in response to the musculoskeletal movement of the subject. It will be understood that, while a single transducer 2402 is depicted, a number of transducers may be included, which may detect different musculoskeletal movements, or may be coordinated to more accurately detect a single musculoskeletal movement.

Figure 25:
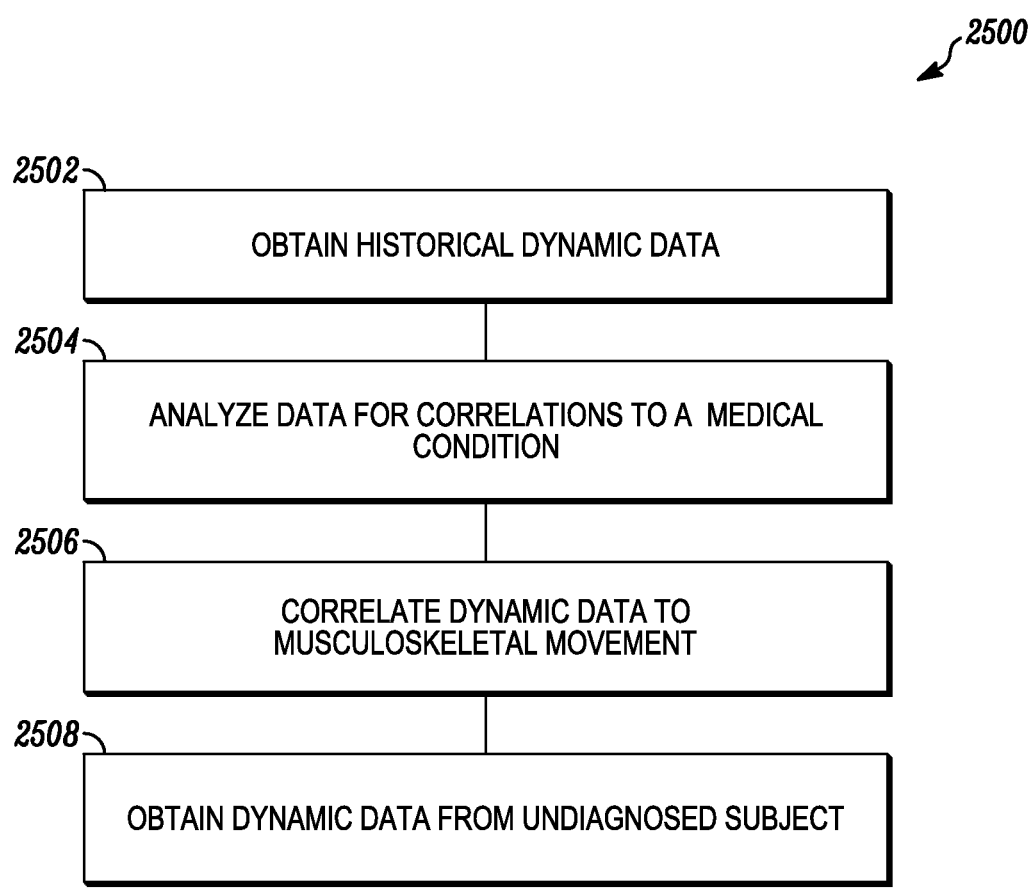
FIG. 25 is a flowchart of a method for using dynamic ear canal data for medical diagnosis.

The processor 2404 may be coupled to the microphone 2406, speaker 2408, and transducer 2402, and may be configured to detect the musculoskeletal movement of the subject based upon a pressure change signal from the transducer 2402, and to generate a predetermined control signal in response to the musculoskeletal movement. The predetermined control signal may, for example, be a mute signal for the earpiece, a volume change signal for the earpiece, or, where the earpiece is an earbud for an audio player (in which case the microphone 2406 may optionally be omitted), a track change signal for the audio player coupled to the earpiece. In one aspect, the FIG. 25 is a flowchart of a method for using dynamic ear canal data for medical diagnosis. In general, the systems and methods disclosed herein permit quick and accurate capture of ear canal data over a range of pressurizations and/or a range of musculoskeletal movements. Where this generally dynamic behavior of the ear canal can be correlated to particular medical conditions, a dynamic data ear canal scanner may be configured as a diagnostic tool for detection of those conditions.

As shown in step 2502, the method 2500 may begin by obtaining dynamic data from a plurality of ear canals of a plurality of subjects, the dynamic data for each of the ear canals including data from the ear canal characterizing a change in a shape of the ear canal related to at least one of a compliance of the ear canal to changes in pressurization or a shape change of the ear canal in response to a musculoskeletal movement of a head of a corresponding one of the subjects, wherein some of the subjects have been diagnosed with a medical condition. It will be understood that static data may also be obtained from a plurality of ear canals of a plurality of subjects, including three-dimensional images of the ear canal at a predetermined pressure. This static data may be used, for example, as a baseline for identifying surface displacements in the dynamic data relative to the static data.

Obtaining dynamic data may include obtaining data using any of the methods and systems described above. Thus for example, obtaining dynamic data may include, for each one of the plurality of ear canals of the plurality of subjects, inflating an inflatable membrane within the ear canal so that the inflatable membrane conforms to an inner surface of the ear canal and capturing a plurality of distance measurements from a sensor within the inflatable membrane to a surface of the inflatable membrane, thereby providing a three-dimensional image of the inflatable membrane in a shape that is conformed to the ear canal.

As shown in step 2504, the dynamic data may be analyzed to identify a correlation between the medical condition and the dynamic data for the ones of the subjects that have been diagnosed with the medical condition. The techniques for such correlation are well known in the art and are not described here in detail, except to note that the strength of or statistical confidence in a correlation may affect the diagnostic significance ascribed to a particular match based upon the correlation.

As shown in step 2506, the correlation, where identified may subsequently be used as a predictor for the medical condition. Thus in one aspect there is disclosed herein a diagnostic method and system based upon dynamic ear canal data, which may be captured using any of the imaging systems and methods described above. It will be readily appreciated that any body cavity amenable to dynamic data capture may be similarly obtained for a population and used to identify correlations with diagnostic significance.

As shown in step 2508, the method may include obtaining second dynamic data from an ear canal of an undiagnosed subject and calculating a likelihood that the undiagnosed subject has the medical condition based upon the correlation. This may obtained using any of the techniques described above. Thus for example obtaining second dynamic data may include inflating an inflatable membrane within the ear canal of an undiagnosed subject so that the inflatable membrane conforms to an inner surface of the ear canal and capturing a plurality of distance measurements from a sensor within the inflatable membrane to a surface of the inflatable membrane, thereby providing a three-dimensional image of the inflatable membrane in a shape that is conformed to the ear canal.

It will be readily appreciated that a device such as any of the devices described above may be adapted to perform the method of FIG. 25 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 2500. Thus in one aspect there is disclosed herein a diagnostic tool for performing diagnoses based upon a capture of static and dynamic data from an ear canal of an undiagnosed subject.

Figure 26:
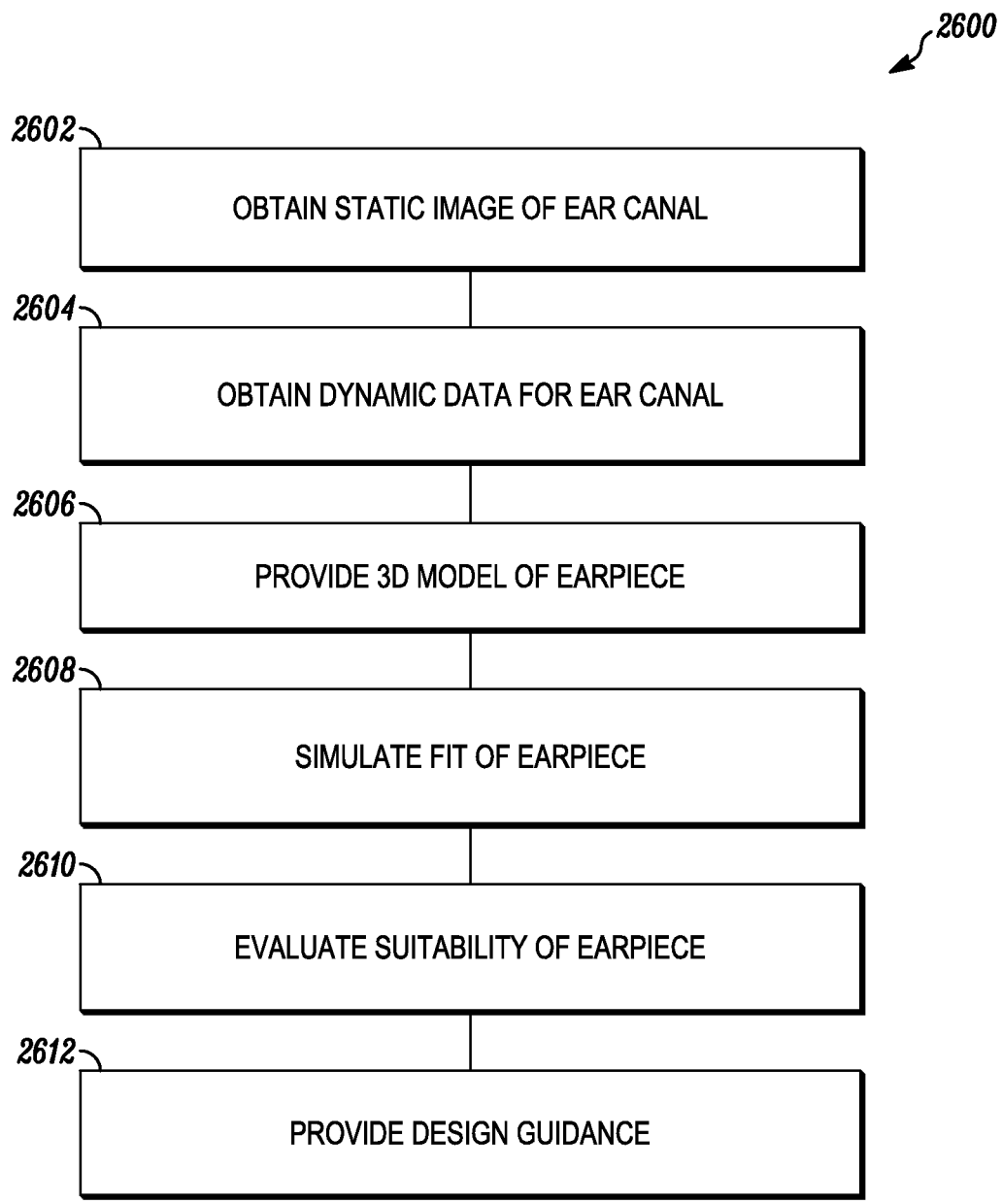
FIG. 26 is a flowchart of a method for fitting an earpiece using dynamic data.

FIG. 26 is a flowchart of a method for fitting an earpiece using dynamic data.

As shown in step 2602, the method 2600 may begin with obtaining static data from an ear canal of a subject, the static data including a three-dimensional image of a surface of the ear canal at a predetermined pressure.

As shown in step 2604, the method 2600 may include obtaining dynamic data from the ear canal of the subject, the dynamic data including data from the ear canal characterizing changes in a shape of the ear canal related to a compliance of the ear canal to changes in pressurization and a shape change of the ear canal in response to a musculoskeletal movement of a head of the subject.

As shown in step 2606, the method may include providing a three-dimensional model of an earpiece, such as any of the three-dimensional models described above.

As shown in step 2608, the method 2600 may include evaluating a fit of the three-dimensional model of the earpiece to the ear canal based on the static data and the dynamic data. This may include any of the fit or simulation tests described above to determine a quality and comfort of the modeled earpiece in the measured ear canal. For example, this may include evaluating the fit according to pressure applied by the earpiece to the ear canal. This may also or instead include evaluating the fit according to the size of the earpiece relative to the size of the ear canal in one or more regions of low compliance, that is, regions where the ear canal does not yield to the earpiece (e.g., regions with substantial adjacent bone or cartilage). This may also or instead include valuating the fit according to an acoustic seal of the earpiece, or evaluating the fit to identify one or more deformation modes of the earpiece when placed for use in the ear canal. For example, where the ear canal exhibits substantial curvature, the earpiece may need substantial axial flexibility for insertion and removal. Thus the one or more deformation modes may include deformation during insertion of the removal of the earpiece. This may also or instead include deformation modes caused by a shape change of the ear canal in response to musculoskeletal movement of the head of the subject, or deformation modes induced by the relative stiffness and shape of the earpiece and/or ear canal.

As shown in step 2610, the method 2600 may include modifying a characteristic of the three-dimensional model to improve the fit. This may include modifying a shell for an earpiece, modifying a shape of the earpiece, selecting different (e.g., firmer or softer) materials for fabrication of the earpiece or otherwise modifying a material profile of the three dimensional model, and so forth. Modifying the characteristic may also or instead include positioning an articulating joint within the three-dimensional model, e.g., to accommodate axial deformation during insertion/removal of the earpiece. Modifying the characteristic may also or instead include modifying an elasticity of a portion of the three-dimensional model.

It will further be appreciated that, based on the compliance data captured during a scan, a good estimate can be obtained of the maximum short-duration expansion of regions of the ear canal. This data may be useful for modeling the insertion and removal of the earpiece, and modifying the earpiece design accordingly to reduce discomfort during insertion and removal of the earpiece.

It will be readily appreciated that a device such as any of the devices described above may be adapted to perform the method of FIG. 26 with suitable programming or other configuration of the processor and/or other processing circuitry. Also disclosed herein is a computer program product comprising computer executable code embodied in a non-transitory computer readable medium that, when executing on one or more computing devices, performs the processing steps associated with the method 2600.

It will be appreciated that any of the above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. At the same time, processing may be distributed across devices such as a camera and/or computer and/or server or other remote processing resource in a number of ways, or all of the functionality may be integrated into a dedicated, standalone device. All such permutations and combinations are intended to fall within the scope of the present disclosure.

In other embodiments, disclosed herein are computer program products comprising computer-executable code or computer-usable code that, when executing on one or more computing devices, performs any and/or all of the steps described above. The code may be stored in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the processes described above may be embodied in any suitable transmission or propagation medium carrying the computer-executable code described above and/or any inputs or outputs from same.

While the invention has been disclosed in connection with the preferred embodiments shown and described in detail, various modifications and improvements thereon will become readily apparent to those skilled in the art. Accordingly, the spirit and scope of the present invention is not to be limited by the foregoing examples, but is to be understood in the broadest sense allowable by law.

What is claimed is:

1. A method comprising:
    inserting an inflatable membrane into an ear canal of a subject;
    pressurizing the inflatable membrane within the ear canal with a fluid to a predetermined pressure, thereby providing an inflated membrane;
    obtaining a first three-dimensional image of a surface of the inflated membrane at the predetermined pressure;
    causing a musculoskeletal movement of a head of the subject;
    obtaining a plurality of three-dimensional images in a three-dimensional video from a series of time-separated measurements during the musculoskeletal movement, the plurality of three-dimensional images including a second three-dimensional image of the surface after the musculoskeletal movement;
    identifying a change in shape of the surface between the first three-dimensional image and the second three-dimensional image, the change in shape including a plurality of intermediate shapes during the musculoskeletal movement; and
    storing the change in shape as ear canal shape change data for the subject.

2. The method of claim 1 wherein storing the change in shape includes storing the first three-dimensional image and the second three-dimensional image.

3. The method of claim 1 wherein storing the change in shape includes storing a movement between the first three-dimensional image and the second three-dimensional image.

4. The method of claim 1 wherein storing the change in shape includes storing a displaced volume between the first three-dimensional image and the second three-dimensional image.

5. The method of claim 1 further comprising relating the musculoskeletal movement to the change in shape.

6. The method of claim 1 further comprising analyzing the ear canal shape change data to quantitatively characterize how the ear canal changes shape in response to the musculoskeletal movement.

7. The method of claim 1 wherein the fluid includes at least one of a gas, a liquid, a gel, and a foam.

8. The method of claim 1 further comprising characterizing the musculoskeletal movement of the head as a type of movement and storing the type of movement.

9. The method of claim 1 further comprising measuring the muscoluskeletal movement of the head.

10. The method of claim 1 further comprising obtaining two or more three-dimensional images of the head of the subject to quantitatively characterize the musculoskeletal movement.

11. The method of claim 10 wherein the two or more three-dimensional images include at least one three-dimensional image before causing the movement.

12. The method of claim 10 wherein the two or more three-dimensional images include at least one three-dimensional image after causing the movement.

13. The method of claim 10 wherein the two or more three-dimensional images include at least one three-dimensional image during the movement.

14. A computer program product comprising computer executable code embodied in a non-transitory computer readable medium that, when executing on one or more computing devices, performs the steps of:

inserting an inflatable membrane into an ear canal of a subject;

pressurizing the inflatable membrane within the ear canal with a fluid to a predetermined pressure, thereby providing an inflated membrane;

obtaining a first three-dimensional image of a surface of the inflated membrane at the predetermined pressure;

causing a muscoluskeletal movement of a head of the subject;

obtaining a plurality of three-dimensional images in a three-dimensional video from a series of time-separated measurements during the musculoskeletal movement, the plurality of three-dimensional images including a second three-dimensional image of the surface after the muscoluskeletal movement;

identifying a change in shape of the surface between the first three-dimensional image and the second three-dimensional image, the change in shape including a plurality of intermediate shapes during the musculoskeletal movement; and storing the change in shape as ear canal shape change data for the subject.

* * * * *

UNITED STATES PATENT AND TRADEMARK OFFICE
CERTIFICATE OF CORRECTION

| | | |
|---|---|---|
| PATENT NO. | : 8,493,574 B2 | Page 1 of 1 |
| APPLICATION NO. | : 13/760576 | |
| DATED | : July 23, 2013 | |
| INVENTOR(S) | : Douglas P. Hart et al. | |

It is certified that error appears in the above-identified patent and that said Letters Patent is hereby corrected as shown below:

In the Specification

Column 41, Line 47, "different discrete muscoluskeletal positions, this is the most" should read -- different discrete musculoskeletal positions, this is the most --

In the Claims

Claim 1, Column 54, Line 35, "causing a muscoluskeletal movement of a head of the subject" should read -- causing a musculoskeletal movement of a head of the subject --

Claim 1, Column 54, Line 42, "muscoluskeletal movement;" should read -- musculoskeletal movement; --

Claim 9, Column 55, Line 5, "muscoluskeletal movement of the head." should read -- musculoskeletal movement of the head. --

Claim 9, Column 55, Line 8, "subject to quantitatively characterize the muscoluskeletal" should read -- subject to quantitatively characterize the musculoskeletal --

Claim 14, Column 56, Line 8, "causing a muscoluskeletal movement of a head of the subject" should read -- causing a musculoskeletal movement of a head of the subject --

Claim 14, Column 56, Line 14, "muscoluskeletal movement;" should read -- musculoskeletal movement; --

Signed and Sealed this
First Day of October, 2013

Teresa Stanek Rea
*Deputy Director of the United States Patent and Trademark Office*